US009006515B2

(12) United States Patent
Cigan et al.

(10) Patent No.: US 9,006,515 B2
(45) Date of Patent: Apr. 14, 2015

(54) POLLEN PREFERRED PROMOTERS AND METHODS OF USE

(75) Inventors: Andrew Mark Cigan, Johnston, IA (US); Shai J Lawit, Urbandale, IA (US)

(73) Assignee: Pioneer Hi Bred International Inc, Johnston, IA (US)

( * ) Notice: Subject to any disclaimer, the term of this patent is extended or adjusted under 35 U.S.C. 154(b) by 413 days.

(21) Appl. No.: 13/445,288

(22) Filed: Apr. 12, 2012

(65) Prior Publication Data
US 2013/0180006 A1    Jul. 11, 2013

Related U.S. Application Data

(60) Provisional application No. 61/583,643, filed on Jan. 6, 2012.

(51) Int. Cl.
*C12N 15/82* (2006.01)
*C12N 15/87* (2006.01)
*A01H 5/00* (2006.01)

(52) U.S. Cl.
CPC .................................. *C12N 15/8231* (2013.01)

(58) Field of Classification Search
None
See application file for complete search history.

(56) References Cited

U.S. PATENT DOCUMENTS

| | | | |
|---|---|---|---|
| 7,241,939 B1 * | 7/2007 | Eby ................................ | 800/312 |
| 7,667,097 B2 * | 2/2010 | Scheirlinck et al. ........... | 800/287 |
| 7,977,092 B2 | 7/2011 | Gostjeva et al. | |
| 7,977,534 B2 | 7/2011 | Zuo et al. | |
| 2011/0165679 A1 | 7/2011 | Gordon-Kamm et al. | |
| 2011/0167516 A1 | 7/2011 | Gordon-Kamm et al. | |
| 2012/0042408 A1 | 2/2012 | Mercier et al. | |
| 2012/0199144 A2 * | 8/2012 | Jones et al. .................... | 131/275 |

FOREIGN PATENT DOCUMENTS

| | | |
|---|---|---|
| EP | 1 528 105 A1 | 5/2005 |
| EP | 2 208 790 A1 | 7/2010 |
| WO | 0185963 A2 | 11/2001 |
| WO | 2009124282 A1 | 10/2009 |
| WO | 2011017422 A2 | 2/2011 |
| WO | 2011044132 A1 | 4/2011 |
| WO | 2011082310 A2 | 7/2011 |
| WO | 2011082318 A2 | 7/2011 |
| WO | 2010079432 A1 | 10/2011 |
| WO | 2012075195 A1 | 6/2012 |

OTHER PUBLICATIONS

Grey-Mitsumune and Matton; "The Egg apparatus 1 gene from maize is a member of a large gene family found in both monocots and dicots"; Planta (2006) 223:618-625; Springer-Verlag; Berlin/Heidelberg, DE.
d'Erfurth, et al.,; "Turning Meiosis into Mitosis"; PLOS Biology (2009) 7(6):e1000124; www.plosbiology.org.
Marimuthu, et al.; "Synthetic Clonal Reproduction Through Seeds"; Science (2011) 331:876; American Association for the Advancement of Science; Washington, DC US.
Sanchez-Leon, et al.; "Transcriptional analysis of the *Arabidopsis* ovule by massively parallel signature sequenceing"; Journal of Experimental Botany (2012) Advance Access doi:10.1093/jxb/ers075.
Koszegi, D.; "RKD genes: a novel transcription factor family involved in the female gametophyte development of *Arabidopsis* and wheat"; Sep. 25, 2008; PhD Dissertation.
Moraes, et al.; "Recognition of *A. thaliana* centromeres by heterologous CENH3 requires high similarity to the endogenous protein"; Plant Mol Biol (2011) 75:253-261; Springer, The Netherlands.
Ravi and Chan; "Haploid plants produced by centromere-mediated genome elimination"; Nature (2010) 464:615-619; Nature Publishing Group; London, UK.
Koszegi, et al.; "RKD controls egg cell transcriptional program"; The Plant Journal (2001) Accepted Article; doi: 10.111/j.1365-313X. 2011.04592.x.
Lermontova, et al.; "Loading of *Arabidopsis* Centromeric Histone CENH3 Occurs Mainly during G2 and Requires the Presence of the Histone Fold Domain"; The Plant Cell (2006) 18:2443-2451; American Society of Plant Physiologists; Rockville, MD US.
Chaudhury, et al.; "Fertilization-independent seed development in *Arabidopsis thaliana*"; Proc Natl Acad Sci USA (1997) 94:4223-4228; National Academy of Sciences; Washington DC US.
Steffen, et al.; "Identification of genes expressed in the *Arabidopsis* female gametophyte"; The Plant Journal (2007) 51:281-292; Blackwell Publishing Ltd. ; Oxford, UK.
Wuest, et al.; "*Arabidopsis* Female Gametophyte Gene Expression Map Reveals Similarities between Plant and Animal Gametes"; Current Biology (2010) 20:506-512; Elsevier Ltd; Amsterdam, The Netherlands.
Yang, et al.; "An Egg Apparatus-Specific Enhancer of *Arabidopsis*, Identified by Enhancer Detection"; Plant Physiology (2005) 139:1421-1432; American Society of Plant Biologists (ASPB); Rockville, MD US.
Bhat; "Genetic engineering of apomixis in plants: closer to reality"; J Plant Biochem Biotechnol (2011) 20(1):1-4; Springer; The Netherlands.
Chan; "Chromosome engineering: power tools for plant genetics"; Trends in Biotechnology (2010) 28(12):605-610; Elsevier, Ltd; Oxford, UK.
Mercier and Grelon; "Meiosis in plants: ten years of gene discovery"; Cytogentic and Genome Research (2008) 120:290; Karger AG; Basel, Switzerland.

(Continued)

*Primary Examiner* — Li Zheng
(74) *Attorney, Agent, or Firm* — Pioneer Hi-Bred Int'l Inc.

(57) ABSTRACT

Compositions and methods for regulating expression of heterologous nucleotide sequences in a plant are provided. Compositions include nucleotide sequences encompasses a strong pollen preferred promoter which drives strong, specific expression of gene products in pollen. Also provided is a method for expressing a heterologous nucleotide sequence in a plant using a promoter sequence disclosed herein.

15 Claims, 20 Drawing Sheets

(56) References Cited

OTHER PUBLICATIONS

Eyal, et al.; "Pollen Specificity Elements Reside in 30 bp of the Proximal Promoters of Two Pollen-Expressed Genes"; The Plant Cell (1995) 7:373-384; American Society of Plant Physiologists; Rockville, MD US.

Eady, et al.; "Differential activation nad conserved vegetative cell-specific activity of a late pollen promoter in species with bicellular and tricelluar pollen"; The Plant Journal (1994) 5(4):543-550; Blackwell Publishing; Oxford, UK.

EMBL Accession No. AZF01272, 2011.

* cited by examiner

POLLEN PREFERRED PROMOTERS AND METHODS OF USE

CROSS-REFERENCE

This utility application claims the benefit U.S. Provisional Application No. 61/583,643, filed Jan. 6, 2012, which is incorporated herein by reference.

FIELD OF THE DISCLOSURE

The present disclosure relates to the field of plant molecular biology, more particularly to regulation of gene expression in plants.

BACKGROUND OF THE DISCLOSURE

Expression of heterologous DNA sequences in a plant host is dependent upon the presence of operably linked regulatory elements that are functional within the plant host. Choice of the promoter sequence will determine when and where within the organism the heterologous DNA sequence is expressed. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized. Additional regulatory sequences upstream and/or downstream from the core promoter sequence may be included in the expression constructs of transformation vectors to bring about varying levels of expression of heterologous nucleotide sequences in a transgenic plant.

Frequently it is desirable to express a DNA sequence in particular tissues or organs of a plant. For example, increased resistance of a plant to infection by soil- and air-borne pathogens might be accomplished by genetic manipulation of the plant's genome to comprise a tissue-preferred promoter operably linked to a heterologous pathogen-resistance gene such that pathogen-resistance proteins are produced in the desired plant tissue. Alternatively, it might be desirable to inhibit expression of a native DNA sequence within a plant's tissues to achieve a desired phenotype. In this case, such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Additionally, it may be desirable to express a DNA sequence in plant tissues that are in a particular growth or developmental phase such as, for example, cell division or elongation. Such a DNA sequence may be used to promote or inhibit plant growth processes, thereby affecting the growth rate or architecture of the plant.

Isolation and characterization of pollen preferred promoters, particularly promoters that can serve as regulatory elements for expression of isolated nucleotide sequences of interest, are needed for impacting various traits in plants and for use with scorable markers.

BRIEF SUMMARY OF THE DISCLOSURE

Compositions and methods for regulating gene expression in a plant are provided. Compositions comprise novel nucleotide sequences for a promoter active in pollen tissues before, during, and/or after pollen germination. Certain embodiments of the disclosure comprise the nucleotide sequence set forth in SEQ ID NO: 53, 54, 55 and 56 and functional fragments thereof which drive pollen preferred-preferred expression of an operably-linked nucleotide sequence. Embodiments of the disclosure also include DNA constructs comprising a promoter operably linked to a heterologous nucleotide sequence of interest, wherein said promoter is capable of driving expression of said nucleotide sequence in a plant cell and said promoter comprises one of the nucleotide sequences disclosed herein. Embodiments of the disclosure further provide expression vectors, and plants or plant cells having stably incorporated into their genomes a DNA construct as is described above. Additionally, compositions include transgenic seed of such plants Further embodiments comprise a means for selectively expressing a nucleotide sequence in a plant, comprising transforming a plant cell with a DNA construct, and regenerating a transformed plant from said plant cell, said DNA construct comprising a promoter of the disclosure and a heterologous nucleotide sequence operably linked to said promoter, wherein said promoter initiates pollen preferred-preferred transcription of said nucleotide sequence in the regenerated plant. In this manner, the promoter sequences are useful for controlling the expression of operably linked coding sequences in a tissue-preferred manner.

Downstream from the transcriptional initiation region of the promoter will be a sequence of interest that will provide for modification of the phenotype of the plant. Such modification includes modulating the production of an endogenous product as to amount, relative distribution, or the like, or production of an exogenous expression product, to provide for a novel or modulated function or product in the plant. For example, a heterologous nucleotide sequence that encodes a gene product that confers resistance or tolerance to herbicide, salt, cold, drought, pathogen, nematodes or insects is encompassed.

In a further embodiment, a method for modulating expression of a gene in a stably transformed plant is provided, comprising the steps of (a) transforming a plant cell with a DNA construct comprising the promoter of the disclosure operably linked to at least one nucleotide sequence; (b) growing the plant cell under plant growing conditions and (c) regenerating a stably transformed plant from the plant cell wherein expression of the linked nucleotide sequence alters the phenotype of the plant.

DETAILED DESCRIPTION

Figure 1:
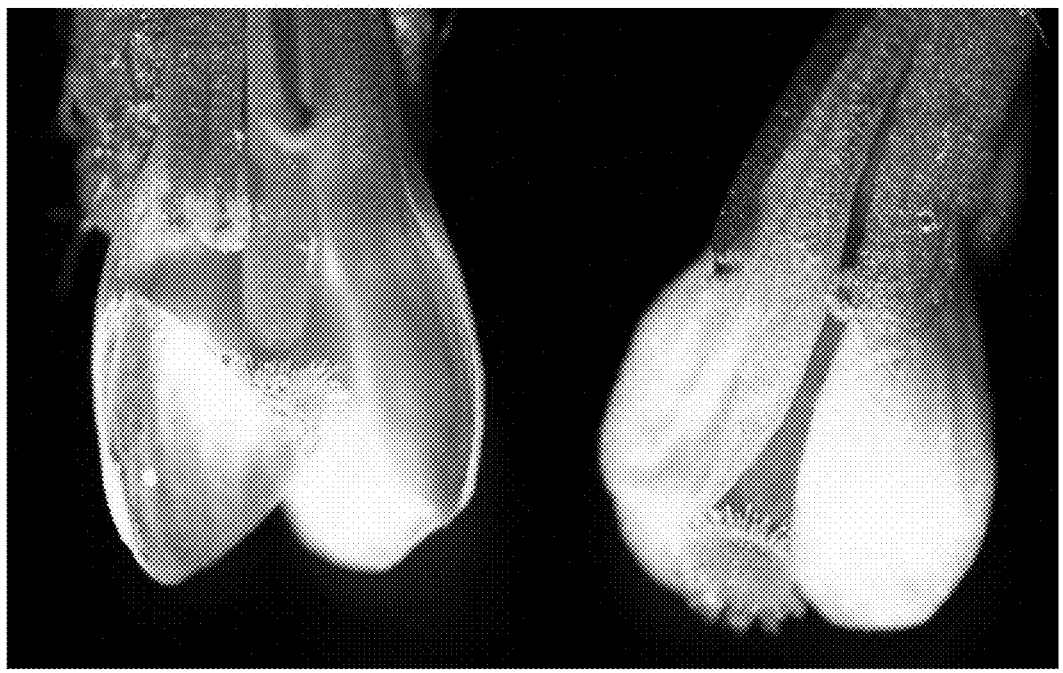
FIG. 1 At-LAT52 LP1 Pro: AC-GFP1 signal found to be very bright in pollen, note shed pollen on carpel wall.
Figure 1:
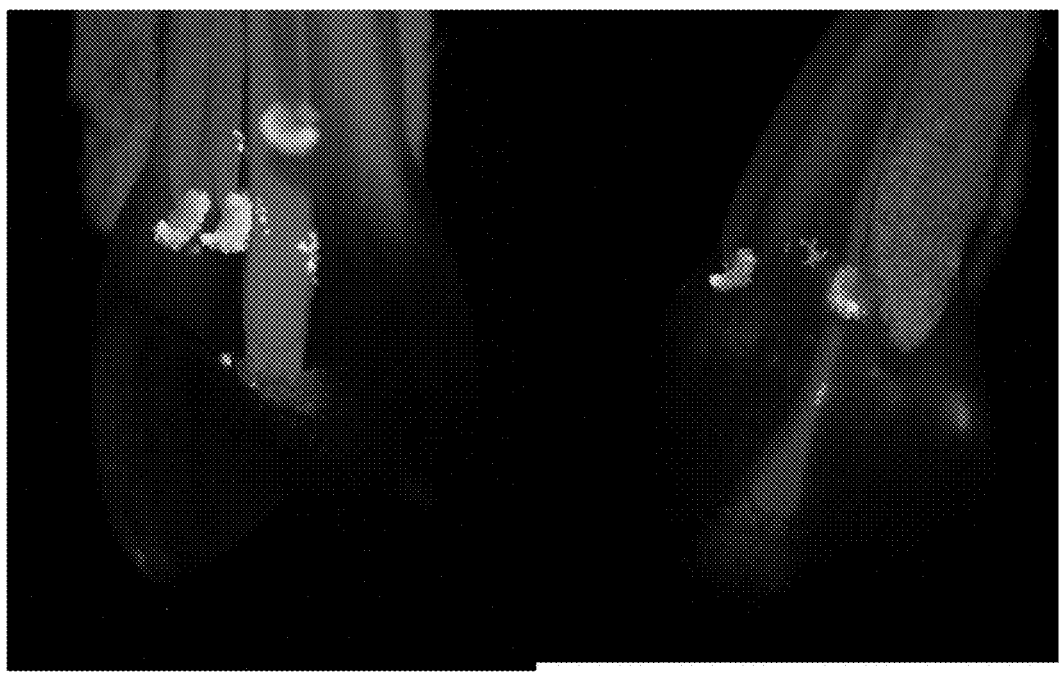
Figure 2:
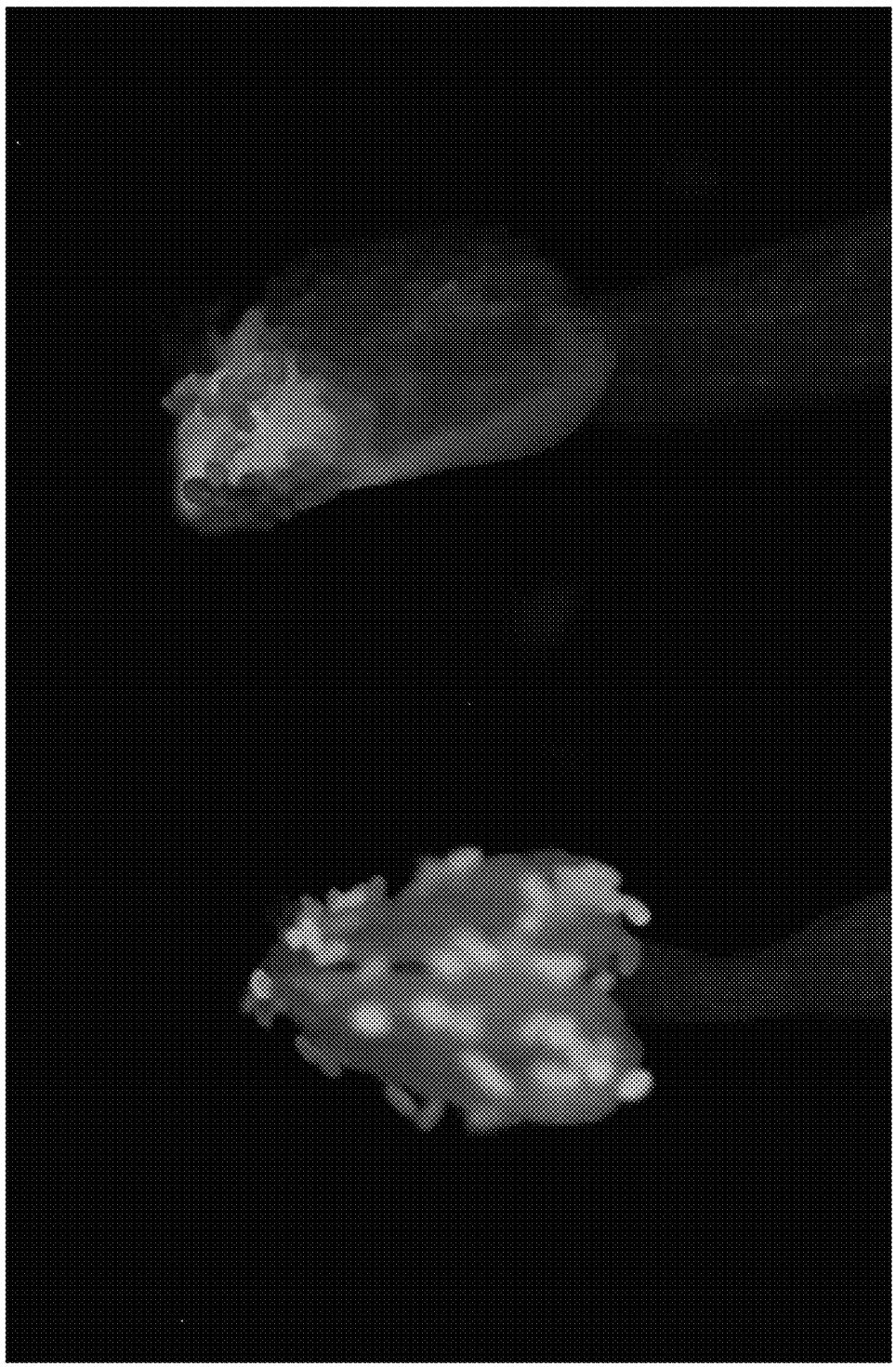
FIGS. 2(A and B) At-LAT52 LP1 Pro: AC-GFP1—Anthers. GFP pollen segregates for signal as expected. Note auto-fluorescence of anther (A), but not pollen in the negative control (B).
Figure 3:
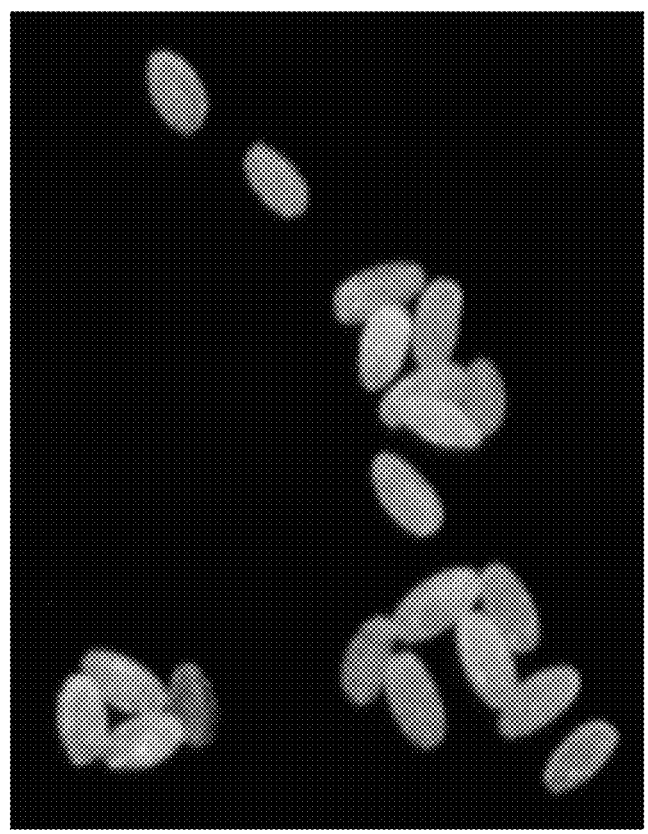
FIGS. 3(A and B) At-LAT52 LP1 Pro: AC-GFP1—Pollen Grains. GFP pollen segregates for signal as expected.
Figure 3:
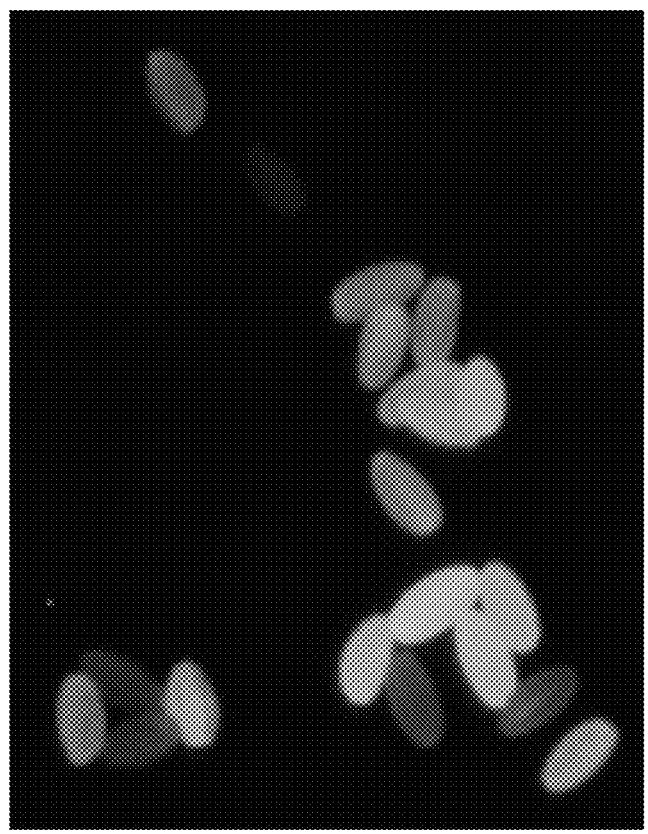
Figure 4:
FIG. 4 AT-LAT52LP2 PRO:AC-GFP1—GFP pollen segregates for signal as expected.
Figure 4:
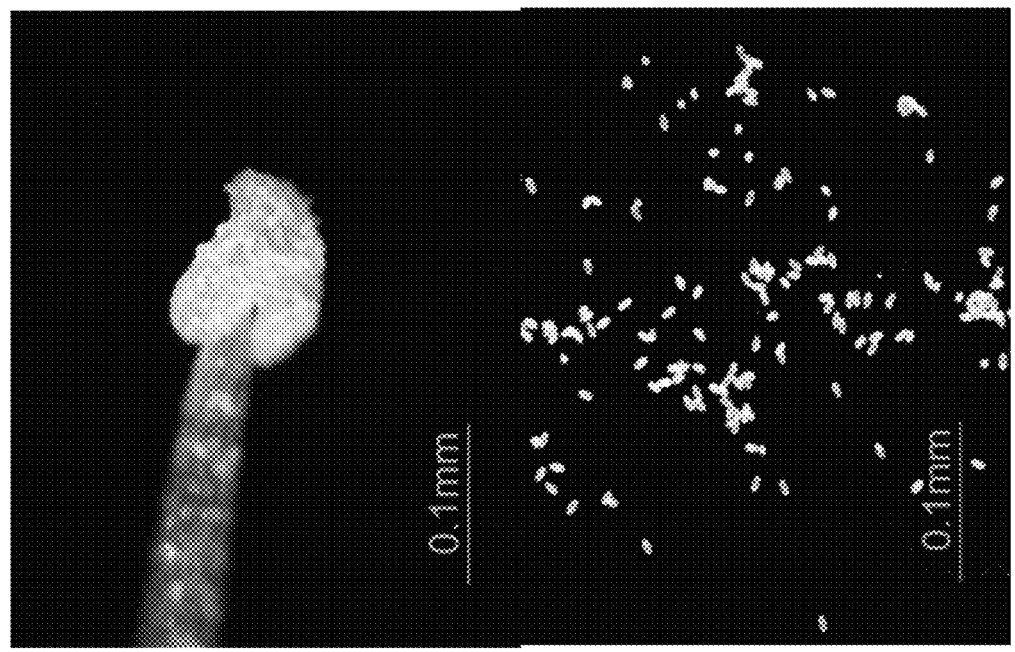
Figure 5:
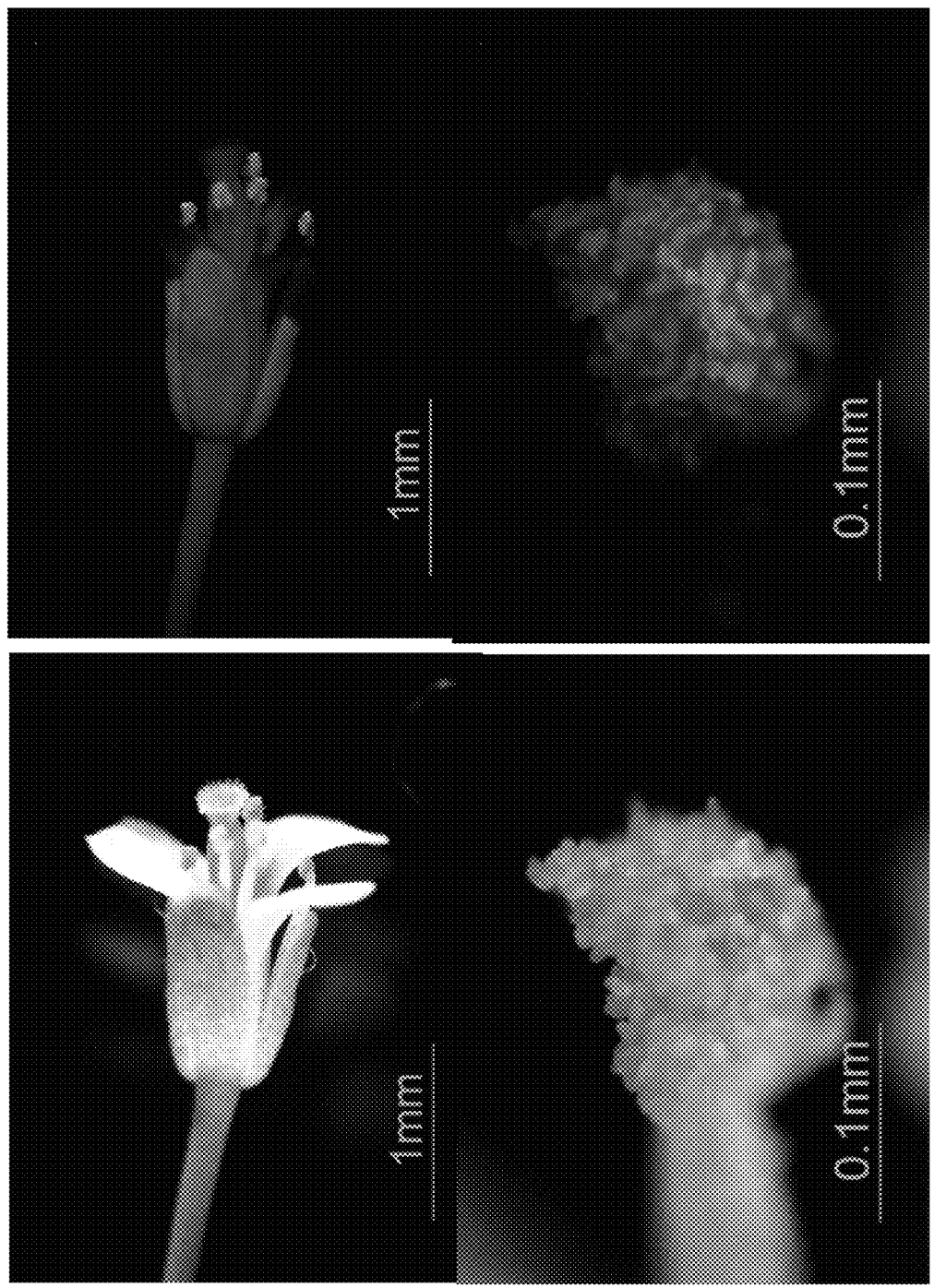
FIG. 5 AT-PPG1 PRO:AC-GFP1—GFP pollen demonstrates fluorescence and segregates for signal as expected.
Figure 6:
FIG. 6 AT-LAT52 LP2 PRO:BARNASE—BARNASE constructs tended to have plieotropic effects on the flowers. (A) short or missing petals, (B) disfigured outer floral organs and (C) disfigured outer floral organs.
Figure 6:
Figure 6:
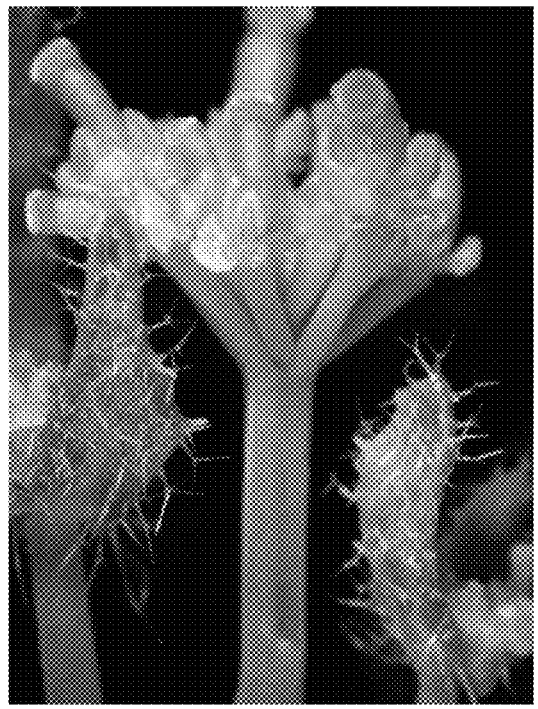
Figure 7:
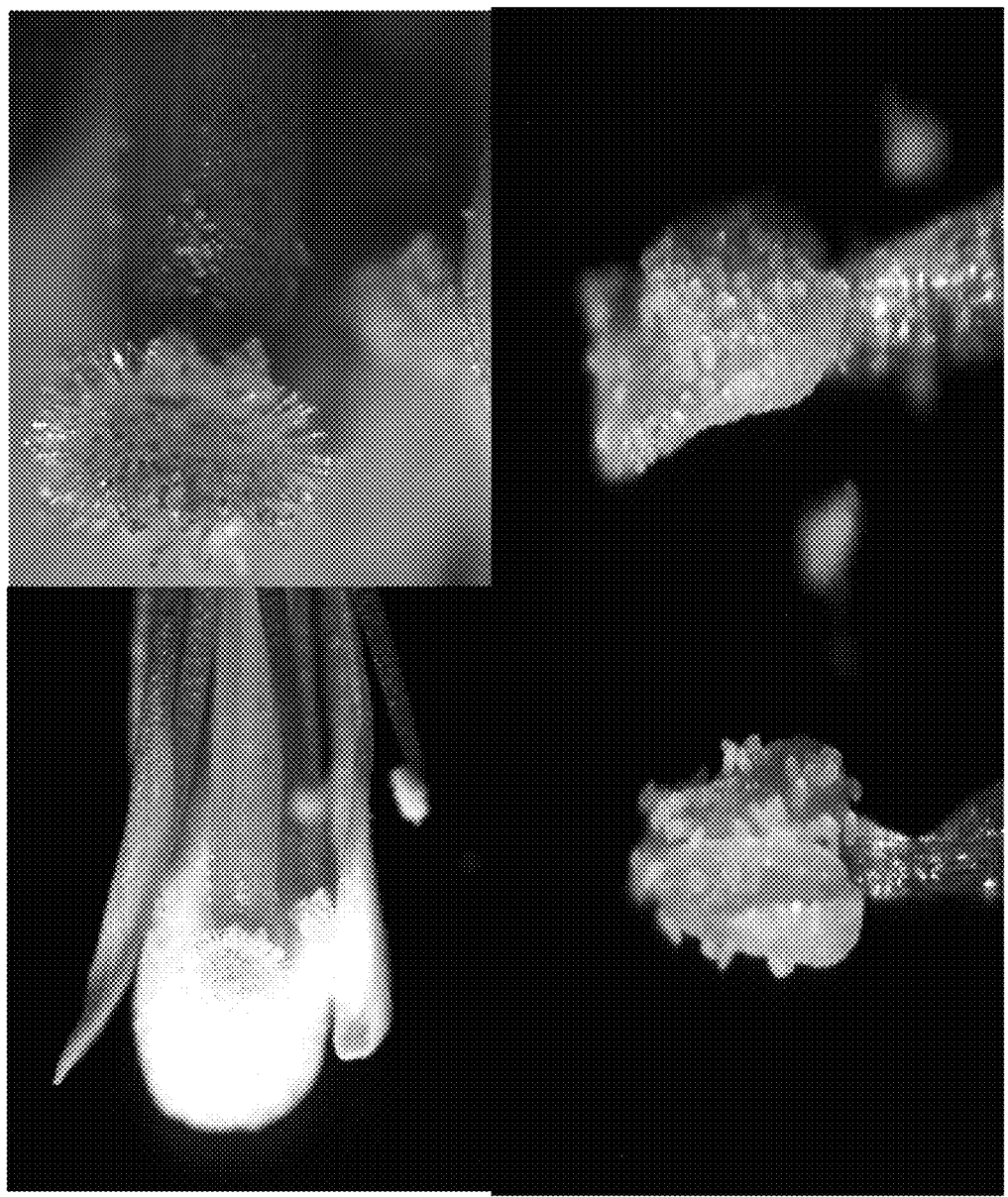
FIGS. 7(A and B) AT-PPG1 PRO:BARNASE appeared more normal than AT-LAT52 LP2:BARNASE. (A) non-transformed control (B) is transformed with BARNASE construct.
Figure 8:
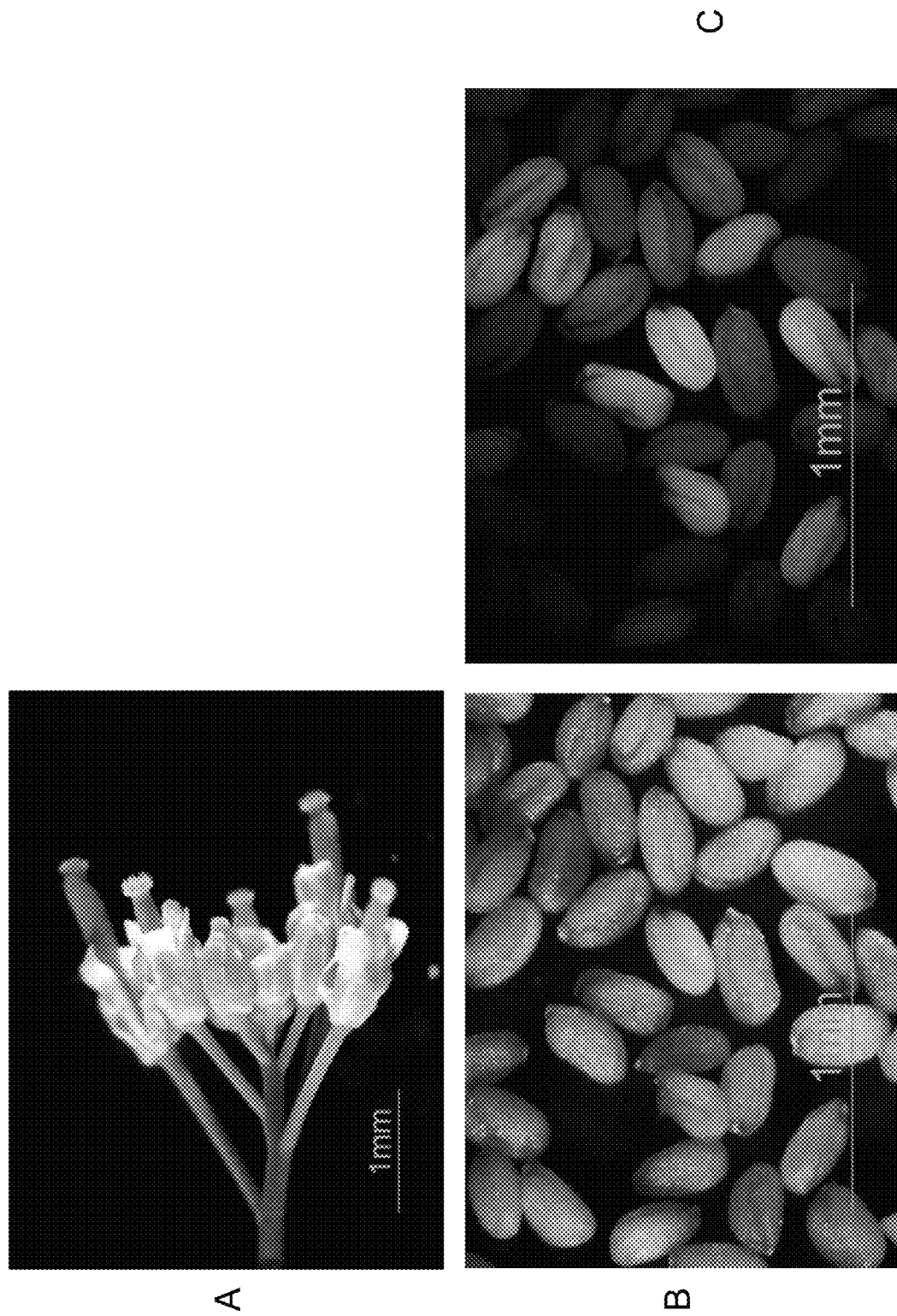
FIGS. 8(A, B and C) AT-LAT52LP1 PRO:BARNASE (A) Stunted petals, some floral plieotropism. In seed—(B) white light (C) fluorescent YFP filtered—the seed does segregate 1:1 as expected.
Figure 9:
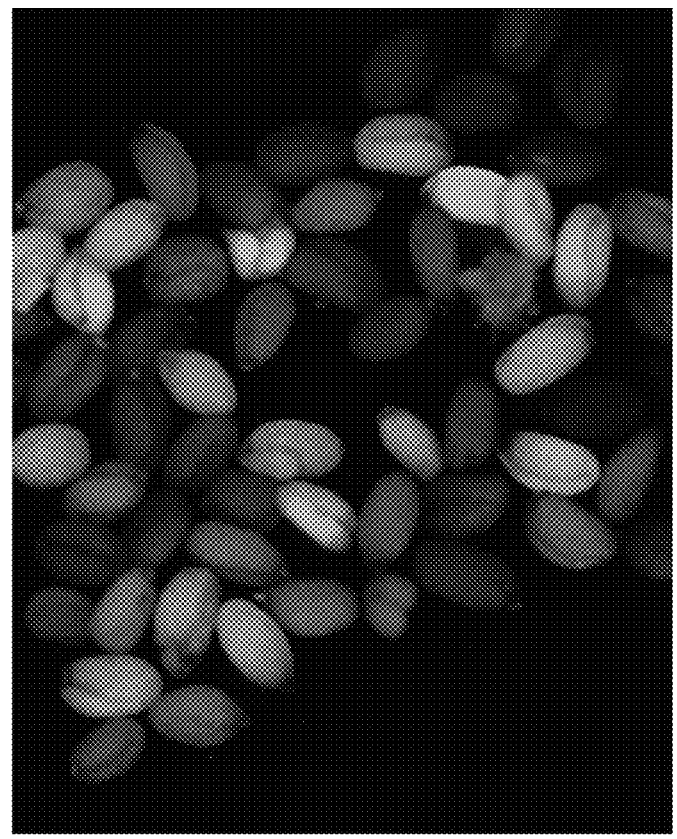
FIGS. 9(A and B) AT-LAT52LP2 PRO:ADP Ribosylase In seed—(A) white light (B) fluorescent YFP filtered—the seed does segregate 1:1 as expected.
Figure 9:
Figure 10:
FIGS. 10(A and B) AT-LAT52LP1 PRO:DMETH In seed—(A) white light (B) fluorescent YFP filtered—the seed does segregate 1:1 as expected.
Figure 10:
Figure 11:
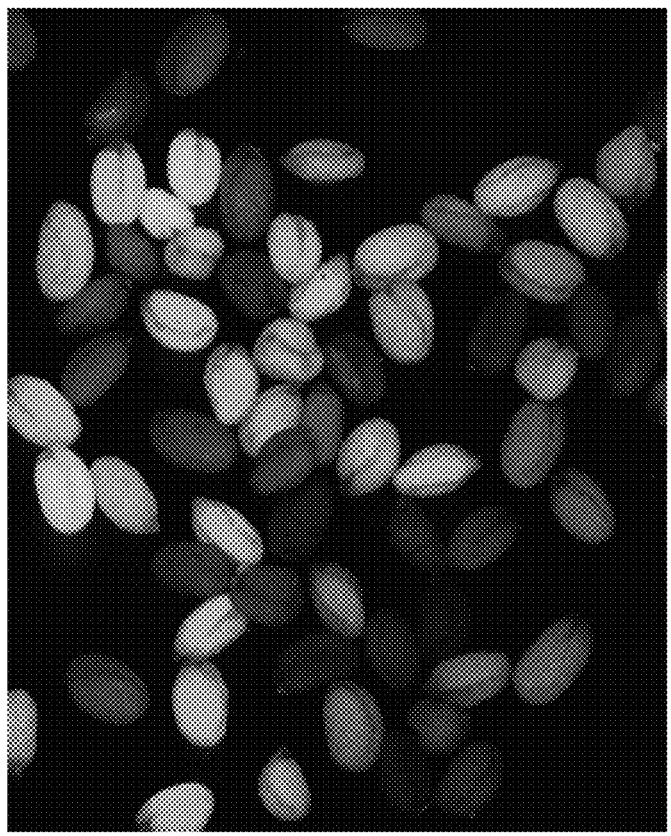
FIGS. 11(A and B) AT-LAT52LP2 PRO:DMETH In seed—(A) white light (B) fluorescent YFP filtered—the seed does segregate 1:1 as expected.
Figure 11:
Figure 12:
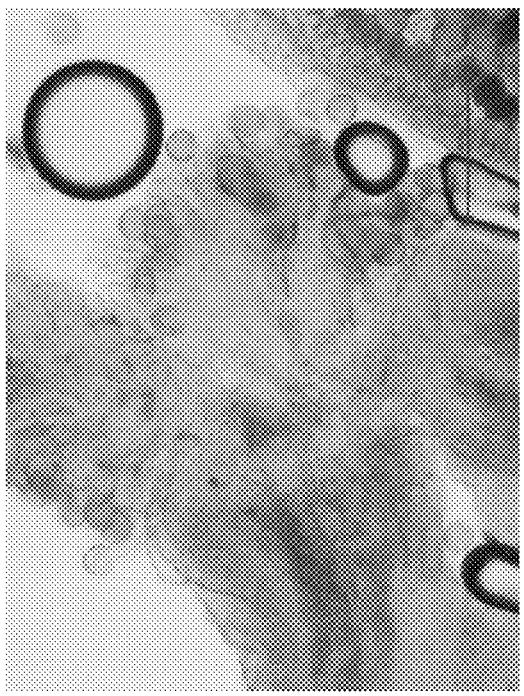
FIGS. 12(A, B and C) AT-PPG2 PRO:GUS (A) pollen preferred staining, (B) GUS staining shows expression signal still found in the pollen tubes and (C) showing a magnified view of an intact anther with expression confined to pollen grains.
Figure 12:
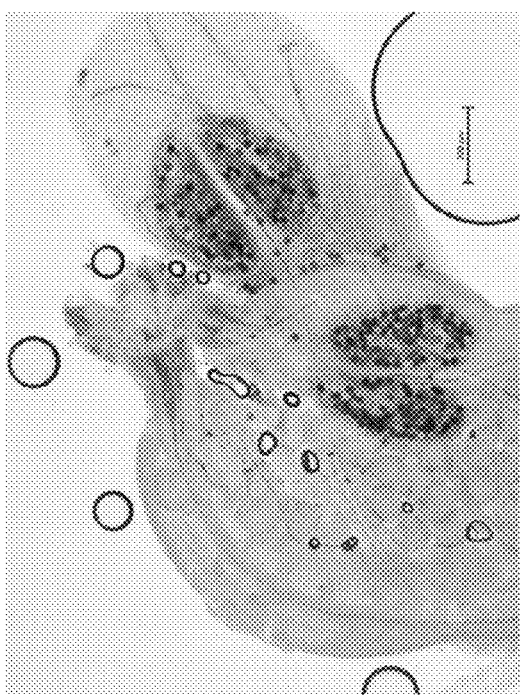
Figure 12:

The disclosure relates to compositions and methods drawn to plant promoters and methods of their use. The compositions comprise nucleotide sequences for a pollen preferred promoters. The compositions further comprise DNA constructs comprising a nucleotide sequence for the promoter region operably linked to a heterologous nucleotide sequence of interest. In particular, the present disclosure provides for isolated nucleic acid molecules comprising the nucleotide sequence set forth in SEQ ID NOS: 53, 54, 55 and 56, and fragments, variants and complements thereof.

The promoter sequences of the present disclosure include nucleotide constructs that allow initiation of transcription in a plant. In specific embodiments, the promoter sequence allows initiation of transcription in a tissue-preferred manner, more particularly in a pollen preferred manner. Such constructs of the disclosure comprise regulated transcription initiation regions associated with plant developmental regulation. Thus, the compositions of the present disclosure include DNA constructs comprising a nucleotide sequence of interest operably linked to a plant promoter, particularly a pollen preferred promoter sequence, more particularly an *Arabidopsis* pollen promoter sequence. A sequence comprising the *Arabidopsis* pollen promoter region is set forth in SEQ ID NOS: 53, 54, 55 and 56.

TABLE 1

| SEQ ID. | NAME | DESCRIPTION | POLYNUCLEOTIDE/ POLYPEPTIDE (PN/PP) |
|---|---|---|---|
| SEQ ID NO: 1 | AT-NUC1 PRO (AT4G21620) | OVULE TISSUE-PREFERRED PROMOTER | PN |
| SEQ ID NO: 2 | ALT-AT-NUC1 PRO (AT4G21620) | OVULE TISSUE-PREFERRED PROMOTER | PN |
| SEQ ID NO: 3 | AT-CYP86C1 (AT1G24540) | OVULE TISSUE-PREFERRED PROMOTER | PN |
| SEQ ID NO: 4 | ALT-AT-CYP86C1 | OVULE TISSUE-PREFERRED PROMOTER | PN |

TABLE 1-continued

| SEQ ID. | NAME | DESCRIPTION | POLYNUCLEOTIDE/ POLYPEPTIDE (PN/PP) |
|---|---|---|---|
| SEQ ID NO: 5 | AT-PPM1 PRO AT5G49180 | OVULE TISSUE-PREFERRED PROMOTER | PN |
| SEQ ID NO: 6 | AT-EXT PRO AT3G48580 | OVULE TISSUE-PREFERRED PROMOTER | PN |
| SEQ ID NO: 7 | AT-GILT1 PRO AT4G12890 | OVULE TISSUE-PREFERRED PROMOTER | PN |
| SEQ ID NO: 8 | AT-TT2 PRO AT5G35550 | OVULE TISSUE-PREFERRED PROMOTER | PN |
| SEQ ID NO: 9 | AT-SVL3 PRO | OVULE TISSUE-PREFERRED PROMOTER | PN |
| SEQ ID NO: 10 | AT-DD45 PRO | EGG CELL-PREFERRED PROMOTER | PN |
| SEQ ID NO: 11 | ATRKD1 FULL LENGTH CDNA | CDNA OF RKD POLYPEPTIDE | PN |
| SEQ ID NO: 12 | ATRKD1 AMINO ACID NM_101737.1 | RKD POLYPEPTIDE | PP |
| SEQ ID NO: 13 | ATRKD2 (AT1G74480) FULL LENGTH CDNA NM_106108 | CDNA OF RKD POLYPEPTIDE | PN |
| SEQ ID NO: 14 | ATRKD2 (AT1G74480) AMINO ACID | RKD POLYPEPTIDE | PP |
| SEQ ID NO: 15 | ATRKD3 (AT5G66990) FULL LENGTH CDNA NM_126099 | CDNA OF RKD POLYPEPTIDE | PN |
| SEQ ID NO: 16 | ATRKD3 (AT5G66990) AMINO ACID NP_201500.1 | RKD POLYPEPTIDE | PP |
| SEQ ID NO: 17 | ATRKD4 (AT5G53040) FULL LENGTH CDNA | CDNA OF RKD POLYPEPTIDE | PN |
| SEQ ID NO: 18 | ATRKD4 (AT5G53040) AMINO ACID NP_200116.1 | RKD POLYPEPTIDE | PP |
| SEQ ID NO: 19 | EASE PRO | EGG CELL-PREFERRED PROMOTER | PN |
| SEQ ID NO: 20 | AT-DD2 PRO | EGG CELL-PREFERRED PROMOTER | PN |
| SEQ ID NO: 21 | AT-RKD1 PRO | EGG CELL-PREFERRED | PN |
| SEQ ID NO: 22 | AT-RKD2 PRO | EGG CELL-PREFERRED | PN |
| SEQ ID NO: 23 | BA-BARNASE-INT | DNA ENCODING CYTOTOXIC POLYPEPTIDE | PN |
| SEQ ID NO: 24 | DAM METHYLASE | DNA ENCODING CYTOTOXIC POLYPEPTIDE | PN |
| SEQ ID NO: 25 | DMETH N-TERM | OLIGONUCLEOTIDE | PN |
| SEQ ID NO: 26 | INTE-N | OLIGONUCLEOTIDE | PN |
| SEQ ID NO: 27 | INTE-C | OLIGONUCLEOTIDE | PN |
| SEQ ID NO: 28 | DMETH C-TERM | OLIGONUCLEOTIDE | PN |
| SEQ ID NO: 29 | ADP RIBOSYLASE | DNA ENCODING CTYOTOXIC POLYPEPTIDE | PN |
| SEQ ID NO: 30 | FEM2 | EMBRYO SAC-PREFERRED PROMOTER | PN |
| SEQ ID NO: 31 | ATRKD5 AT4G35590; DNA; *ARABIDOPSIS THALIANA* | CDNA OF RKD POLYPEPTIDE | PN |

TABLE 1-continued

| SEQ ID. | NAME | DESCRIPTION | POLYNUCLEOTIDE/ POLYPEPTIDE (PN/PP) |
|---|---|---|---|
| SEQ ID NO: 32 | AT-RKD5; PRT; *ARABIDOPSIS THALIANA* | RKD POLYPEPTIDE | PP |
| SEQ ID NO: 33 | AT1G24540 AT-CP450-1 PRO | OVULE TISSUE-PREFERRED PROMOTER | PN |
| SEQ ID NO: 34 | ZMDD45PRO; DNA; *ZEA MAYS* | PROMOTER | PN |
| SEQ ID NO: 35 | PCO659480 5PRIMELONG; DNA; *ZEA MAYS* | OLIGONUCLEOTIDE | PN |
| SEQ ID NO: 36 | PCO659480 3PRIMELONG; DNA; *ZEA MAYS* | OLIGONUCLEOTIDE | PN |
| SEQ ID NO: 37 | ZSGREEN5PRIME; DNA; *ZOANTHUS* SP | OLIGONUCLEOTIDE | PN |
| SEQ ID NO: 38 | ZSGREEN3PRIME; DNA; *ZOANTHUS* SP | OLIGONUCLEOTIDE | PN |
| SEQ ID NO: 39 | CYAN1 5PRIME; DNA; *ANEMONIA MAJANO* | OLIGONUCLEOTIDE | PN |
| SEQ ID NO: 40 | CYAN1 3PRIME; DNA; *ANEMONIA MAJANO* | OLIGONUCLEOTIDE | PN |
| SEQ ID NO: 41 | AT-DD1 PRO; DNA; *ARABIDOPSIS THALIANA* | PROMOTER | PN |
| SEQ ID NO: 42 | AT-DD31 PRO; DNA; *ARABIDOPSIS THALIANA* | PROMOTER | PN |
| SEQ ID NO: 43 | AT-DD65 PRO; DNA; *ARABIDOPSIS THALIANA* | PROMOTER | PN |
| SEQ ID NO: 44 | *SORGHUM BICOLOR* OVULE SPECIFIC PROMOTER 1 (SB10G008120.1) | PROMOTER-OVULE | PN |
| SEQ ID NO: 45 | PROMOTER RICE OVULE CANDIDATE 1 (OS02G-51090) | PROMOTER-OVULE | PN |
| SEQ ID NO: 46 | AT-RKD2 PRO (AT1G74480) | PROMOTER WITH PROPOSED TETOP SITES. OPTION 1 | PN |
| SEQ ID NO: 47 | AT-RKD2 PRO (AT1G74480) | PROMOTER WITH PROPOSED TETOP SITES. OPTION 2 | PN |
| SEQ ID NO: 48 | AT-RKD2 PRO (AT1G74480) | PROMOTER WITH PROPOSED TETOP SITES. OPTION 3 | PN |
| SEQ ID NO: 49 | BA-BASTAR; DNA; *BACILLUS AMYLOLIQUEFACIENS* | CYTOTOXIC COGNATE REPRESSOR | PN |
| SEQ ID NO: 50 | AT-RKD3 PRO; DNA; *ARABIDOPSIS THALIANA* | PROMOTER | PN |
| SEQ ID NO: 51 | AT-RKD4 PRO; DNA; *ARABIDOPSIS THALIANA* | PROMOTER | PN |
| SEQ ID NO: 52 | AT-RKD5 PRO; DNA; *ARABIDOPSIS THALIANA* | PROMOTER | PN |
| SEQ ID NO: 53 | AT-LAT52LP1 PRO; DNA; *ARABIDOPSIS THALIANA* | PROMOTER | PN |

TABLE 1-continued

| SEQ ID. | NAME | DESCRIPTION | POLYNUCLEOTIDE/ POLYPEPTIDE (PN/PP) |
|---|---|---|---|
| SEQ ID NO: 54 | AT-LAT52LP2 PRO; DNA; *ARABIDOPSIS THALIANA* | PROMOTER | PN |
| SEQ ID NO: 55 | AT-PPG1 PRO; DNA; *ARABIDOPSIS THALIANA* | PROMOTER | PN |
| SEQ ID NO: 56 | AT-PPG2 PRO; DNA; *ARABIDOPSIS THALIANA* | PROMOTER | PN |

Compositions of the disclosure include the nucleotide sequences for the native promoter and fragments and variants thereof. The promoter sequences of the disclosure are useful for expressing sequences. In specific embodiments, the promoter sequences of the disclosure are useful for expressing sequences of interest particularly in a pollen preferred manner. The nucleotide sequences of the disclosure also find use in the construction of expression vectors for subsequent expression of a heterologous nucleotide sequence in a plant of interest or as probes for the isolation of other pollen preferred promoters. In particular, the present disclosure provides for isolated DNA constructs comprising the promoter nucleotide sequence set forth in SEQ ID NO: 53, 54, 55 and 56 operably linked to a nucleotide sequence of interest The disclosure encompasses isolated or substantially purified nucleic acid compositions. An "isolated" or "purified" nucleic acid molecule or biologically active portion thereof is substantially free of other cellular material or culture medium when produced by recombinant techniques or substantially free of chemical precursors or other chemicals when chemically synthesized. An "isolated" nucleic acid is substantially free of sequences (including protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb or 0.1 kb of nucleotide sequences that naturally flank the nucleic acid molecule in genomic DNA of the cell from which the nucleic acid is derived. The promoter sequences of the disclosure may be isolated from the 5' untranslated region flanking their respective transcription initiation sites.

Fragments and variants of the disclosed promoter nucleotide sequences are also encompassed by the present disclosure. In particular, fragments and variants of the promoter sequence of SEQ ID NOS: 53-56 may be used in the DNA constructs of the disclosure. As used herein, the term "fragment" refers to a portion of the nucleic acid sequence. Fragments of a promoter sequence may retain the biological activity of initiating transcription, more particularly driving transcription in a pollen preferred manner. Alternatively, fragments of a nucleotide sequence that are useful as hybridization probes may not necessarily retain biological activity. Fragments of a nucleotide sequence for the promoter region may range from at least about 20 nucleotides, about 50 nucleotides, about 100 nucleotides and up to the full length of SEQ ID NOS: 53-56.

A biologically active portion of a promoter can be prepared by isolating a portion of the promoter sequence of the disclosure, and assessing the promoter activity of the portion. Nucleic acid molecules that are fragments of a promoter nucleotide sequence comprise at least about 16, 50, 75, 100, 150, 200, 250, 300, 350, 400, 450, 500, 550, 600, 650, 700 or 800 nucleotides or up to the number of nucleotides present in a full-length promoter sequence disclosed herein.

As used herein, the term "variants" is intended to mean sequences having substantial similarity with a promoter sequence disclosed herein. A variant comprises a deletion and/or addition of one or more nucleotides at one or more internal sites within the native polynucleotide and/or a substitution of one or more nucleotides at one or more sites in the native polynucleotide. As used herein, a "native" nucleotide sequence comprises a naturally occurring nucleotide sequence. For nucleotide sequences, naturally occurring variants can be identified with the use of well-known molecular biology techniques, such as, for example, with polymerase chain reaction (PCR) and hybridization techniques as outlined herein.

Variant nucleotide sequences also include synthetically derived nucleotide sequences, such as those generated, for example, by using site-directed mutagenesis. Generally, variants of a particular nucleotide sequence of the embodiments will have at least 40%, 50%, 60%, 65%, 70%, 75%, 80%, 85%, 90%, 91%, 92%, 93%, 94%, to 95%, 96%, 97%, 98%, 99% or more sequence identity to that particular nucleotide sequence as determined by sequence alignment programs described elsewhere herein using default parameters. Biologically active variants are also encompassed by the embodiments. Biologically active variants include, for example, the native promoter sequences of the embodiments having one or more nucleotide substitutions, deletions or insertions. Promoter activity may be measured by using techniques such as Northern blot analysis, reporter activity measurements taken from transcriptional fusions, and the like. See, for example, Sambrook, et al., (1989) Molecular Cloning: A Laboratory Manual (2d ed., Cold Spring Harbor Laboratory Press, Cold Spring Harbor, N.Y.), hereinafter "Sambrook," herein incorporated by reference in its entirety. Alternatively, levels of a reporter gene such as green fluorescent protein (GFP) or yellow fluorescent protein (YFP) or the like produced under the control of a promoter fragment or variant can be measured. See, for example, Matz, et al., (1999) *Nature Biotechnology* 17:969-973; U.S. Pat. No. 6,072,050, herein incorporated by reference in its entirety; Nagai, et al., (2002) *Nature Biotechnology* 20(1):87-90. Variant nucleotide sequences also encompass sequences derived from a mutagenic and recombinogenic procedure such as DNA shuffling. With such a procedure, one or more different nucleotide sequences for the promoter can be manipulated to create a new promoter. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer, (1994) *Proc. Natl. Acad. Sci. USA* 91:10747-10751; Stemmer, (1994) *Nature* 370:389 391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291 and U.S. Pat. Nos. 5,605,793 and 5,837,458, herein incorporated by reference in their entirety.

Methods for mutagenesis and nucleotide sequence alterations are well known in the art. See, for example, Kunkel, (1985) *Proc. Natl. Acad. Sci. USA* 82:488-492; Kunkel, et al., (1987) *Methods in Enzymol.* 154:367-382; U.S. Pat. No. 4,873,192; Walker and Gaastra, eds. (1983) Techniques in Molecular Biology (MacMillan Publishing Company, New York) and the references cited therein, herein incorporated by reference in their entirety.

The nucleotide sequences of the disclosure can be used to isolate corresponding sequences from other organisms, particularly other plants, more particularly other dicots. In this manner, methods such as PCR, hybridization and the like can be used to identify such sequences based on their sequence homology to the sequences set forth herein. Sequences isolated based on their sequence identity to the entire sequences set forth herein or to fragments thereof are encompassed by the present disclosure.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in, Sambrook, supra. See also, Innis, et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York), herein incorporated by reference in their entirety. Known methods of PCR include, but are not limited to, methods using paired primers, nested primers, single specific primers, degenerate primers, gene-specific primers, vector-specific primers, partially-mismatched primers and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides and may be labeled with a detectable group such as $^{32}P$ or any other detectable marker. Thus, for example, probes for hybridization can be made by labeling synthetic oligonucleotides based on the promoter sequences of the disclosure. Methods for preparation of probes for hybridization and for construction of genomic libraries are generally known in the art and are disclosed in Sambrook, supra.

For example, the entire promoter sequence disclosed herein, or one or more portions thereof, may be used as a probe capable of specifically hybridizing to corresponding dicot pollen promoter sequences and messenger RNAs. To achieve specific hybridization under a variety of conditions, such probes include sequences that are unique among promoter sequences and are generally at least about 10 nucleotides in length or at least about 20 nucleotides in length.

Such probes may be used to amplify corresponding promoter sequences from a chosen plant by PCR. This technique may be used to isolate additional coding sequences from a desired organism or as a diagnostic assay to determine the presence of coding sequences in an organism. Hybridization techniques include hybridization screening of plated DNA libraries (either plaques or colonies, see, for example, Sambrook, supra).

Hybridization of such sequences may be carried out under stringent conditions. The terms "stringent conditions" or "stringent hybridization conditions" are intended to mean conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C. and a wash in 1 times to 2 times SSC (20 times SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C. and a wash in 0.5 times to 1 times SSC at 55 to 60° C. Exemplary high stringency conditions include hybridization in 50% formamide, 1 M NaCl, 1% SDS at 37° C., and a final wash in 0.1 times SSC at 60 to 65° C. for a duration of at least 30 minutes. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl, (1984) *Anal. Biochem* 138: 267 284: $T_m=81.5°$ C.+16.6 (log M)+0.41(% GC)−0.61(% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching, thus, $T_m$, hybridization, and/or wash conditions can be adjusted to hybridize to sequences of the desired identity. For example, if sequences with 90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3 or 4° C. lower than the $T_m$; moderately stringent conditions can utilize a hybridization and/or wash at 6, 7, 8, 9 or 10° C. lower than the $T_m$; low stringency conditions can utilize a hybridization and/or wash at 11, 12, 13, 14, 15 or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen, (1993) Laboratory Techniques in Biochemistry and Molecular Biology—Hybridization with Nucleic Acid Probes, Part I, Chapter 2 (Elsevier, N.Y.) and Ausubel, et al., eds. (1995) Current Protocols in Molecular Biology, Chapter 2 (Greene Publishing and Wiley-Interscience, New York), herein incorporated by reference in their entirety. See also, Sambrook.

Thus, isolated sequences that have pollen preferred promoter activity and which hybridize under stringent conditions to the promoter sequences disclosed herein or to fragments thereof, are encompassed by the present disclosure.

In general, sequences that have promoter activity and hybridize to the promoter sequences disclosed herein will be at least 40% to 50% homologous, about 60%, 70%, 80%, 85%, 90%, 95% to 98% homologous or more with the disclosed sequences. That is, the sequence similarity of sequences may range, sharing at least about 40% to 50%, about 60% to 70%, and about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity" and (e) "substantial identity".

As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) CABIOS 4:11-17; the algorithm of Smith, et al., (1981) Adv. Appl. Math. 2:482; the algorithm of Needleman and Wunsch, (1970) J. Mol. Biol. 48:443-453; the algorithm of Pearson and Lipman, (1988) Proc. Natl. Acad. Sci. 85:2444-2448; the algorithm of Karlin and Altschul, (1990) Proc. Natl. Acad. Sci. USA 872:264, modified as in Karlin and Altschul, (1993) Proc. Natl. Acad. Sci. USA 90:5873-5877, herein incorporated by reference in their entirety.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA and TFASTA in the GCG Wisconsin Genetics Software Package®, Version 10 (available from Accelrys Inc., 9685 Scranton Road, San Diego, Calif., USA). Alignments using these programs can be performed using the default parameters. The CLUSTAL program is well described by Higgins, et al., (1988) Gene 73:237-244 (1988); Higgins, et al., (1989) CABIOS 5:151-153; Corpet, et al., (1988) Nucleic Acids Res. 16:10881-90; Huang, et al., (1992) CABIOS 8:155-65 and Pearson, et al., (1994) Meth. Mol. Biol. 24:307-331, herein incorporated by reference in their entirety. The ALIGN program is based on the algorithm of Myers and Miller, (1988) supra. A PAM120 weight residue table, a gap length penalty of 12, and a gap penalty of 4 can be used with the ALIGN program when comparing amino acid sequences. The BLAST programs of Altschul, et al., (1990) J. Mol. Biol. 215:403, herein incorporated by reference in its entirety, are based on the algorithm of Karlin and Altschul, (1990) supra. BLAST nucleotide searches can be performed with the BLASTN program, score=100, word length=12, to obtain nucleotide sequences homologous to a nucleotide sequence encoding a protein of the disclosure. BLAST protein searches can be performed with the BLASTX program, score=50, word length=3, to obtain amino acid sequences homologous to a protein or polypeptide of the disclosure. To obtain gapped alignments for comparison purposes, Gapped BLAST (in BLAST 2.0) can be utilized as described in Altschul, et al., (1997) Nucleic Acids Res. 25:3389, herein incorporated by reference in its entirety. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, the web site for the National Center for Biotechnology Information on the World Wide Web at ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. As used herein, "equivalent program" is any sequence comparison program that, for any two sequences in question, generates an alignment having identical nucleotide or amino acid residue matches and an identical percent sequence identity when compared to the corresponding alignment generated by GAP Version 10.

The GAP program uses the algorithm of Needleman and Wunsch, supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package® for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package® is BLOSUM62 (see, Henikoff and Henikoff, (1989) *Proc. Natl. Acad. Sci. USA* 89:10915, herein incorporated by reference in its entirety).

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of one and a non-conservative substitution is given a score of zero, a conservative substitution is given a score between zero and one. The scoring of conservative substitutions is calculated, e.g., as implemented in the program PC/GENE (Intelligenetics, Mountain View, Calif.).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, optimally at least 80%, more optimally at least 90% and most optimally at least 95%, compared to a reference sequence using an alignment program using standard parameters. One of skill in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, 70%, 80%, 90% and at least 95%.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The promoter sequence disclosed herein, as well as variants and fragments thereof, are useful for genetic engineering of plants, e.g., for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part or plant the genotype of which has been altered by the presence of heterologous nucleic acid including those transgenics initially so altered as well as those created by sexual crosses or asexual propagation from the initial transgenic.

A transgenic "event" is produced by transformation of plant cells with a heterologous DNA construct, including a nucleic acid expression cassette that comprises a transgene of interest, the regeneration of a population of plants resulting from the insertion of the transgene into the genome of the plant and selection of a particular plant characterized by insertion into a particular genome location. An event is characterized phenotypically by the expression of the transgene. At the genetic level, an event is part of the genetic makeup of a plant. The term "event" also refers to progeny produced by a sexual cross between the transformant and another plant wherein the progeny include the heterologous DNA.

As used herein, the term plant includes whole plants, plant organs (e.g., leaves, stems, roots, etc.), plant cells, plant protoplasts, plant cell tissue cultures from which plants can be regenerated, plant calli, plant clumps and plant cells that are intact in plants or parts of plants such as embryos, pollen, developing microspores, seeds, leaves, flowers, branches, fruit, kernels, ears, cobs, husks, stalks, roots, root tips, anthers and the like. Grain is intended to mean the mature seed produced by commercial growers for purposes other than growing or reproducing the species. Progeny, variants and mutants of the regenerated plants are also included within the scope of the disclosure, provided that these parts comprise the introduced polynucleotides.

The present disclosure may be used for transformation of any plant species, including, but not limited to, monocots and dicots. Examples of plant species include corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*) and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*) and chrysanthemum.

Conifers that may be employed in practicing the present disclosure include, for example, pines such as loblolly pine (*Pinus taeda*), slash pine (*Pinus elliotii*), ponderosa pine (*Pinus ponderosa*), lodgepole pine (*Pinus contorta*) and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*) and cedars such as Western red cedar (*Thuja plicata*) and Alaska yellow-cedar (*Chamaecyparis nootkatensis*). In specific embodiments, plants of the present disclosure are crop plants (for example, corn, alfalfa, sunflower, *Brassica*, soybean, cotton, safflower, peanut, *sorghum*, wheat, millet, tobacco, etc.). In other embodiments, corn and soybean plants are optimal, and in yet other embodiments corn plants are optimal.

Other plants of interest include grain plants that provide seeds of interest, oil-seed plants and leguminous plants. Seeds of interest include grain seeds, such as corn, wheat, barley, rice, *sorghum*, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

Heterologous coding sequences expressed by a promoter of the disclosure may be used for varying the phenotype of a plant. Various changes in phenotype are of interest including modifying expression of a gene in a plant, altering a plant's pathogen or insect defense mechanism, changing a plant's reproductive capacities, preventing paternal transgene transmission, increasing a plant's tolerance to herbicides, altering plant development to respond to environmental stress, modulating the plant's response to salt, temperature (hot and cold), drought and the like. These results can be achieved by the expression of a heterologous nucleotide sequence of interest comprising an appropriate gene product. In specific embodiments, the heterologous nucleotide sequence of interest is an endogenous plant sequence whose expression level is increased in the plant or plant part. Results can be achieved by providing for altered expression of one or more endogenous gene products, particularly hormones, receptors, signaling molecules, enzymes, transporters or cofactors or by affecting nutrient uptake in the plant. Tissue-preferred expression as provided by the promoter can target the alteration in expression to plant parts and/or growth stages of particular interest, such as developing microspores, particularly the pollen. These changes result in a change in phenotype of the transformed plant General categories of nucleotide sequences of interest for the present disclosure include, for example, those genes involved in information, such as zinc fingers, those involved in communication, such as kinases and those involved in housekeeping, such as heat shock proteins. More specific categories of transgenes, for example, include genes encoding important traits for agronomics, insect resistance, disease resistance, herbicide resistance, environmental stress resistance (altered tolerance to cold, salt, drought, etc) and grain characteristics. Still other categories of transgenes include genes for inducing expression of exogenous products such as enzymes, cofactors, and hormones from plants and other eukaryotes as well as prokaryotic organisms. It is recognized that any gene of interest can be operably linked to the promoter of the disclosure and expressed in the plant.

Agronomically important traits that affect quality of grain, such as levels and types of oils, saturated and unsaturated, quality and quantity of essential amino acids, levels of cellulose, starch and protein content can be genetically altered using the methods of the embodiments. Modifications to grain traits include, but are not limited to, increasing content of oleic acid, saturated and unsaturated oils, increasing levels of lysine and sulfur, providing essential amino acids, and modifying starch. Hordothionin protein modifications in corn are described in U.S. Pat. Nos. 5,990,389; 5,885,801; 5,885, 802 and 5,703,049; herein incorporated by reference in their entirety. Another example is lysine and/or sulfur rich seed protein encoded by the soybean 2S albumin described in U.S. Pat. No. 5,850,016, filed Mar. 20, 1996 and the chymotrypsin inhibitor from barley, Williamson, et al., (1987) *Eur. J. Biochem* 165:99-106, the disclosures of which are herein incorporated by reference in their entirety.

Insect resistance genes may encode resistance to pests that have great yield drag such as rootworm, cutworm, European corn borer and the like. Such genes include, for example, *Bacillus thuringiensis* toxic protein genes, U.S. Pat. Nos. 5,366,892; 5,747,450; 5,736,514; 5,723,756; 5,593,881 and Geiser, et al., (1986) *Gene* 48:109, the disclosures of which are herein incorporated by reference in their entirety. Genes encoding disease resistance traits include, for example, detoxification genes, such as those which detoxify fumonisin (U.S. Pat. No. 5,792,931); avirulence (avr) and disease resistance (R) genes (Jones, et al., (1994) *Science* 266:789; Martin, et al., (1993) *Science* 262:1432; and Mindrinos, et al., (1994) *Cell* 78:1089), herein incorporated by reference in their entirety.

Herbicide resistance traits may include genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), genes coding for resistance to glyphosate (e.g., the EPSPS gene and the GAT gene; see, for example, US Patent Application Publication Number 2004/0082770 and WO 2003/092360, herein incorporated by reference in their entirety) or other such genes known in the art. The bar gene encodes resistance to the herbicide basta, the nptII gene encodes resistance to the antibiotics kanamycin and geneticin and the ALS-gene mutants encode resistance to the herbicide chlorsulfuron.

Glyphosate resistance is imparted by mutant 5-enolpyruvl-3-phosphikimate synthase (EPSP) and aroA genes. See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and international publications WO 1997/04103; WO 1997/04114; WO 2000/66746; WO 2001/66704; WO 2000/66747 and WO 2000/66748, which are incorporated herein by reference in their entirety. Glyphosate resistance is also imparted to plants that express a gene that encodes a glyphosate oxido-reductase enzyme as described more fully in U.S. Pat. Nos. 5,776,760 and 5,463,175, which are incorporated herein by reference in their entirety. In addition glyphosate resistance can be imparted to plants by the over expression of genes encoding glyphosate N-acetyltransferase. See, for example, U.S. patent application Ser. Nos. 11/405,845 and 10/427,692, herein incorporated by reference in their entirety.

Sterility genes can also be encoded in a DNA construct and provide an alternative to physical detasseling. Examples of genes used in such ways include male tissue-preferred genes and genes with male sterility phenotypes such as QM, described in U.S. Pat. No. 5,583,210, herein incorporated by reference in its entirety. Other genes include kinases and those encoding compounds toxic to either male or female gametophytic development.

Commercial traits can also be encoded on a gene or genes that could increase for example, starch for ethanol production or provide expression of proteins. Another important commercial use of transformed plants is the production of polymers and bioplastics such as described in U.S. Pat. No. 5,602,321; herein incorporated by reference in its entirety. Genes such as β-Ketothiolase, PHBase (polyhydroxybutyrate synthase), and acetoacetyl-CoA reductase (see, Schubert, et al., (1988) *J. Bacteriol.* 170:5837-5847, herein incorporated by reference in its entirety) facilitate expression of polyhydroxyalkanoates (PHAs).

Exogenous products include plant enzymes and products as well as those from other sources including prokaryotes and other eukaryotes. Such products include enzymes, cofactors, hormones and the like.

Examples of other applicable genes and their associated phenotype include the gene which encodes viral coat protein and/or RNA, or other viral or plant genes that confer viral resistance; genes that confer fungal resistance; genes that promote yield improvement and genes that provide for resistance to stress, such as cold, dehydration resulting from drought, heat and salinity, toxic metal or trace elements or the like.

By way of illustration, without intending to be limiting, the following is a list of other examples of the types of genes which can be used in connection with the regulatory sequences of the disclosure.

1. Transgenes that Confer Resistance to Insects or Disease and that Encode:

(A) Plant disease resistance genes. Plant defenses are often activated by specific interaction between the product of a disease resistance gene (R) in the plant and the product of a corresponding avirulence (Avr) gene in the pathogen. A plant variety can be transformed with cloned resistance gene to engineer plants that are resistant to specific pathogen strains. See, for example Jones, et al., (1994) *Science* 266:789 (cloning of the tomato Cf-9 gene for resistance to *Cladosporium fulvum*); Martin, et al., (1993) *Science* 262:1432 (tomato Pto gene for resistance to *Pseudomonas syringae* pv. tomato encodes a protein kinase); Mindrinos, et al., (1994) *Cell* 78:1089 (*Arabidopsis* RSP2 gene for resistance to *Pseudomonas syringae*); McDowell and Woffenden, (2003) *Trends Biotechnol.* 21(4):178-83 and Toyoda, et al., (2002) *Transgenic Res.* 11(6):567-82, herein incorporated by reference in their entirety. A plant resistant to a disease is one that is more resistant to a pathogen as compared to the wild type plant.

(B) A *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC Accession Numbers 40098, 67136, 31995 and 31998. Other examples of *Bacillus thuringiensis* transgenes being genetically engineered are given in the following patents and patent applications and hereby are incorporated by reference for this purpose: U.S. Pat. Nos. 5,188,960; 5,689,052; 5,880,275; WO 1991/14778; WO 1999/31248; WO 2001/12731; WO 1999/24581; WO 1997/40162 and U.S. application Ser. Nos. 10/032,717; 10/414,637 and 10/606,320, herein incorporated by reference in their entirety.

(C) An insect-specific hormone or pheromone such as an ecdysteroid and juvenile hormone, a variant thereof, a mimetic based thereon or an antagonist or agonist thereof. See, for example, the disclosure by Hammock, et al., (1990) *Nature* 344:458, of baculovirus expression of cloned juvenile hormone esterase, an inactivator of juvenile hormone, herein incorporated by reference in its entirety.

(D) An insect-specific peptide which, upon expression, disrupts the physiology of the affected pest. For example, see the disclosures of Regan, (1994) *J. Biol. Chem.* 269:9 (expression cloning yields DNA coding for insect diuretic hormone receptor); Pratt, et al., (1989) *Biochem. Biophys. Res. Comm.* 163:1243 (an allostatin is identified in *Diploptera puntata*); Chattopadhyay, et al., (2004) *Critical Reviews in Microbiology* 30(1):33-54; Zjawiony, (2004) *J Nat Prod*

67(2):300-310; Carlini and Grossi-de-Sa, (2002) *Toxicon* 40(11):1515-1539; Ussuf, et al., (2001) *Curr Sci.* 80(7):847-853 and Vasconcelos and Oliveira, (2004) *Toxicon* 44(4):385-403, herein incorporated by reference in their entirety. See also, U.S. Pat. No. 5,266,317 to Tomalski, et al., who disclose genes encoding insect-specific toxins, herein incorporated by reference in its entirety.

(E) An enzyme responsible for a hyperaccumulation of a monterpene, a sesquiterpene, a steroid, hydroxamic acid, a phenylpropanoid derivative or another non-protein molecule with insecticidal activity.

(F) An enzyme involved in the modification, including the post-translational modification, of a biologically active molecule; for example, a glycolytic enzyme, a proteolytic enzyme, a lipolytic enzyme, a nuclease, a cyclase, a transaminase, an esterase, a hydrolase, a phosphatase, a kinase, a phosphorylase, a polymerase, an elastase, a chitinase and a glucanase, whether natural or synthetic. See, PCT Application Number WO 1993/02197 in the name of Scott, et al., which discloses the nucleotide sequence of a callase gene, herein incorporated by reference in its entirety. DNA molecules which contain chitinase-encoding sequences can be obtained, for example, from the ATCC under Accession Numbers 39637 and 67152. See also, Kramer, et al., (1993) *Insect Biochem. Molec. Biol.* 23:691, who teach the nucleotide sequence of a cDNA encoding tobacco hookworm chitinase, and Kawalleck, et al., (1993) *Plant Molec. Biol.* 21:673, who provide the nucleotide sequence of the parsley ubi4-2 polyubiquitin gene, U.S. patent application Ser. Nos. 10/389,432, 10/692,367 and U.S. Pat. No. 6,563,020, herein incorporated by reference in their entirety.

(G) A molecule that stimulates signal transduction. For example, see the disclosure by Botella, et al., (1994) *Plant Molec. Biol.* 24:757, of nucleotide sequences for mung bean calmodulin cDNA clones and Griess, et al., (1994) *Plant Physiol.* 104:1467, who provide the nucleotide sequence of a maize calmodulin cDNA clone, herein incorporated by reference in their entirety.

(H) A hydrophobic moment peptide. See, PCT Application Number WO 1995/16776 and U.S. Pat. No. 5,580,852 (disclosure of peptide derivatives of Tachyplesin which inhibit fungal plant pathogens) and PCT Application Number WO 1995/18855 and U.S. Pat. No. 5,607,914) (teaches synthetic antimicrobial peptides that confer disease resistance), herein incorporated by reference in their entirety.

(I) A membrane permease, a channel former or a channel blocker. For example, see the disclosure by Jaynes, et al., (1993) *Plant Sci.* 89:43, of heterologous expression of a cecropin-beta lytic peptide analog to render transgenic tobacco plants resistant to *Pseudomonas solanacearum*, herein incorporated by reference in its entirety.

(J) A viral-invasive protein or a complex toxin derived therefrom. For example, the accumulation of viral coat proteins in transformed plant cells imparts resistance to viral infection and/or disease development effected by the virus from which the coat protein gene is derived, as well as by related viruses. See, Beachy, et al., (1990) *Ann. Rev. Phytopathol.* 28:451, herein incorporated by reference in its entirety. Coat protein-mediated resistance has been conferred upon transformed plants against alfalfa mosaic virus, cucumber mosaic virus, tobacco streak virus, potato virus X, potato virus Y, tobacco etch virus, tobacco rattle virus and tobacco mosaic virus. Id.

(K) An insect-specific antibody or an immunotoxin derived therefrom. Thus, an antibody targeted to a critical metabolic function in the insect gut would inactivate an affected enzyme, killing the insect. Cf. Taylor, et al., Abstract #497, SEVENTH INT'L SYMPOSIUM ON MOLECULAR PLANT-MICROBE INTERACTIONS (Edinburgh, Scotland, 1994) (enzymatic inactivation in transgenic tobacco via production of single-chain antibody fragments), herein incorporated by reference in its entirety.

(L) A virus-specific antibody. See, for example, Tavladoraki, et al., (1993) *Nature* 366:469, who show that transgenic plants expressing recombinant antibody genes are protected from virus attack, herein incorporated by reference in its entirety.

(M) A developmental-arrestive protein produced in nature by a pathogen or a parasite. Thus, fungal endo alpha-1,4-D-polygalacturonases facilitate fungal colonization and plant nutrient release by solubilizing plant cell wall homo-alpha-1,4-D-galacturonase. See, Lamb, et al., (1992) *Bio/Technology* 10:1436, herein incorporated by reference in its entirety. The cloning and characterization of a gene which encodes a bean endopolygalacturonase-inhibiting protein is described by Toubart, et al., (1992) *Plant J.* 2:367, herein incorporated by reference in its entirety.

(N) A developmental-arrestive protein produced in nature by a plant. For example, Logemann, et al., (1992) *Bio/Technology* 10:305, herein incorporated by reference in its entirety, have shown that transgenic plants expressing the barley ribosome-inactivating gene have an increased resistance to fungal disease.

(O) Genes involved in the Systemic Acquired Resistance (SAR) Response and/or the pathogenesis related genes. Briggs, (1995) *Current Biology* 5(2):128-131, Pieterse and Van Loon, (2004) *Curr. Opin. Plant Bio.* 7(4):456-64 and Somssich, (2003) *Cell* 113(7):815-6, herein incorporated by reference in their entirety.

(P) Antifungal genes (Cornelissen and Melchers, (1993) *Pl. Physiol.* 101:709-712 and Parijs, et al., (1991) *Planta* 183:258-264 and Bushnell, et al., (1998) *Can. J. of Plant Path.* 20(2):137-149. Also see, U.S. patent application Ser. No. 09/950,933, herein incorporated by reference in their entirety.

(Q) Detoxification genes, such as for fumonisin, beauvericin, moniliformin and zearalenone and their structurally related derivatives. For example, see, U.S. Pat. No. 5,792,931, herein incorporated by reference in its entirety.

(R) Cystatin and cysteine proteinase inhibitors. See, U.S. patent application Ser. No. 10/947,979, herein incorporated by reference in its entirety.

(S) Defensin genes. See, WO 2003/000863 and U.S. patent application Ser. No. 10/178,213, herein incorporated by reference in their entirety.

(T) Genes conferring resistance to nematodes. See, WO 2003/033651 and Urwin, et. al., (1998) *Planta* 204:472-479, Williamson (1999) *Curr Opin Plant Bio.* 2(4):327-31, herein incorporated by reference in their entirety.

(U) Genes such as rcg1 conferring resistance to Anthracnose stalk rot, which is caused by the fungus *Colletotrichum graminiola*. See, Jung, et al., (1994) *Theor. Appl. Genet.* 89:413-418, as well as, U.S. Provisional Patent Application No. 60/675,664, herein incorporated by reference in their entirety.

(V) Cytotoxins such as ADP Ribosylase, BA-BARNASE-INT or DMETH which when expressed in the pollen prevent paternal transgene transmission to the next generation.

2. Transgenes that Confer Resistance to a Herbicide, for Example:

(A) A herbicide that inhibits the growing point or meristem, such as an imidazolinone or a sulfonylurea. Exemplary genes in this category code for mutant ALS and AHAS enzyme as described, for example, by Lee, et al., (1988)

EMBO J. 7:1241 and Miki, et al., (1990) *Theor. Appl. Genet.* 80:449, respectively. See also, U.S. Pat. Nos. 5,605,011; 5,013,659; 5,141,870; 5,767,361; 5,731,180; 5,304,732; 4,761,373; 5,331,107; 5,928,937 and 5,378,824 and international publication WO 1996/33270, which are incorporated herein by reference in their entirety.

(B) Glyphosate (resistance imparted by mutant 5-enolpyruvl-3-phosphikimate synthase (EPSP) and aroA genes, respectively) and other phosphono compounds such as glufosinate (phosphinothricin acetyl transferase (PAT) and *Streptomyces hygroscopicus* phosphinothricin acetyl transferase (bar) genes) and pyridinoxy or phenoxy proprionic acids and cyclohexones (ACCase inhibitor-encoding genes). See, for example, U.S. Pat. No. 4,940,835 to Shah, et al., which discloses the nucleotide sequence of a form of EPSPS which can confer glyphosate resistance. U.S. Pat. No. 5,627,061 to Barry, et al., also describes genes encoding EPSPS enzymes. See also, U.S. Pat. Nos. 6,566,587; 6,338,961; 6,248,876 B1; 6,040,497; 5,804,425; 5,633,435; 5,145,783; 4,971,908; 5,312,910; 5,188,642; 4,940,835; 5,866,775; 6,225,114 B1; 6,130,366; 5,310,667; 4,535,060; 4,769,061; 5,633,448; 5,510,471; Re. 36,449; RE 37,287 E and 5,491,288 and international publications EP 1173580; WO 2001/66704; EP 1173581 and EP 1173582, which are incorporated herein by reference in their entirety. Glyphosate resistance is also imparted to plants that express a gene that encodes a glyphosate oxido-reductase enzyme as described more fully in U.S. Pat. Nos. 5,776,760 and 5,463,175, which are incorporated herein by reference in their entirety. In addition glyphosate resistance can be imparted to plants by the over expression of genes encoding glyphosate N-acetyltransferase. See, for example, U.S. patent application Ser. Nos. 11/405,845 and 10/427,692 and PCT Application Number US01/46227, herein incorporated by reference in their entirety. A DNA molecule encoding a mutant aroA gene can be obtained under ATCC Accession Number 39256 and the nucleotide sequence of the mutant gene is disclosed in U.S. Pat. No. 4,769,061 to Comai, herein incorporated by reference in its entirety. EP Patent Application Number 0 333 033 to Kumada, et al., and U.S. Pat. No. 4,975,374 to Goodman, et al., disclose nucleotide sequences of glutamine synthetase genes which confer resistance to herbicides such as L-phosphinothricin, herein incorporated by reference in their entirety. The nucleotide sequence of a phosphinothricin-acetyl-transferase gene is provided in EP Patent Numbers 0 242 246 and 0 242 236 to Leemans, et al., De Greef, et al., (1989) *Bio/Technology* 7:61 which describe the production of transgenic plants that express chimeric bar genes coding for phosphinothricin acetyl transferase activity, herein incorporated by reference in their entirety. See also, U.S. Pat. Nos. 5,969,213; 5,489,520; 5,550,318; 5,874,265; 5,919,675; 5,561,236; 5,648,477; 5,646,024; 6,177,616 B1 and 5,879,903, herein incorporated by reference in their entirety. Exemplary genes conferring resistance to phenoxy proprionic acids and cyclohexones, such as sethoxydim and haloxyfop, are the Acc1-S1, Acc1-S2 and Acc1-S3 genes described by Marshall, et al., (1992) *Theor. Appl. Genet.* 83:435, herein incorporated by reference in its entirety.

(C) A herbicide that inhibits photosynthesis, such as a triazine (psbA and gs+ genes) and a benzonitrile (nitrilase gene). Przibilla, et al., (1991) *Plant Cell* 3:169, herein incorporated by reference in its entirety, describe the transformation of *Chlamydomonas* with plasmids encoding mutant psbA genes. Nucleotide sequences for nitrilase genes are disclosed in U.S. Pat. No. 4,810,648 to Stalker, herein incorporated by reference in its entirety, and DNA molecules containing these genes are available under ATCC Accession Numbers 53435, 67441 and 67442. Cloning and expression of DNA coding for a glutathione S-transferase is described by Hayes, et al., (1992) *Biochem. J.* 285:173, herein incorporated by reference in its entirety.

(D) Acetohydroxy acid synthase, which has been found to make plants that express this enzyme resistant to multiple types of herbicides, has been introduced into a variety of plants (see, e.g., Hattori, et al., (1995) *Mol Gen Genet* 246: 419, herein incorporated by reference in its entirety). Other genes that confer resistance to herbicides include: a gene encoding a chimeric protein of rat cytochrome P4507A1 and yeast NADPH-cytochrome P450 oxidoreductase (Shiota, et al., (1994) *Plant Physiol.* 106(1):17-23), genes for glutathione reductase and superoxide dismutase (Aono, et al., (1995) *Plant Cell Physiol* 36:1687 and genes for various phosphotransferases (Datta, et al., (1992) *Plant Mol Biol* 20:619), herein incorporated by reference in their entirety.

(E) Protoporphyrinogen oxidase (protox) is necessary for the production of chlorophyll, which is necessary for all plant survival. The protox enzyme serves as the target for a variety of herbicidal compounds. These herbicides also inhibit growth of all the different species of plants present, causing their total destruction. The development of plants containing altered protox activity which are resistant to these herbicides are described in U.S. Pat. Nos. 6,288,306 B1; 6,282,837 B1 and 5,767,373; and international publication number WO 2001/12825, herein incorporated by reference in their entirety.

3. Transgenes that Confer or Contribute to an Altered Grain Characteristic, such as:

(A) Altered fatty acids, for example, by
  (1) Down-regulation of stearoyl-ACP desaturase to increase stearic acid content of the plant. See, Knultzon, et al., (1992) *Proc. Natl. Acad. Sci. USA* 89:2624 and WO 1999/64579 (Genes for Desaturases to Alter Lipid Profiles in Corn), herein incorporated by reference in their entirety,
  (2) Elevating oleic acid via FAD-2 gene modification and/or decreasing linolenic acid via FAD-3 gene modification (see, U.S. Pat. Nos. 6,063,947; 6,323,392; 6,372,965 and WO 1993/11245, herein incorporated by reference in their entirety),
  (3) Altering conjugated linolenic or linoleic acid content, such as in WO 2001/12800, herein incorporated by reference in its entirety,
  (4) Altering LEC1, AGP, Dek1, Superal1, mi1ps, various Ipa genes such as Ipa1, Ipa3, hpt or hggt. For example, see, WO 2002/42424, WO 1998/22604, WO 2003/011015, U.S. Pat. No. 6,423,886, U.S. Pat. No. 6,197,561, U.S. Pat. No. 6,825,397, US Patent Application Publication Numbers 2003/0079247, 2003/0204870, WO 2002/057439, WO 2003/011015 and Rivera-Madrid, et al., (1995) *Proc. Natl. Acad. Sci.* 92:5620-5624, herein incorporated by reference in their entirety.

(B) Altered phosphorus content, for example, by the
  (1) Introduction of a phytase-encoding gene would enhance breakdown of phytate, adding more free phosphate to the transformed plant. For example, see, Van Hartingsveldt, et al., (1993) *Gene* 127:87, for a disclosure of the nucleotide sequence of an *Aspergillus niger* phytase gene, herein incorporated by reference in its entirety.
  (2) Up-regulation of a gene that reduces phytate content. In maize, this, for example, could be accomplished, by cloning and then re-introducing DNA associated with one or more of the alleles, such as the LPA alleles, identified in maize mutants characterized by low levels of phytic acid, such as in Raboy, et al., (1990) *Maydica* 35:383 and/or by altering inositol kinase activity as in WO 2002/059324, US Patent Application Publication Number 2003/0009011, WO 2003/027243, US Patent Application Publication Number 2003/0079247, WO 1999/05298, U.S. Pat. No. 6,197,561, U.S. Pat. No. 6,291,224, U.S. Pat. No. 6,391,348, WO 2002/059324, US Patent Application Publication Number 2003/0079247, WO 1998/45448, WO 1999/55882, WO 2001/04147, herein incorporated by reference in their entirety.

(C) Altered carbohydrates effected, for example, by altering a gene for an enzyme that affects the branching pattern of starch or a gene altering thioredoxin such as NTR and/or TRX (see, U.S. Pat. No. 6,531,648, which is incorporated by reference in its entirety) and/or a gamma zein knock out or mutant such as cs27 or TUSC27 or en27 (see, U.S. Pat. No. 6,858,778 and US Patent Application Publication Numbers 2005/0160488 and 2005/0204418; which are incorporated by reference in its entirety). See, Shiroza, et al., (1988) *J. Bacteriol.* 170:810 (nucleotide sequence of *Streptococcus mutans* fructosyltransferase gene), Steinmetz, et al., (1985) *Mol. Gen. Genet.* 200:220 (nucleotide sequence of *Bacillus subtilis* levansucrase gene), Pen, et al., (1992) *Bio/Technology* 10:292 (production of transgenic plants that express *Bacillus licheniformis* alpha-amylase), Elliot, et al., (1993) *Plant Molec. Biol.* 21:515 (nucleotide sequences of tomato invertase genes), Søgaard, et al., (1993) *J. Biol. Chem.* 268:22480 (site-directed mutagenesis of barley alpha-amylase gene) and Fisher, et al., (1993) *Plant Physiol.* 102:1045 (maize endosperm starch branching enzyme II), WO 1999/10498 (improved digestibility and/or starch extraction through modification of UDP-D-xylose 4-epimerase, Fragile 1 and 2, Ref1, HCHL, C4H), U.S. Pat. No. 6,232,529 (method of producing high oil seed by modification of starch levels (AGP)), herein incorporated by reference in their entirety. The fatty acid modification genes mentioned above may also be used to affect starch content and/or composition through the interrelationship of the starch and oil pathways.

(D) Altered antioxidant content or composition, such as alteration of tocopherol or tocotrienols. For example, see U.S. Pat. No. 6,787,683, US Patent Application Publication Number 2004/0034886 and WO 2000/68393 involving the manipulation of antioxidant levels through alteration of a phytl prenyl transferase (ppt), WO 2003/082899 through alteration of a homogentisate geranyl geranyl transferase (hggt), herein incorporated by reference in their entirety.

(E) Altered essential seed amino acids. For example, see U.S. Pat. No. 6,127,600 (method of increasing accumulation of essential amino acids in seeds), U.S. Pat. No. 6,080,913 (binary methods of increasing accumulation of essential amino acids in seeds), U.S. Pat. No. 5,990,389 (high lysine), WO 1999/40209 (alteration of amino acid compositions in seeds), WO 1999/29882 (methods for altering amino acid content of proteins), U.S. Pat. No. 5,850,016 (alteration of amino acid compositions in seeds), WO 1998/20133 (proteins with enhanced levels of essential amino acids), U.S. Pat. No. 5,885,802 (high methionine), U.S. Pat. No. 5,885,801 (high threonine), U.S. Pat. No. 6,664,445 (plant amino acid biosynthetic enzymes), U.S. Pat. No. 6,459,019 (increased lysine and threonine), U.S. Pat. No. 6,441,274 (plant tryptophan synthase beta subunit), U.S. Pat. No. 6,346,403 (methionine metabolic enzymes), U.S. Pat. No. 5,939,599 (high sulfur), U.S. Pat. No. 5,912,414 (increased methionine), WO 1998/56935 (plant amino acid biosynthetic enzymes), WO98/45458 (engineered seed protein having higher percentage of essential amino acids), WO 1998/42831 (increased lysine), U.S. Pat. No. 5,633,436 (increasing sulfur amino acid content), U.S. Pat. No. 5,559,223 (synthetic storage proteins with defined structure containing programmable levels of essential amino acids for improvement of the nutritional value of plants), WO 1996/01905 (increased threonine), WO 1995/15392 (increased lysine), US Patent Application Publication Number 2003/0163838, US Patent Application Publication Number 2003/0150014, US Patent Application Publication Number 2004/0068767, U.S. Pat. No. 6,803,498, WO 2001/79516, and WO 2000/09706 (Ces A: cellulose synthase), U.S. Pat. No. 6,194,638 (hemicellulose), U.S. Pat. No. 6,399,859 and US Patent Application Publication Number 2004/0025203 (UDPGdH), U.S. Pat. No. 6,194,638 (RGP), herein incorporated by reference in their entirety.

4. Genes that Control Male-Sterility

There are several methods of conferring genetic male sterility available, such as multiple mutant genes at separate locations within the genome that confer male sterility, as disclosed in U.S. Pat. Nos. 4,654,465 and 4,727,219 to Brar, et al., and chromosomal translocations as described by Patterson in U.S. Pat. Nos. 3,861,709 and 3,710,511, herein incorporated by reference in their entirety. In addition to these methods, Albertsen, et al., U.S. Pat. No. 5,432,068, herein incorporated by reference in its entirety, describe a system of nuclear male sterility which includes: identifying a gene which is critical to male fertility; silencing this native gene which is critical to male fertility; removing the native promoter from the essential male fertility gene and replacing it with an inducible promoter; inserting this genetically engineered gene back into the plant and thus creating a plant that is male sterile because the inducible promoter is not "on" resulting in the male fertility gene not being transcribed. Fertility is restored by inducing, or turning "on", the promoter, which in turn allows the gene conferring male fertility to be transcribed.

(A) Introduction of a deacetylase gene under the control of a tapetum-specific promoter and with the application of the chemical N-Ac-PPT (WO 2001/29237, herein incorporated by reference in its entirety).

(B) Introduction of various stamen-specific promoters (WO 1992/13956, WO 1992/13957, herein incorporated by reference in their entirety).

(C) Introduction of the barnase and the barstar gene (Paul, et al., (1992) *Plant Mol. Biol.* 19:611-622, herein incorporated by reference in its entirety).

For additional examples of nuclear male and female sterility systems and genes, see also, U.S. Pat. Nos. 5,859,341; 6,297,426; 5,478,369; 5,824,524; 5,850,014 and 6,265,640, all of which are hereby incorporated by reference in their entirety.

5. Genes that Create a Site for Site Specific DNA Integration

This includes the introduction of FRT sites that may be used in the FLP/FRT system and/or Lox sites that may be used in the Cre/Loxp system. For example, see Lyznik, et al., (2003) *Plant Cell Rep* 21:925-932 and WO 1999/25821, which are hereby incorporated by reference in their entirety. Other systems that may be used include the Gin recombinase of phage Mu (Maeser, et al., 1991; Vicki Chandler, *The Maize Handbook* ch. 118 (Springer-Verlag 1994), the Pin recombinase of *E. coli* (Enomoto, et al., 1983) and the R/RS system of the pSR1 plasmid (Araki, et al., 1992), herein incorporated by reference in their entirety.

6. Genes that affect abiotic stress resistance (including but not limited to flowering, ear and seed development, enhancement of nitrogen utilization efficiency, altered nitrogen responsiveness, drought resistance or tolerance, cold resistance or tolerance, and salt resistance or tolerance) and increased yield under stress. For example, see, WO 2000/73475 where water use efficiency is altered through alteration of malate; U.S. Pat. No. 5,892,009, U.S. Pat. No. 5,965,705, U.S. Pat. No. 5,929, 305, U.S. Pat. No. 5,891,859, U.S. Pat. No. 6,417,428, U.S. Pat. No. 6,664,446, U.S. Pat. No. 6,706,866, U.S. Pat. No. 6,717,034, WO 2000/060089, WO 2001/026459, WO 2001/035725, WO 2001/034726, WO 2001/035727, WO 2001/036444, WO 2001/036597, WO 2001/036598, WO 2002/015675, WO 2002/017430, WO 2002/077185, WO 2002/079403, WO 2003/013227, WO 2003/013228, WO 2003/014327, WO 2004/031349, WO 2004/076638, WO 1998/09521 and WO 1999/38977 describing genes, including CBF genes and transcription factors effective in mitigating the negative effects of freezing, high salinity, and drought on plants, as well as conferring other positive effects on plant phenotype; US Patent Application Publication Number 2004/0148654 and WO 2001/36596, where abscisic acid is altered in plants resulting in improved plant phenotype such as increased yield and/or increased tolerance to abiotic stress; WO 2000/006341, WO 2004/090143, U.S. patent application Ser. No. 10/817,483 and U.S. Pat. No. 6,992,237, where cytokinin expression is modified resulting in plants with increased stress tolerance, such as drought tolerance, and/or increased yield, herein incorporated by reference in their entirety. Also see, WO 2002/02776, WO 2003/052063, JP 2002/281975, U.S. Pat. No. 6,084,153, WO 2001/64898, U.S. Pat. No. 6,177,275 and U.S. Pat. No. 6,107,547 (enhancement of nitrogen utilization and altered nitrogen responsiveness), herein incorporated by reference in their entirety. For ethylene alteration, see US Patent Application Publication Number 2004/0128719, US Patent Application Publication Number 2003/0166197 and WO 2000/32761, herein incorporated by reference in their entirety. For plant transcription factors or transcriptional regulators of abiotic stress, see, e.g., US Patent Application Publication Number 2004/0098764 or US Patent Application Publication Number 2004/0078852, herein incorporated by reference in their entirety.

Other genes and transcription factors that affect plant growth and agronomic traits such as yield, flowering, plant growth and/or plant structure, can be introduced or introgressed into plants, see, e.g., WO 1997/49811 (LHY), WO 1998/56918 (ESD4), WO 1997/10339 and U.S. Pat. No. 6,573,430 (TFL), U.S. Pat. No. 6,713,663 (FT), WO 1996/14414 (CON), WO 1996/38560, WO 2001/21822 (VRN1), WO 2000/44918 (VRN2), WO1999/49064 (GI), WO 2000/46358 (FRI), WO 1997/29123, U.S. Pat. No. 6,794,560, U.S. Pat. No. 6,307,126 (GAI), WO 1999/09174 (D8 and Rht) and WO 2004/076638 and WO 2004/031349 (transcription factors), herein incorporated by reference in their entirety.

The heterologous nucleotide sequence operably linked to the promoter and its related biologically active fragments or variants disclosed herein may be an antisense sequence for a targeted gene. The terminology "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, 80%, 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides or greater may be used. Thus, the promoter sequences disclosed herein may be operably linked to antisense DNA sequences to reduce or inhibit expression of a native protein in the plant.

"RNAi" refers to a series of related techniques to reduce the expression of genes (see, for example, U.S. Pat. No. 6,506,559, herein incorporated by reference in its entirety). Older techniques referred to by other names are now thought to rely on the same mechanism, but are given different names in the literature. These include "antisense inhibition," the production of antisense RNA transcripts capable of suppressing the expression of the target protein and "co-suppression" or "sense-suppression," which refer to the production of sense RNA transcripts capable of suppressing the expression of identical or substantially similar foreign or endogenous genes (U.S. Pat. No. 5,231,020, incorporated herein by reference in its entirety). Such techniques rely on the use of constructs resulting in the accumulation of double stranded RNA with one strand complementary to the target gene to be silenced. The promoters of the embodiments may be used to drive expression of constructs that will result in RNA interference including microRNAs and siRNAs.

As used herein, the terms "promoter" or "transcriptional initiation region" mean a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Additionally, chimeric promoters may be provided. Such chimeras include portions of the promoter sequence fused to fragments and/or variants of heterologous transcriptional regulatory regions. Thus, the promoter regions disclosed herein can comprise upstream regulatory elements such as, those responsible for tissue and temporal expression of the coding sequence, enhancers and the like. In the same manner, the promoter elements, which enable expression in the desired tissue such as reproductive tissue, can be identified, isolated and used with other core promoters to confer pollen preferred expression. In this aspect of the disclosure, "core promoter" is intended to mean a promoter without promoter elements.

As used herein, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements that modify gene expression. It is to be understood that nucleotide sequences, located within introns or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. In the context of the present disclosure a post-transcriptional regulatory element may include elements that are active following transcription initiation, for example translational and transcriptional enhancers, translational and transcriptional repressors and mRNA stability determinants.

The regulatory elements or variants or fragments thereof, of the present disclosure may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or either enhancing or repressing transcriptional activity of the heterologous regulatory element and modulating post-transcriptional events. For example, one or more regulatory elements or fragments thereof of the present disclosure may be operatively associated with constitutive, inducible or tissue specific promoters or fragment thereof, to modulate the activity of such promoters within desired tissues in plant cells.

The regulatory sequences of the present disclosure or variants or fragments thereof, when operably linked to a heterologous nucleotide sequence of interest can drive pollen preferred expression, of the heterologous nucleotide sequence in the reproductive tissue of the plant expressing this construct. The term "pollen preferred expression," means that expression of the heterologous nucleotide sequence is most abundant in the pollen cells. While some level of expression of the heterologous nucleotide sequence may occur in other plant tissue types, expression occurs most abundantly in the pollen cells.

A "heterologous nucleotide sequence" is a sequence that is not naturally occurring with the promoter sequence of the disclosure. While this nucleotide sequence is heterologous to the promoter sequence, it may be homologous or native or heterologous or foreign to the plant host.

The isolated promoter sequences of the present disclosure can be modified to provide for a range of expression levels of the heterologous nucleotide sequence. Thus, less than the entire promoter region may be utilized and the ability to drive expression of the nucleotide sequence of interest retained. It is recognized that expression levels of the mRNA may be altered in different ways with deletions of portions of the promoter sequences. The mRNA expression levels may be decreased, or alternatively, expression may be increased as a result of promoter deletions if, for example, there is a negative regulatory element (for a repressor) that is removed during the truncation process. Generally, at least about 20 nucleotides of an isolated promoter sequence will be used to drive expression of a nucleotide sequence.

It is recognized that to increase transcription levels, enhancers may be utilized in combination with the promoter regions of the disclosure. Enhancers are nucleotide sequences that act to increase the expression of a promoter region. Enhancers are known in the art and include the SV40 enhancer region, the 35S enhancer element and the like. Some enhancers are also known to alter normal promoter expression patterns, for example, by causing a promoter to be expressed constitutively when without the enhancer, the same promoter is expressed only in one specific tissue or a few specific tissues.

Modifications of the isolated promoter sequences of the present disclosure can provide for a range of expression of the heterologous nucleotide sequence. Thus, they may be modified to be weak promoters or strong promoters. Generally, a "weak promoter" means a promoter that drives expression of a coding sequence at a low level. A "low level" of expression is intended to mean expression at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

It is recognized that the promoters of the disclosure may be used with their native coding sequences to increase or decrease expression, thereby resulting in a change in phenotype of the transformed plant. The nucleotide sequences disclosed in the present disclosure, as well as variants and fragments thereof, are useful in the genetic manipulation of any plant. The promoter sequences are useful in this aspect when operably linked with a heterologous nucleotide sequence whose expression is to be controlled to achieve a desired phenotypic response. The term "operably linked" means that the transcription or translation of the heterologous nucleotide sequence is under the influence of the promoter sequence. In this manner, the nucleotide sequences for the promoters of the disclosure may be provided in expression cassettes along with heterologous nucleotide sequences of interest for expression in the plant of interest, more particularly for expression in the reproductive tissue of the plant.

In one embodiment of the disclosure, expression cassettes will comprise a transcriptional initiation region comprising one of the promoter nucleotide sequences of the present disclosure, or variants or fragments thereof, operably linked to the heterologous nucleotide sequence. Such an expression cassette can be provided with a plurality of restriction sites for insertion of the nucleotide sequence to be under the transcriptional regulation of the regulatory regions. The expression cassette may additionally contain selectable marker genes as well as 3' termination regions.

The expression cassette can include, in the 5'-3' direction of transcription, a transcriptional initiation region (i.e., a promoter, or variant or fragment thereof, of the disclosure), a translational initiation region, a heterologous nucleotide sequence of interest, a translational termination region and optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species or, if from the same species, is substantially modified from its native form in composition and/or genomic locus by deliberate human intervention. For example, a promoter operably linked to a heterologous polynucleotide is from a species different from the species from which the polynucleotide was derived or, if from the same/analogous species, one or both are substantially modified from their original form and/or genomic locus or the promoter is not the native promoter for the operably linked polynucleotide.

While it may be preferable to express a heterologous nucleotide sequence using the promoters of the disclosure, the native sequences may be expressed. Such constructs would change expression levels of the protein in the plant or plant cell. Thus, the phenotype of the plant or plant cell is altered.

The termination region may be native with the transcriptional initiation region, may be native with the operably linked DNA sequence of interest, may be native with the plant host, or may be derived from another source (i.e., foreign or heterologous to the promoter, the DNA sequence being expressed, the plant host, or any combination thereof). Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903; and Joshi, et al., (1987) *Nucleic Acid Res.* 15:9627-9639, herein incorporated by reference in their entirety.

The expression cassette comprising the sequences of the present disclosure may also contain at least one additional nucleotide sequence for a gene to be cotransformed into the organism. Alternatively, the additional sequence(s) can be provided on another expression cassette.

Where appropriate, the nucleotide sequences whose expression is to be under the control of the pollen promoter sequence of the present disclosure and any additional nucleotide sequence(s) may be optimized for increased expression in the transformed plant. That is, these nucleotide sequences can be synthesized using plant preferred codons for improved expression. See, for example, Campbell and Gowri, (1990) *Plant Physiol.* 92:1-11, herein incorporated by reference in its entirety, for a discussion of host-preferred codon usage. Methods are available in the art for synthesizing plant-preferred genes. See, for example, U.S. Pat. Nos. 5,380,831, 5,436,391 and Murray, et al., (1989) *Nucleic Acids Res.* 17:477-498, herein incorporated by reference in their entirety.

Additional sequence modifications are known to enhance gene expression in a cellular host. These include elimination of sequences encoding spurious polyadenylation signals, exon-intron splice site signals, transposon-like repeats and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include, without limitation: picornavirus leaders, for example, EMCV leader (Encephalomyocarditis 5' noncoding region) (Elroy-Stein, et al., (1989) *Proc. Nat. Acad. Sci. USA* 86:6126-6130); potyvirus leaders, for example, TEV leader (Tobacco Etch Virus) (Allison, et al., (1986) *Virology* 154:9-20); MDMV leader (Maize Dwarf Mosaic Virus); human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) *Molecular Biology of RNA*, pages 237-256) and maize chlorotic mottle virus leader (MCMV) (Lommel, et al., (1991) *Virology* 81:382-385), herein incorporated by reference in their entirety. See, also, Della-Cioppa, et al., (1987) *Plant Physiology* 84:965-968, herein incorporated by reference in its entirety. Methods known to enhance mRNA stability can also be utilized, for example, introns, such as the maize Ubiquitin intron (Christensen and Quail, (1996) *Transgenic Res.* 5:213-218; Christensen, et al., (1992) *Plant Molecular Biology* 18:675-689) or the maize Adh1 intron (Kyozuka, et al., (1991) *Mol. Gen. Genet.* 228:40-48; Kyozuka, et al., (1990) *Maydica* 35:353-357) and the like, herein incorporated by reference in their entirety.

The DNA constructs of the embodiments can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA. It is recognized that to increase transcription levels enhancers may be utilized in combination with the promoter regions of the embodiments. Enhancers are known in the art and include the SV40 enhancer region, the 35S enhancer element, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, for example, transitions and transversions, may be involved.

Reporter genes or selectable marker genes may also be included in the expression cassettes of the present disclosure. Examples of suitable reporter genes known in the art can be found in, for example, Jefferson, et al., (1991) in Plant Molecular Biology Manual, ed. Gelvin, et al., (Kluwer Academic Publishers), pp. 1-33; DeWet, et al., (1987) *Mol. Cell. Biol.* 7:725-737; Goff, et al., (1990) *EMBO J.* 9:2517-2522; Kain, et al., (1995) *Bio Techniques* 19:650-655 and Chiu, et al., (1996) *Current Biology* 6:325-330, herein incorporated by reference in their entirety.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213; Meijer, et al., (1991) *Plant Mol. Biol.* 16:807-820); hygromycin (Waldron, et al., (1985) *Plant Mol. Biol.* 5:103-108 and Zhijian, et al., (1995) *Plant Science* 108:219-227); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-36); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518), herein incorporated by reference in their entirety.

Other genes that could serve utility in the recovery of transgenic events would include, but are not limited to, examples such as GUS (beta-glucuronidase; Jefferson, (1987) *Plant Mol. Biol. Rep.* 5:387), GFP (green fluorescence protein; Chalfie, et al., (1994) *Science* 263:802), luciferase (Riggs, et al., (1987) *Nucleic Acids Res.* 15(19):8115 and Luehrsen, et al., (1992) *Methods Enzymol.* 216:397-414) and the maize genes encoding for anthocyanin production (Ludwig, et al., (1990) *Science* 247:449), herein incorporated by reference in their entirety.

The expression cassette comprising the promoters of the present disclosure operably linked to a nucleotide sequence of interest can be used to transform any plant. In this manner, genetically modified plants, plant cells, plant tissue, seed, root and the like can be obtained.

As used herein, "vector" refers to a DNA molecule such as a plasmid, cosmid or bacterial phage for introducing a nucleotide construct, for example, an expression cassette, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance or ampicillin resistance.

The methods of the disclosure involve introducing a polypeptide or polynucleotide into a plant. As used herein, "introducing" is intended to mean presenting to the plant the polynucleotide or polypeptide in such a manner that the sequence gains access to the interior of a cell of the plant. The methods of the disclosure do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods and virus-mediated methods.

A "stable transformation" is a transformation in which the nucleotide construct introduced into a plant integrates into the genome of the plant and is capable of being inherited by the progeny thereof. "Transient transformation" means that a polynucleotide is introduced into the plant and does not integrate into the genome of the plant or a polypeptide is introduced into a plant.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (Townsend, et al., U.S. Pat. No. 5,563,055 and Zhao, et al., U.S. Pat. No. 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244; 5,932,782; Tomes, et al., (1995) in Plant Cell, Tissue, and Organ Culture: Fundamental Methods, ed. Gamborg and Phillips (Springer-Verlag, Berlin); McCabe, et al., (1988) *Biotechnology* 6:923-926) and Led transformation (WO 00/28058). Also see, Weissinger, et al., (1988) *Ann. Rev. Genet.* 22:421-477; Sanford, et al., (1987) *Particulate Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature* (London) 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in The Experimental Manipulation of Ovule Tissues, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*), all of which are herein incorporated by reference in their entirety.

In specific embodiments, the DNA constructs comprising the promoter sequences of the disclosure can be provided to a plant using a variety of transient transformation methods. Such transient transformation methods include, but are not limited to, viral vector systems and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

In other embodiments, the polynucleotide of the disclosure may be introduced into plants by contacting plants with a virus or viral nucleic acids. Generally, such methods involve incorporating a nucleotide construct of the disclosure within a viral DNA or RNA molecule. Methods for introducing polynucleotides into plants and expressing a protein encoded therein, involving viral DNA or RNA molecules, are known in the art. See, for example, U.S. Pat. Nos. 5,889,191, 5,889, 190, 5,866,785, 5,589,367, 5,316,931 and Porta, et al., (1996) *Molecular Biotechnology* 5:209-221, herein incorporated by reference in their entirety.

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853, all of which are herein incorporated by reference in their entirety. Briefly, the polynucleotide of the disclosure can be contained in transfer cassette flanked by two non-identical recombination sites. The transfer cassette is introduced into a plant having stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84, herein incorporated by reference in its entirety. These plants may then be grown, and either pollinated with the same transformed strain or different strains and the resulting progeny having expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a nucleotide construct of the disclosure, for example, an expression cassette of the disclosure, stably incorporated into its genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In: Methods for Plant Molecular Biology, (Eds.), Academic Press, Inc., San Diego, Calif., herein incorporated by reference in its entirety). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the embodiments containing a desired polynucleotide is cultivated using methods well known to one skilled in the art.

The embodiments provide compositions for screening compounds that modulate expression within plants. The vectors, cells and plants can be used for screening candidate molecules for agonists and antagonists of the promoters. For example, a reporter gene can be operably linked to a promoter and expressed as a transgene in a plant. Compounds to be tested are added and reporter gene expression is measured to determine the effect on promoter activity.

The following examples are offered by way of illustration and not by way of limitation.

EXAMPLES

The embodiments are further defined in the following Examples, in which parts and percentages are by weight and degrees are Celsius, unless otherwise stated. It should be understood that these Examples, while indicating embodiments of the disclosure, are given by way of illustration only. From the above discussion and these Examples, one skilled in the art can ascertain the essential characteristics of the embodiments, and without departing from the spirit and scope thereof, can make various changes and modifications of them to adapt to various usages and conditions. Thus, various modifications of the embodiments in addition to those shown and described herein will be apparent to those skilled in the art from the foregoing description. Such modifications are also intended to fall within the scope of the appended claims.

The disclosure of each reference set forth herein is incorporated herein by reference in its entirety.

Example 1

EGS System Mutant Scheme

This approach utilizes a maternal embryo defective (embryo lethal) recessive mutation which is then maintained in an approach similar to that used in the Sterile Inbred Maintenance System (SIMS) or Seed Production Technology (see, U.S. Pat. Nos. 7,696,405, 7,915,398 and 7,790,951). A transgenic cassette is introduced which has three parts: a wild type allele to complement the embryo lethal mutation, a pollen ablation PTU to prevent transgene transmission through the pollen, and a seed color marker to allow removal of a transgenic population from the seeds produced. The resultant population will be homozygous for the recessive mutant allele, but transgenically complemented. These plants should segregate 1:1 in the subsequent generation for viable transgenic seed and non-transgenic, non-viable, embryo-less homozygous mutants.

Schematically:
2 Types of Plants:
  Maternal embryo defective (embryo lethal) mutant: ee
  Wild type allele to complement in hemizygous state: E–
Plant is ee+E/pollen-ablation PTU/seed color marker (E is only transmitted through egg)
When selfed: Female gametes are 50% e (embryo lethal), and 50% eE (embryo viable)
  Male gametes are 100% e (all pollen carrying E are ablated)
Seeds produced by these plants are 50% ee (embryo lethal)
  50% eEe (normal embryo due to complementing E, colored seed)
  1) Construct B, a wild-type complementing transgene/eqq-cell antidote line
  2) a pollen ablation transgene
    a. Multiple were demonstrated
      i. AT-LAT52LP1 PRO:BA-BARNASE-INT
      ii. AT-PPG1 PRO:BA-BARNASE-INT
      iii. AT-LAT52LP2 PRO:ADP RIBOSYLASE (
      iv. AT-LAT52LP1 PRO:DMETH (Dam methylase)
      v. AT-LAT52LP2 PRO:DMETH (Dam methylase)
      vi. AT-PPG1 PRO:DMETH (Dam methylase)
  3) a seed color marker
    a. Several have been demonstrated in *Arabidopsis* and maize
      i. *Arabidopsis*: KTI3 PRO:AC-GFP1; KTI3 PRO:AM-CYAN; RD29A PRO:DS-RED EXPRESS; RD29A PRO:ZS-YELLOW.
  4) (for self-reproducing hybrids) a parthenogenesis PTU
    a. Promoters have been listed
    b. AT-RKD2 is a CDS candidate
    c. Promoter driving cDNA library linked to KTI3:AC-GFP1 as an embryo reporter. This constitutes an "parthenogenesis library"
    d. Use the Union Biometrica COPAS (Complex Object Parameter Analyzer and Sorter) to identify GFP positive seeds
      i. COPAS simultaneously detects optical density, time-of-flight, RED-, Yellow-, and Green-fluorescence.
      ii. The screen involves searching through seed for DS-RED negative, GFP positive seeds indicating an adventitious embryo was formed.
        1. DS-RED negative indicates the EGS maintainer is absent, and hence the egg cell was ablated and sexual zygote prevented
        2. GFP positive indicates the parthenogenesis library is present.

Example 2

Embryogenesis Gain-of-Function Screen (EGS)

Wild type *Arabidopsis* plants are transformed with a construct containing: pollen ablation, egg cell+, and seed color marker. Plants are then selfed to create a hemizygous transgenic population.

Hemizygous transgenic population of *Arabidopsis* plants are then transformed with a construct containing egg ablation.

Seed from viable plants is grown and resultant transformed *Arabidopsis* plants are hemizygous for the egg ablation construct. These plants are transformed with a construct from apomictic library containing somatic embryony and embryo color marker.

Further to describe this in more detail:

Construct A contains egg cell specific promoter::toxin gene

Construct B contains egg cell specific promoter:toxin antidote/pollen ablation PTU/seed color marker When a plant comprising both Construct A and Construct B is selfed:

Female gametes are 100% A+B (because A—only are non-viable)

Male gametes are 100% A (because A+B pollen is ablated)

Resultant seed produced is

100% (A+A)A (homozygous for construct A, hemizygous for construct B)

Selfing this generation produces,

50% AA/B—(viable transgenic)

50% AA/—(non-viable embryoless)

Resultant seeds sorted by COPAS produce approximately 50% EGS egg+ seed (viable transgenic), 50% non-fluorescent aborted seed (nonviable embryoless).

The required components are:

1) Construct A, a recessive embryo-lethal mutant/egg-cell ablation line
2) Construct B, a wild-type complementing transgene/egg-cell antidote line
3) a pollen ablation transgene
   a. Multiple were demonstrated
      i. AT-LAT52LP1 PRO:BA-BARNASE-INT
      ii. AT-PPG1 PRO:BA-BARNASE-INT
      iii. AT-LAT52LP2 PRO:ADP RIBOSYLASE (
      iv. AT-LAT52LP1 PRO:DMETH (Dam methylase)
      v. AT-LAT52LP2 PRO:DMETH (Dam methylase)
      vi. AT-PPG1 PRO:DMETH (Dam methylase)
4) a seed color marker
   a. Several have been demonstrated in *Arabidopsis* and maize
      i. *Arabidopsis*: KTI3 PRO:AC-GFP1; KTI3 PRO:AM-CYAN; RD29A PRO:DS-RED EXPRESS; RD29A PRO:ZS-YELLOW.
5) (for self-reproducing hybrids) a parthenogenesis PTU
   a. Promoters have been listed
   b. AT-RKD2 is a CDS candidate
   c. Promoter driving cDNA library linked to KTI3:AC-GFP1 as an embryo reporter. This constitutes an "parthenogenesis library"
   d. Use the Union Biometrica COPAS (Complex Object Parameter Analyzer and Sorter) to identify GFP positive seeds
      i. COPAS simultaneously detects optical density, time-of-flight, RED-, Yellow-, and Green-fluorescence.
      ii. The screen involves searching through seed for DS-RED negative, GFP positive seeds indicating an adventitious embryo was formed.
         1. DS-RED negative indicates the EGS maintainer is absent, and hence the egg cell was ablated and sexual zygote prevented
         2. GFP positive indicates the parthenogenesis library is present.

Example 4

Figure 13:
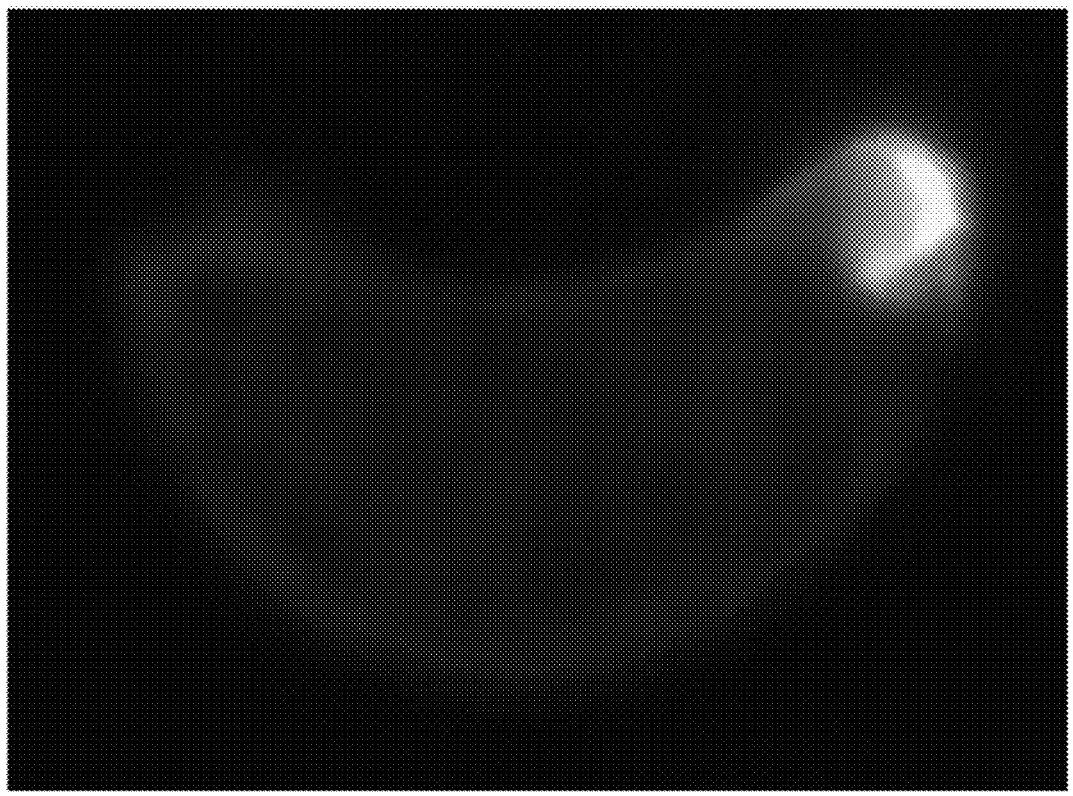
FIG. 13 is a fluorescent image of a fertilized *Arabidopsis* embryo sac with only remnants of the egg/zygote (red) and of the synergids (green). Mixing of the breakdown products green and red equal yellow. Central cell appears healthy with 3-4 endosperm nuclei indicating that fertilization did occur

Activity of the Expression Cassette Comprising the Egg Ablation Reporter AT-RKD1:Barnase-Triple Label (AT-DD45:DsRed AT-DD31:ZsYellow AT-DD65:AmCyan) in EGS Maintainer Line FIG. 13 is a fluorescent image of a fertilized *Arabidopsis* embryo sac with only remnants of the egg/zygote (red) and of the synergids (green). Mixing of the breakdown products green and red equal yellow. Central cell appears healthy with 3-4 endosperm nuclei indicating that fertilization did occur.

Example 5

Activity of the Expression Cassette Comprising the Egg Ablation Reporter AT-RKD2:Barnase-Triple Label (AT-DD45:DsRed AT-DD31:ZsYellow AT-DD65:AmCyan) in EGS Maintainer Line FIGS. 14-20 depict several events from the same transformation construct.

Figure 14:
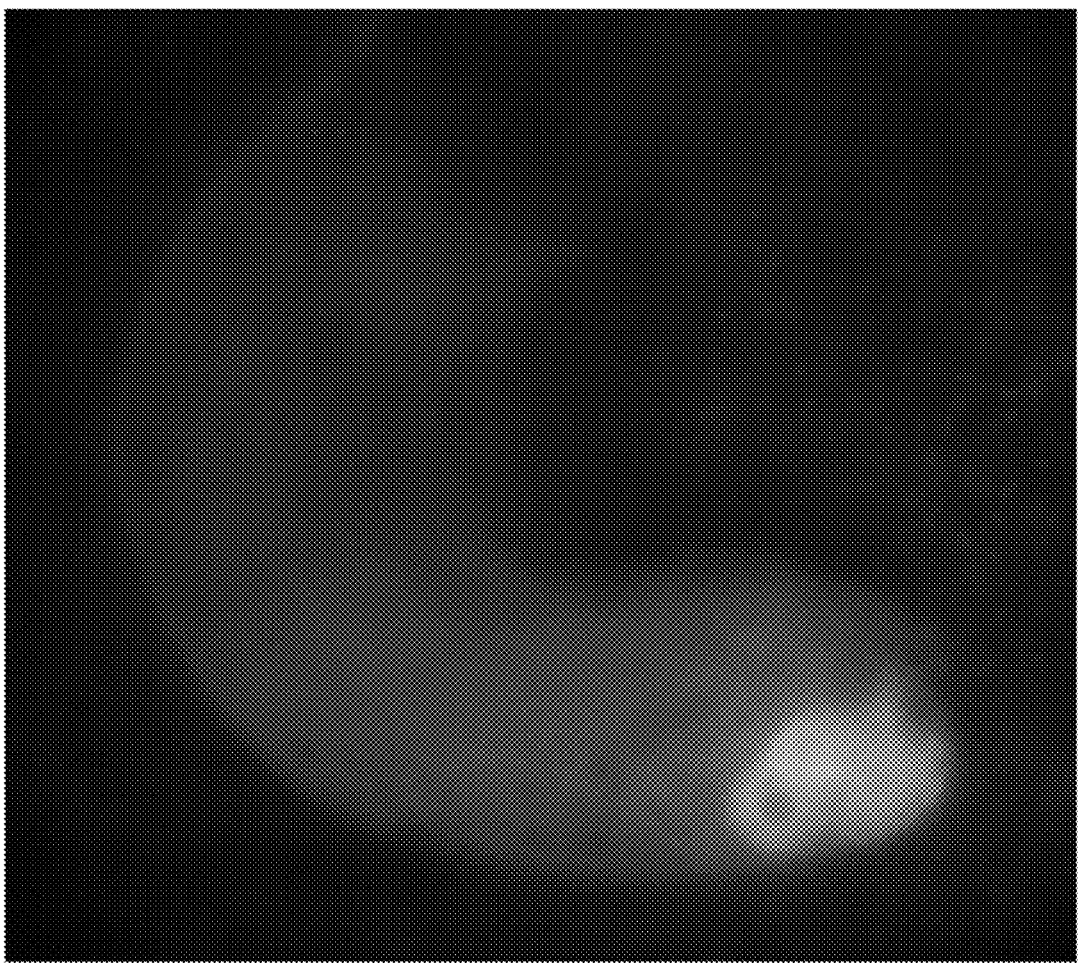
FIG. 14 is a fluorescent image of a fertilized *Arabidopsis* embryo sac with a zygote (red) that is in the process of breaking down, losing integrity and appears to be "blebbing". The persistent synergid (green) appears to be condensing and breaking down as well. Central cell appears healthy with several endosperm nuclei indicating that fertilization did occur.

FIG. 14 is a fluorescent image of a fertilized *Arabidopsis* embryo sac with a zygote (red) that is in the process of breaking down, losing integrity and appears to be "blebbing". The persistent synergid (green) appears to be condensing and breaking down as well. Central cell appears healthy with several endosperm nuclei indicating that fertilization did occur.

Figure 15:
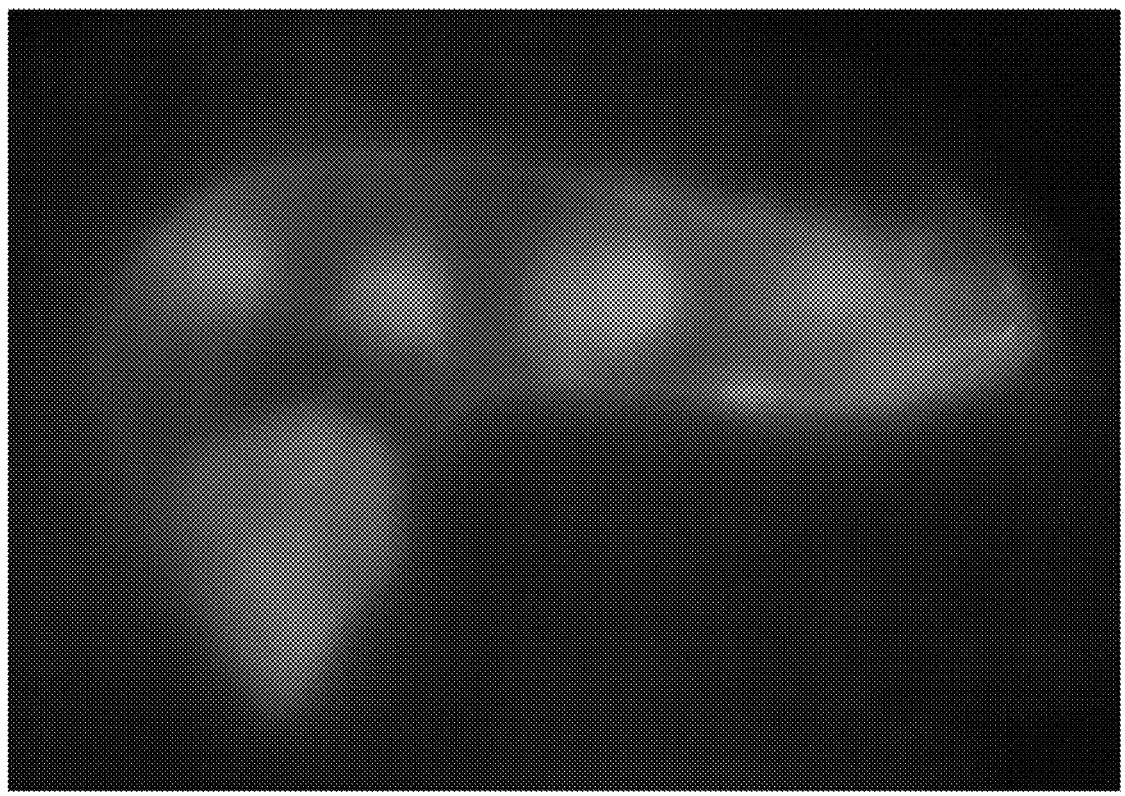
FIG. 15 is a fluorescent image of a fertilized *Arabidopsis* embryo sac showing 7-8 endosperm nuclei in a normal developing central cell. No sign of a zygote or embryo (red) nor any sign of a synergid (green) is present. The endosperm may be described as developing in the absence of an embryo.

FIG. 15 is a fluorescent image of a fertilized *Arabidopsis* embryo sac showing 7-8 endosperm nuclei in a normal developing central cell. No sign of a zygote or embryo (red) nor any sign of a synergid (green) is present. The endosperm may be described as developing in the absence of an embryo.

Figure 16:
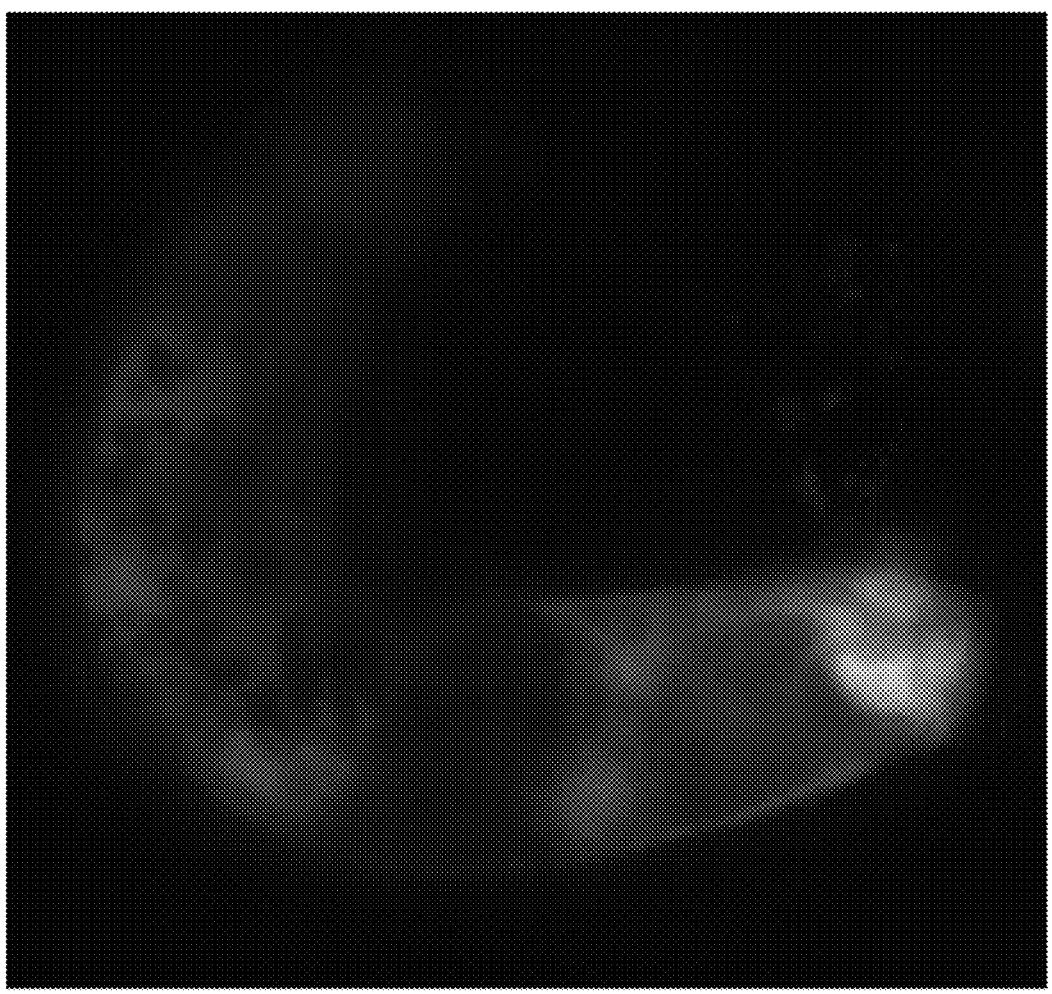
FIG. 16 is a fluorescent image of a fertilized *Arabidopsis* embryo sac with a remnant of the zygote (red) and the persistent synergid (green), where both appear to be condensing and breaking down. Central cell appears to be unhealthy and in the early stages of breaking down as is indicated by the increased vacuolation of the central cell.

FIG. 16 is a fluorescent image of a fertilized *Arabidopsis* embryo sac with a remnant of the zygote (red) and the persistent synergid (green), where both appear to be condensing and breaking down. Central cell appears to be unhealthy and in the early stages of breaking down as is indicated by the increased vacuolation of the central cell.

Figure 17:
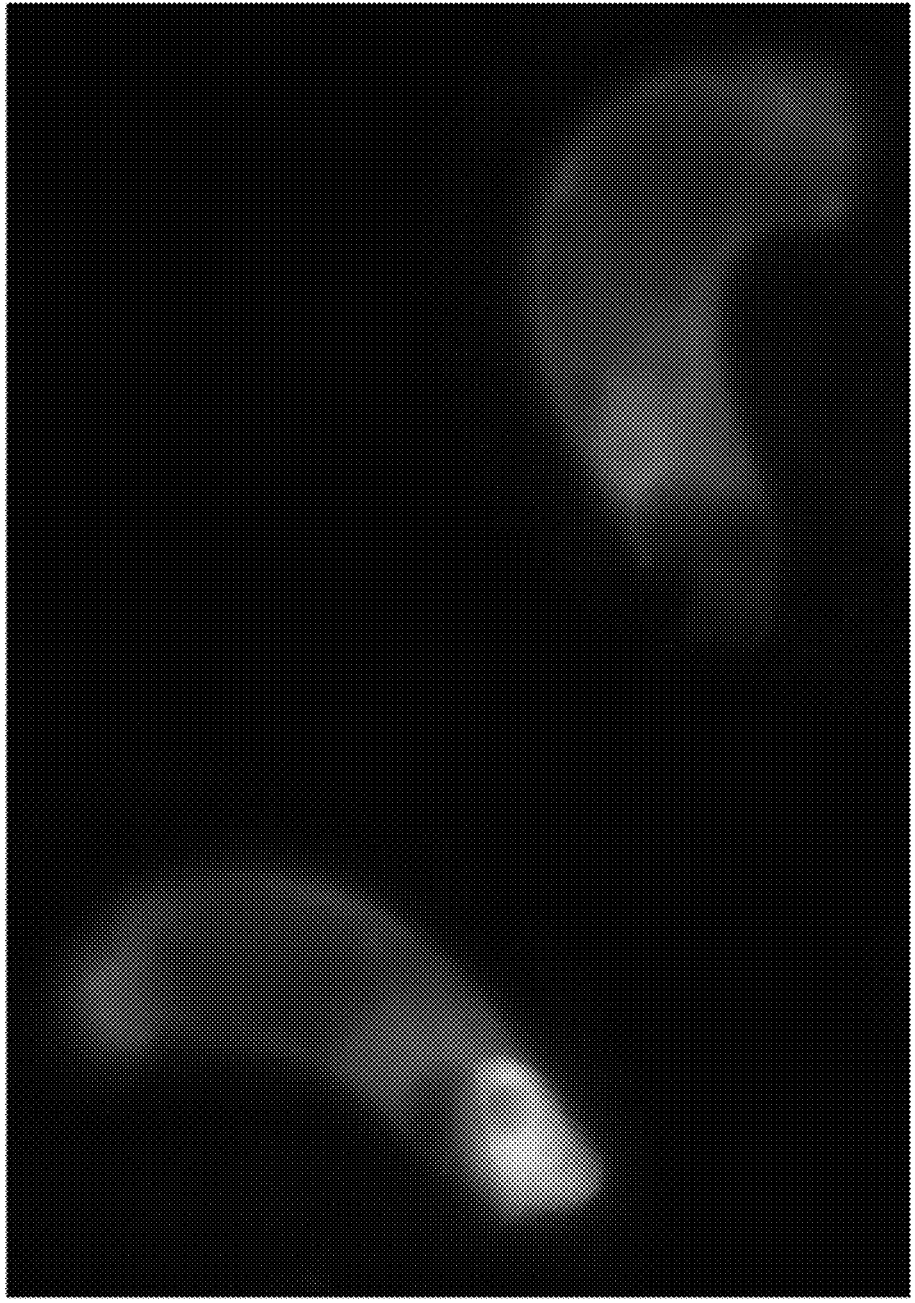
FIG. 17 is a fluorescent image of 2 unfertilized *Arabidopsis* embryo sacs just prior to fertilization. The embryo sac at left has a central cell (cyan) with the 2 endosperm nuclei and 2 synergids (yellow), but is lacking an egg (red). The embryo sac at right has a central cell (cyan) with the single primary endosperm nucleus, but is lacking the synergids (yellow) and the egg (red).

FIG. 17 is a fluorescent image of 2 unfertilized *Arabidopsis* embryo sacs just prior to fertilization. The embryo sac at left has a central cell (cyan) with the 2 endosperm nuclei and 2 synergids (yellow),m but is lacking an egg (red). The embryo sac at right has a central cell (cyan) with the single primary endosperm nucleus, but is lacking the synergids (yellow) and the egg (red).

Figure 18:
FIG. 18 is a fluorescent (A) and differential interference (B) contrast (DIC) fluorescent overlay image of a fertilized *Arabidopsis* embryo sac. The central cell (cyan) has the single endosperm nucleus and 1 synergid (yellow), but is lacking an egg (arrow).
Figure 18:
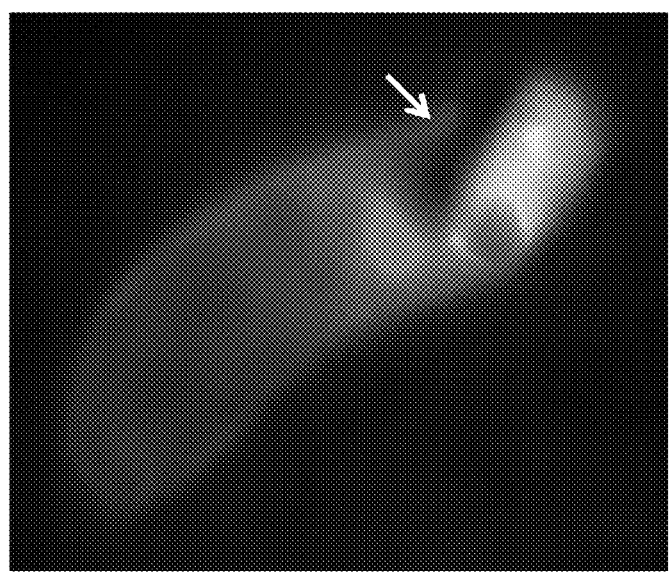

FIG. 18 is a fluorescent and differential interference contrast (DIC) fluorescent overlay image of a fertilized *Arabidopsis* embryo sac. The central cell (cyan) has the single endosperm nucleus and1 synergid (yellow), but is lacking an egg (arrow).

Figure 19:
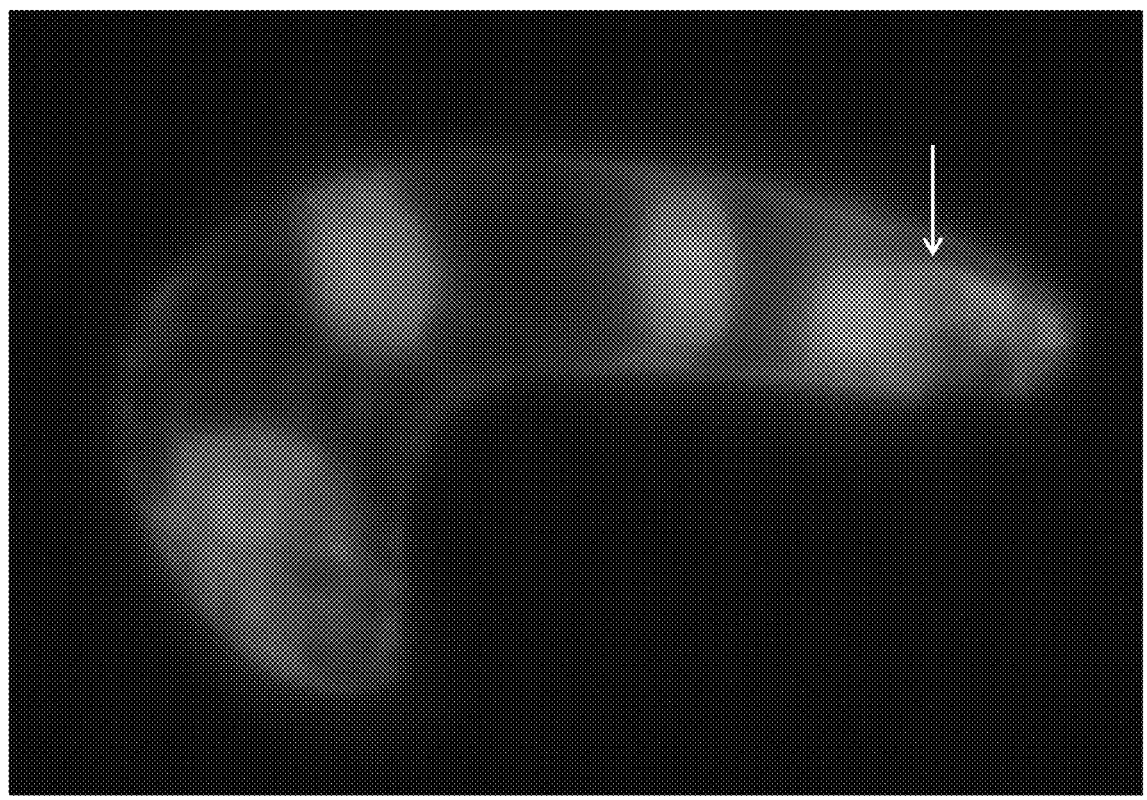
FIG. 19 is a fluorescent image of a fertilized *Arabidopsis* embryo sac with 4 endosperm nuclei in a normal developing central cell. Only a very weak red fluorescent signal (arrow) indicative of a remnant of the embryo or zygote is present. The persistent synergid (green) is breaking down. The endosperm is developing in the absence of an embryo.

FIG. 19 is a fluorescent image of a fertilized *Arabidopsis* embryo sac with 4 endosperm nuclei in a normal developing central cell. Only a very weak red fluorescent signal (arrow) indicative of a remnant of the embryo or zygote is present. The persistent synergid (green) is breaking down. The endosperm is developing in the absence of an embryo.

Figure 20:
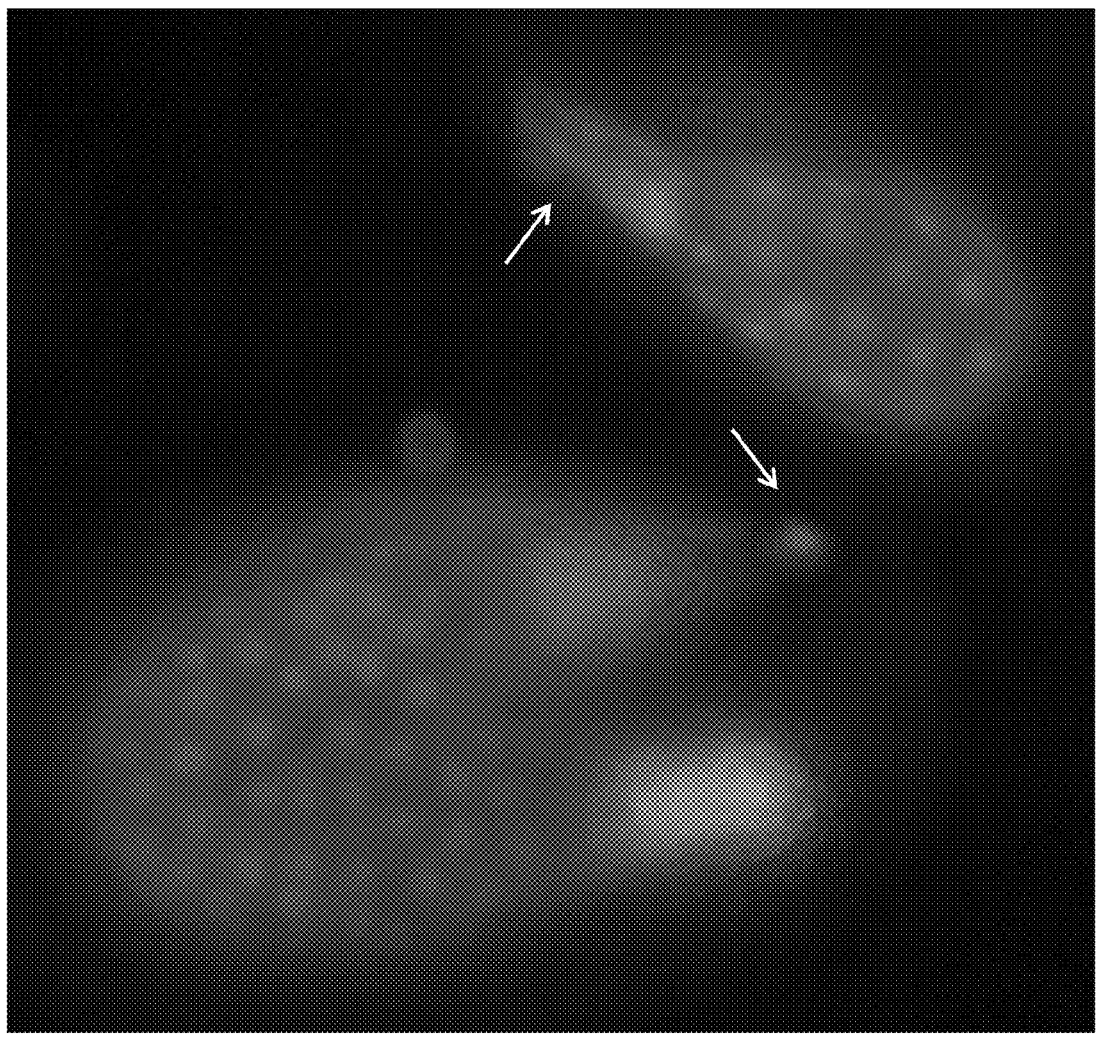
FIG. 20 is a fluorescent image of 2 *Arabidopsis* embryo sacs with well developed endosperm. The embryo sac at left has numerous endosperm nuclei in its central cell (cyan) and at its micropylar end (arrow) is a remnant of the embryo or zygote (red). Under normal conditions this embryo should be much more fully developed, at the heart-shaped stage. The smaller embryo sac at right has numerous endosperm nuclei (cyan) but is lacking an embryo (arrow). Synergids would have been lost by this late stage.

FIG. 20 is a fluorescent image of 2 *Arabidopsis* embryo sacs with well developed endosperm. The embryo sac at left has numerous endosperm nuclei in its central cell (cyan) and at its micropylar end (arrow) is a remnant of the embryo or zygote (red). Under normal conditions this embryo should be much more fully developed, at the heart-shaped stage. The smaller embryo sac at right has numerous endosperm nuclei (cyan) but is lacking an embryo (arrow). Synergids would have been lost by this late stage.

What is claimed is:

1. An expression cassette comprising the polynucleotide of SEQ ID NO: 53, wherein the polynucleotide encodes a pollen preferred promoter which drives pollen specific expression operably linked to a heterologous polynucleotide of interest.

2. A vector comprising the expression cassette of claim 1.

3. A plant cell comprising the expression cassette of claim 1.

4. The plant cell of claim 3, wherein said expression cassette is stably integrated into the genome of the plant cell.

5. The plant cell of claim 3, wherein said plant cell is from a dicot.

6. The plant cell of claim 5, wherein said dicot is soybean.

7. A plant comprising the expression cassette of claim 1.

8. The plant of claim 7, wherein said plant is a dicot.

9. The plant of claim 8, wherein said dicot is soybean.

10. The plant of claim 7, wherein said expression cassette is stably incorporated into the genome of the plant.

11. A transgenic seed of the plant of claim 10, wherein the seed comprises the expression cassette.

12. The plant of claim 7 wherein the heterologous polynucleotide of interest encodes a gene product that is involved in cell ablation, prevention of transgene transmission, organ development, stem cell development, cell growth stimulation, organogenesis, somatic embryogenesis initiation, self-reproducing plants or development of the apical meristem.

13. The plant of claim 12 wherein said gene product is selected from the group consisting of: ADP Ribosylase, DMETH, BA-BARNASE-INT and other cell growth inhibitor.

14. The plant of claim 7, wherein the heterologous polynucleotide of interest encodes a gene product that confers drought tolerance, cold tolerance, herbicide tolerance, pathogen resistance or insect resistance.

15. The plant of claim 7, wherein expression of said heterologous polynucleotide alters phenotype of said plant.

* * * * *

SEQUENCE LISTING

<160> NUMBER OF SEQ ID NOS: 56

<210> SEQ ID NO 1
<211> LENGTH: 1327
<212> TYPE: DNA
<213> ORGANISM: Arabidopsis thaliana

<400> SEQUENCE: 1

| | | |
|---|---|---|
| gagccatata tatgatgctc attgtgtttg ttcttatgta actactcttg caactctaag | 60 |
| ttcaaagtgt caaatcaaga ttcaagatca tcatcataat aaaatatcaa atcacaaact | 120 |
| tagaatctct tacacaaaca tacaaataga gataacagta atctttcctc atctattcat | 180 |
| cacaaccata tattatccat ataataaaaa ctactaaaac cgaatcgaga caaaaggatc | 240 |
| ctcatgatct cataatctat agctataaca taacatagca aatatataat catcataatg | 300 |
| actatatatt attaagatca agaatcaaga tgtgatctta attatatctt aacaataagc | 360 |
| aatacactcc ttcttacaat ccatagtgaa agtcttaaaa ggcttaacaa tgattaatgt | 420 |
| ttgccatttt aatctcccttt gaccgagttt tttcatgttg agtctatata ctttaataac | 480 |
| taatttatag ccaaattaac ataatgtggc gaatcatgta atgtacgtga aaacgtaatt | 540 |
| ctgttttaag caaaatttgc acatatacat tacgattgtt tgatttatca tataattttt | 600 |
| gattctgtat tttgttaaat agttagttat atattaagca aagattgcac acattacgat | 660 |
| tctttgattg ccatataatt agtttcatcg tactaccttt ggaatattcc actatctatc | 720 |
| aaagagattc aactatccgt ggtcaccatt ttataatcta taaagtataa agtgtgtaaa | 780 |
| aaaaacaaat tcaaaacgat atacacatta aaaaaaaatc cggaattggt ttgctgtcct | 840 |
| gtgatcctat atttcggtgt agagtcttct atatttcaaa agttcagaat ataatcattc | 900 |
| tatactaaat tgagtaattc agtcaatcat gatctaccaa cttcttaatt acagttacct | 960 |
| aacctactca tttagttaga aattattgat atcctcttat agtcttatac tcatttgaat | 1020 |
| tataattagg taatatatat aattaggtac actattcgta tatctataat aagaaagacg | 1080 |
| acaattgtaa gagttaaaac tgagccaaaa agttatggtg ggaatatcag taacgctaca | 1140 |
| cgagagataa aaccggtctg attcggaatt accataataa gttgaataaa ccaataattg | 1200 |
| aatccgaacc aaattcgaat ctaaccccaa attttattgc ttaagacgaa ttatttacta | 1260 |
| tttatatgta tataaaaaag cttctatacc acacagtcac acatgcacac acttctcact | 1320 |
| tcagaca | 1327 |

<210> SEQ ID NO 2
<211> LENGTH: 1326
<212> TYPE: DNA
<213> ORGANISM: Arabidopsis thaliana

<400> SEQUENCE: 2

| | | |
|---|---|---|
| agccatatat atgatgctca ttgtgtttgt tcttatgtaa ctactcttgc aactctaagt | 60 |
| tcaaagtgtc aaatcaagat tcaagatcat catcataata aaatatcaaa tcacaaactt | 120 |
| agaatctctt acacaaacat acaaatagag ataacagtaa tctttcctca tctattcatc | 180 |
| acaaccatat attatccata taataaaaac tactaaaacc gaatcgagac aaaaggatct | 240 |
| ccatgatctc ataatctata gctataacat aacatagcaa atatataatc atcataatga | 300 |
| ctatatatta ttaagatcaa gaatcaagat gtgatcttaa ttatatctta acaataagca | 360 |
| atacactcct tcttacaatc catagtgaaa gtcttaaaag gcttaacaat gattaatgtt | 420 |
| tgccatttta atctcccttg accgagtttt ttcatgttga gtctatatac tttaataact | 480 |

```
aatttatagc caaattaaca taatgtggcg aatcatgtaa tgtacgtgaa aacgtaattc    540
tgttttaagc aaaatttgca catatacatt acgattgttt gatttatcat ataattttg     600 attctgtatt tgttaaaata gttagttata tattaagcaa agattgcaca cattacgatt    660
ctttgattgc catataatta gtttcatcgt actacctttg gaatattcca ctatctatca    720
aagagattca actatccgtg gtcaccattt tataatctat aaagtataaa gtgtgtaaaa    780
aaaacaaatt caaaacgata tacacattaa aaaaaaatcc ggaattggtt tgctgtcctg    840
tgatcctata tttcggtgta gagtcttcta tatttcaaaa gttcagaata taatcattct    900
atactaaatt gagtaattca gtcaatcatg atctaccaac ttcttaatta cagttaccta    960
acctactcat ttagttagaa attattgata tcctcttata gtcttatact catttgaatt   1020
ataattaggt aatatatata attaggtaca ctattcgtat atctataata agaaagacga   1080
caattgtaag agttaaaact gagccaaaaa gttatggtgg gaatatcagt aacgctacac   1140
gagagataaa accggtctga ttcggaatta ccataataag ttgaataaac caataattga   1200
atccgaacca aattcgaatc taaccccaaa ttttattgct taagacgaat tatttactat   1260
ttatatgtat ataaaaaagc ttctatacca cacagtcaca cacgcacaca cttctcactt   1320
cagaca                                                              1326

<210> SEQ ID NO 3
<211> LENGTH: 2018
<212> TYPE: DNA
<213> ORGANISM: Arabidopsis thaliana

<400> SEQUENCE: 3
gtagtgaact acgatatata tcattgtgga ctgacttgtg gtgtgtgctg tctcagcgat     60
tagcaacctc acaaataaag ttaatactaa taagtaccct actgtttaac gacctcacaa    120
atcaatacta ataacttcta aatttgaaat ttgttctcta cgtttcacac tacatttatg    180
gataatcggg tgtatctata gtatatgcat gcgttcgtat gagttttaat accagcgttg    240
actgtcggca gtaggaaat aatccaatta ataatacgtt tgacaaaaga ttaaactgta    300
gtactatata taatggaata tttaatccag atatcaaccg ttgaaagtta tctaatttaa    360
tttgataacg atttccagga ctgtccccaa atctatctga aagttattaa tcactccttt    420
ctaaacaata attgaacttt tcttaaaaa aacttctacg acaacacatt cctttgcat     480 aacgtagaag tcaatcaaag tttttaaata cttctatcaa attttttaagt aaaatagtat    540 tgacacgaaa tgcaaaagac gaagtatact gaatataaaa tatcacggct acaatgcaac    600
atttaagaat tagatgattg gaaatcgata cagaaaaata atctaagaga attaggccgt    660
cacttgtgtt gtgtgggagc aaaacaagga ccaaaaatat cgggacaaat aggttggtcc    720
aacctatagg tagaggtagc ccacttggca tagctcataa taccattacc agctcatatg    780 tttttttcaag gattggagaa aattaaagaa agatgtaatc gattagagta acagtggagt    840
gctgaattta agttagttaa gaaaataatt ggtgttactt cttataaact tttaactcaa    900
aaccaattcg taatgaatag atagatccat gtctattata tcttatatac tattcaaacc    960
tcttcttata tatttttcca atgtggatta ttcgcccata gataaaagat aaaacttaac   1020
aattggtaag acaatatgac ataaagtcct tagttctact tacaaagaat tttgtcaatt   1080
accttccaaa atttagatct tctaaaccct aagttattgg gttcaccaa tataatgggt   1140 catttcatct attcacccga ccgttagatt taccaatttc tcatcatatc tcgattttca   1200
```

| | |
|---|---|
| acatttaaga aagtaatcaa gtttagccga aatgcaagat gatacagaaa caatagcgtt | 1260 |
| taacggtgtt agatgataaa ctcatcaact ccattaagaa aaccaatcct gtaagaggta | 1320 |
| aagaagggga gaccataatt aatgtctaat actttcgtaa tgaccactat taatgattag | 1380 |
| tactatgatc tatgaagttg aagctctctt tttttttttt ttttttcccct tcacgtccat | 1440 |
| agttagttac agcattgatg aaattttgc tgagaataga cgacccttta tcctccaccc | 1500 |
| tacgctttaa gtggttggga gttagaccct gccagataga ttccaatcct aagataagtc | 1560 |
| tgtttaacaa acctatcata tgtgaaagtg aaaaccatta tgttgaagaa ttatctaagg | 1620 |
| cgtagagata atttctgcag caaaaacatt ttttttaaaca ttgcgttata catttttagga | 1680 |
| tagtttatat aatcagccaa agtgtatatt tctgtaaaac acattactat cttgacatt | 1740 |
| ttgtgataag ctatataatc agtaacctgc tacgtatagc ttaaccccac tattataatt | 1800 |
| atgattcctc attcagtaaa actatatagc tgaattaata aagtttatta gggtctaatg | 1860 |
| aagttggtgt gatcatttaa taatattgtt atttcataac tcggaattga attatttatt | 1920 |
| acccttgcca tcttaaatct acatttgcaa ctcacccaaa agctttatcc tttgtgtttt | 1980 |
| ttccactgta tactgaaaac aaatctgagg tgacgaag | 2018 |

<210> SEQ ID NO 4
<211> LENGTH: 1974
<212> TYPE: DNA
<213> ORGANISM: Arabidopsis thaliana

<400> SEQUENCE: 4

| | |
|---|---|
| atacaaaaat atttatagt agtgaactac gatatatatc attgtggact gacttgtggt | 60 |
| gtgtgctgtc tcagcgatta gcaacctcac aaataaagtt aatactaata agtaccctac | 120 |
| tgtttaacga cctcacaaat caatactaat aacttctaaa tttgaaattt gttctctacg | 180 |
| tttcacacta catttatgga taatcgggtg tatctatagt atatgcatgc gttcgtatga | 240 |
| gttttaatac cagcgttgac tgtcggcaag taggaaataa tccaattaat aatacgtttg | 300 |
| acaaaagatt aaactgtagt actatatata atggaatatt taatccagat atcaaccgtt | 360 |
| gaaagttatc taatttaatt tgataacgat ttccaggact gtccccaaat ctatctgaaa | 420 |
| gttattaatc actcctttct aaacaataat tgaacttttt cttaaaaaaa cttctacgac | 480 |
| aacacatttc ctttgcataa cgtagaagtc aatcaaagtt tttaaatact tctatcaaat | 540 |
| ttttaagtaa aatagtattg acacgaaatg caaaagacga agtatactga atataaaata | 600 |
| tcacggctac aatgcaacat ttaagaatta gatgattgga aatcgataca gaaaaataat | 660 |
| ctaagagaat taggccgtca cttgtgttgt gtgggagcaa acaaggacc aaaaatatcg | 720 |
| ggacaaatag gttggtccaa cctataggta gaggtagccc acttggcata gctcataata | 780 |
| ccattaccag ctcatatgtt ttttcaagga ttggagaaaa ttaagaaag atgtaatcga | 840 |
| ttagagtaac agtggagtgc tgaatttaag ttagttaaga aaataattgg tgttacttct | 900 |
| tataaacttt taactcaaaa ccaattcgta atgaatagat agatccatgt ctattatatc | 960 |
| ttatatacta ttcaaacctc ttcttatata ttttccaat gtggattatt cgcccataga | 1020 |
| taaaagataa aacttaacaa ttggtaagac aatatgacat aaagtcctta gttctactta | 1080 |
| caaagaattt tgtcaattac cttccaaaat ttagatcttc taaaccctaa gttattgggt | 1140 |
| ttcaccaata taatgggtca tttcatctat tcacccgacc gttagattta ccaattctc | 1200 |
| atcatatctc gattttcaac atttaagaaa gtaatcaagt ttagccgaaa tgcaagatga | 1260 |
| tacagaaaca atagcgttta acggtgttag atgataaact catcaactcc attaagaaaa | 1320 |

```
ccaatcctgt aagaggtaaa gaagggggaga ccataattaa tgtctaatac tttcgtaatg    1380
accactatta atgattagta ctatgatcta tgaagttgaa gctctctttt ttttttttt    1440 tttttccctt cacgtccata gttagttaca gcattgatga aattttgct gagaatagac    1500 gacccttttat cctccaccct acgctttaag tggttgggag ttagaccctg ccagatagat    1560
tccaatccta agataagtct gtttaacaaa cctatcatat gtgaaagtga aaaccattat    1620
gttgaagaat tatctaaggc gtagagataa tttctgcagc aaaaacattt ttttaaacat    1680
tgcgttatac attttaggat agtttatata atcagccaaa gtgtatattt ctgtaaaaca    1740
cattactatc ttgacatttt tgtgataagc tatataatca gtaacctgct acgtatagct    1800 taacccccact attataatta tgattcctca ttcagtaaaa ctatatagct gaattaataa    1860
agtttattag ggtctaatga agttggtgtg atcatttaat aatattgtta tttcataact    1920
cggaattgaa ttatttatta cccttgccat cttaaatcta catttgcaac tcac           1974

<210> SEQ ID NO 5
<211> LENGTH: 490
<212> TYPE: DNA
<213> ORGANISM: Arabidopsis thaliana

<400> SEQUENCE: 5
tcatgacagg gtaggatttt atttcctgca ctttctttag atcttttgtt tgtgttatct      60
tgaataaaaa ttgttgggtt ttgtttcctt cagtggtttg attttggact tatttgtgtt     120
aatgttgttt tggctgttct cttaatatca ataacaaata aatttactgg ttggtatcta     180
agatctaaca atagttacta tttttagagg taaagacacc aaccttgtta tattggtcag     240
agagctaaaa ccttgacttg ttgggaaaac aaaactctaa tgacagaaaa tctgacatga     300
tgccttataa ttcacagcct catgttctac ataaatccta acaatagcac tttgtttctt     360
cattatattt tgttaagtcc actcttctct ctcatatctt ctaaccaaaa cagagtcaca     420
aggggctctt aagcccttcc aactaaattc ttttctttg ttctcttgaa actgaatcca     480
ccagacaaaa                                                             490

<210> SEQ ID NO 6
<211> LENGTH: 2255
<212> TYPE: DNA
<213> ORGANISM: Arabidopsis thaliana

<400> SEQUENCE: 6
tgggttttat ttttgacatt tggttttata ctttagttcc gttgactttc gcctccacca      60
taatttctcc aattcagatt tgattcggtc tgaacacaaa gtccggtttg gtttcttatt     120
tgtcttaata tcgattactt tccatctata aaatattttt ctacaacatc ttaagaatta     180
taattgagtg atgttgatgc tactatttta agtttagaaa ataaacacta aaagacaaa     240 tgtctcactc atcaaagtaa aactcttgaa aagtgcaaga gctctgaaat ttgagaacga     300
agacaagact ccttgttttt ttttgttttt ttttgctaaa aatttaaata ttcattatta     360
caatgaaaat ttcggttaca taataaatgg taaccaaatc atggttccat gacaaaaaag     420
gataaaaagc atgaagcat accaagactc cttgttacta cgtcaatctc ttttatacgt     480
tttcagccaa gattccggat tatgaaagaa tcttgggatt ctaacacttt tcttttttt     540 gcttgaaaga ggtttacaaa ttttaacact ttttttttgt tgaggatttt agagtgaaac     600
acatgttttg aactgtcttc aactgaacaa ttcatgttag gcgtctatat aaccgtcggt     660
```

```
tattcacgag gtaactacac atgaacatga taaatttact ctctcttttc attaaaaaaa      720
agttgtacaa cttaattact tatgtcatga aaatagtata tacgtaaaag tagattattt      780
ttgtggtttt ccttttttt  actataacaa taaataattc tatgttacct aaattttctt      840
aggtagtata atggatcaaa ttgatatgga gtaaacaaaa gaaaaactta ataatctgg       900 tctataattt gaagcgcttc aagccttcaa catcaatccg agtacgaaca ataatatgag      960
atttcatcaa atattatcc  tggaaacgat ttttcattta tatgcgatta tattgttaat     1020
gaaagttgga aatacataat ctagacacgt aaatgtcgta ttgatcatgt tgtgaaatga     1080
gctgtcgcct tggtggcact ttttggcatt ctctatttct ctttccacat ttaccacaat     1140
gtatccaaat aggcaaatat ataagcttag agagttggct gcacgttttt gctaaacttg     1200
ataaatgagt caatcaacc  aatatagcca ccatccatat ctacaaatct acacttatca     1260
tctaaacttg aagaatattt gttattttat cactaaccac aaaagacaag actcgttact     1320
taagttaaat gatagtgaca tgattaagag aatattagct attaggtcgg aaataagaga     1380
aataagactg gtagtggtat ggttatgtaa attatcagta catgtatata acacttgtcc     1440
aaataatggc tttcacatta caagtcattc tttccctgag actactgcaa gaaacaaaca     1500
cggaattctc gtgataaacg gattagtacg aaggaaaaag taaatgcag  taaccaattt     1560 ttatatttca aaaacaagg  cattttggat gcaatgaaat atttagatat ataaatttga     1620
ctagtgacaa caatttaaag ttgttagatt tctcaaatcc aaaaaaaagg aaataaataa     1680
ataaatagtt tatggctatt caaattgtgt attatttttt ctattggtta aaatctataa     1740
aagatttttt ttttattact tcttaaattt atgtttatag ccaaaacatc taataaaatg     1800
ggacagagaa taataactag gaattcaaac acattatcaa tgattagcag aataaaagtt     1860
tggaacatct aaacctaatg actttatact tcccctttt  agagtttact ttgtatggaa     1920
aactttgtaa gctaacaaac aaaagtattg aaatcgtgaa aaatagtaaa gcttttttgag    1980 ctgcaatatt tgatgcgttg aaacgagttg gaaacagctt tcactacact aaaaacaaac     2040
ttaatctcaa aatttagatg gattaaactc aaaactttt  aattaattga ataggatttt     2100
aggatgatgc agtgaatata gactatttgg tgaaaaaata caacgtaacg tacgtggctg     2160
ctctaagcct atataacata gcccaagaga gtcgtgttct aatgtgatta agtaaagtga     2220
gggagaagca acgagagata gagatagaga gatca                                2255

<210> SEQ ID NO 7
<211> LENGTH: 1185
<212> TYPE: DNA
<213> ORGANISM: Arabidopsis thaliana

<400> SEQUENCE: 7
ttctctctag caaaactctc tctctttctc ccttgtagaa ttaattagct atcataaata       60
tagtagttca tcagttccac ttccactaaa ttattgtttt tggcaaaaca gtaacttaag      120
ttatataaaa aaaaaaatca ttagtcaatc aatcacagtc ctttatgata aaacgaactc      180
ataattattc caccgacaac atgcgtttta aattattttt tcttaaatta tattatatta      240
tattgatatc aacctagcta aaataattcg gatggcgaaa tcggacaatt tttaatagaa      300
aaaatgggta tgaagatagt ctatgattcc gttcttagcg actagaggga cctgctcaaa      360
tctcccgggt gatacgcgat gtcaagctca atagaacccc acaaccgacg agaccgagaa      420
atccttgatt tgggctagaa gattttgaaa tgaatttaat atattctaag taacttgctt      480 aaatttttt  tcaaactcta aagacataac taacataaag taaaaaaaaa aagttaatac      540
```

```
atgggaagaa aaaaattaaa ctaatgatta gctctctaac gtgtttaatc tcgtatcaag    600
ttttttttta aaaattatat tgctattaaa acattgtact attgtttcta ttttgtttag    660
ctattattct tgtgaaatga aaagttgtgt ttattcaatt actaaatggc aatatttatc    720
ttggaaaact atacctctaa ttggattagg ccctagacat cctctttagc ttattgacgt    780
taaaattatt cccaaaacta ttaaagttta gtagtttgaa agatgcatca agacctactc    840
agataggtaa aagtagaaaa ctacagttag tgtgattata ttttaaaata tataaaacaa    900
tcttattaaa ctaatatttc aagatatata ctcaaatgga agataaaaac atttagtctg    960
ttaccactac cagcctagct agtcactaat agtcactttg gaactgagta gatatttgca   1020
tcttgagtta ccatggactc aaaagtccaa aaagagaccc cgagtgaaaa tgctaccaac   1080
ttaataacaa agaagcattt acagcggtca aaaagtatct ataaatgttt acacaacagt   1140
agtcataagc actcaacaca aactctttac gaatactttt aaggc                   1185
```

<210> SEQ ID NO 8
<211> LENGTH: 2119
<212> TYPE: DNA
<213> ORGANISM: Arabidopsis thaliana

<400> SEQUENCE: 8

```
cagaatatct aaccatttca tccagattat atatttgtta atatctaaca ttatcgatat     60
tctatcgcaa catggaatca ttaatatcta acaatttcga acattttcaa tgttcataac    120
gcaaaacaat gtcaaagtaa attcaaaacta cacgaagtaa atgtattgta tgaccacata    180
tacaaagtat aggacgtcat gtggttaaca ccatagacat acaattccga taaaccggtc    240
agttgactcc ggcgttgact agggttgacc ggcgttgacc aacaaaaaaa ttcaaaaaaa    300
tcttttaaat tattttaaat attcaaaaat acaaatatt ttttttttgg ttttgtatat     360
tcaaaaacat attctatatt tcaatgcatt aaatcttaga aaaattagtt ttacaaaaaa    420
aatcaaaatt taactaaaaa tagattaaaa atcattatta aattttaaat tttaaatgaa    480
aacaggaaaa tattattata gttaattaag taaggaaatt gcttattttt atagtgtcaa    540
ttaaaacact tcaattattt ctatacaata ttttttataa aaaaaaatca accacaaaaa    600
ttattagaat aaaacgtaat acaaatgaat tttattttaa aaactttttt gctgaaatca    660
acattgttag atttttctatc tttttatata ttaaaaagaa aaattgcaag tttttggttg    720
tttatgtgtt actacgagaa cttttcttaa taatatttgt tacaaaagga actacatagt    780
atacaaaaat aaatttagac taaagagtat ataaaaaata ttataatttt ctttaccatg    840
caaactttag attaaagagt catatactca atttcatatt gcttcctaat acaattgagt    900
atatgactct ttaatctaaa gtttaataat gattttattt ctagttttag tttagttttg    960
aaattaaaaa taaaactaat tattataaga tttaatgcat tgaaaataca aatatatttt   1020
tacgaaatat agaatatgtt tttgaatata taaaagaaaa aaaatatttt cgtatttttg   1080
agtattaaaa ataattttaa attttttttgt tggtcaacgc cggtcaacac tagtcaaagc   1140
ctgagtcaac tgaccggttt accggaattg tatgtcaatg gtgttaacca catgacgtcc   1200
tatacttcat atatgtggtc atgtaataca tctacttcgt gtctacttcg tgtagctgga   1260
tatacaatgt atagtaggta tgtgtgacca tgtattctct tatactttgt ttacctagca   1320 atctttttttt taaattaaaa taaatatgcg gtttagatat gaaactaccc aacaaattta   1380 acatttttaaa cgttcataac gtaaaacgac gtcgttatag acacatattt tccatgtgtc   1440
```

```
tgctgactta tcatcttcac ggagttgact aacacccgtt actttgactc tgaattttgt   1500
acttttcctt aagttgaggt atgaaattca aataaatatg cggttaatat atgaaaatac   1560
ccaacaaatt tttttggata cgaaaataca ctcagaaaat agtacgggta tgaaaatacc   1620
cttttcccgt atttgataca tgtctaattc ggttcaaata aaccgaatat gaaaattttc   1680
agttttattt cggaagttaa ataaatctag ataaccgacc tgaaaaccc gagtcccgac    1740 cgaaccgaac cgaaattaaa ttcggtttaa ttcggaagca tttccaaaaa ccgaaattcc   1800
ctaaaaccga ataacccgac ccgattaaac cgatttgccg aactcccagg cctaaattca   1860
cacttggctt agaaaaactc tttgtagatg ttaaaattcg gtaaaattaa cctcaccaaa   1920
gctaattatt accaggtgaa gaaagcatta aaatttcaaa gtgtgtatga cagaggtttt   1980
agaaagcgac tgatgtacgg acatatcaac aactccccta taaagatact cagctaaaca   2040 caaaacaga atctattctc aacacaacac taaagacaat tgtaccaacc acacaaccac    2100
aagagagaga aaagtgacc                                                2119
```

<210> SEQ ID NO 9
<211> LENGTH: 853
<212> TYPE: DNA
<213> ORGANISM: Arabidopsis thaliana

<400> SEQUENCE: 9

```
tggttctgct acatgcagat gatactatcc gttgttgaat tgtcgatta gaattctttt      60 tggtgtacac aatgcggttg tcataacgcc ttaatagctt gtattagtca agaactgca    120 tatggtcttg tgttttcttg tcatcgtgtt tttgtaacca caaactgttt tgagctatac   180
tactatatat attgagatat atctgccgtt tcgatacaca cttgggatct ggggatgagc   240
acatcgtaaa acaaaataga agttgatcct caaaacttct ttgtaacctt gtgtcatcac   300
aacaaaaaat cttcaatgtg tttgttctct ccttaaagta tatcttgatt catgcagtaa    360
caaaggcaaa actcttttgc aagagtatag aaaccagact caagctgtgc gatggtgatt   420
cttttggaga agttggattt gtgctctgat gtaaagggaa acttaagcta aaaggtccat   480
caatggaggt gacacatagt tttagaaaat gtgcttttct catgctagaa atgttatgga   540
gacccaaaaa tgcttttcgg aaaaaattct catgctagta gctaggctct acttaacgag   600
gtgacagcta aaataagttc tttttattcc attttcagaa tagtgacatt cttctcacaa   660
atatagaaaa actacaatta atgctactgc agagtctgat tacgttttaa gctaatttt     720 ccattttttag gacgtggtag attgtgtaga ttattgctaa acagctcatg agttcaataa   780
ttcacttatt cttcactcca tcttcagcaa aaaaaaaaaa agtaagaaga aacactgaaa   840
gctctccact acc                                                       853
```

<210> SEQ ID NO 10
<211> LENGTH: 4755
<212> TYPE: DNA
<213> ORGANISM: Arabidopsis thaliana

<400> SEQUENCE: 10

```
aattcgatag acgctgggta aaaaaattcg gaggacgacg aaagagaaaa cgagtgtttc     60
agtcactgcc ccacggagct ctcggaaatt tgtcttcccc ttgtcgtcgt ctccctatct    120
actgcttctt cttcgttttc gtcttcttta tcaaggtgcg ctttagcttc tcaacgccgt    180
ttgattttta gaatttcgat tttttttttt ttttcttcta gttcttgaat caatccggaa    240
tttggcgact atgttgcttc gtttgtaaat cgtattctcc tgtttagaaa tcttcaattg    300
```

```
actgtgttat aggaacaatt taaatctcaa tttcaatgtc tcttttagtc accttcgtgt    360
agtaatttgc ttttgaatta ctgttaatga atctcaaaaa atggatttta taatttggga    420
aaagggcttc tgggtttaa ttaaagaaca cgagataagg tctggttttt tcttttcatt    480
tctttgtgtg tgttttttggt ttctttgatt ttcttctggg ttatggtccg tttgagtctg    540
gtgatagtta gttggcaacc aattttatt gatctattac aatcgagaac acaaaactaa    600
accctaagaa agaagtacat aaagttgttg aaaagatctc gttaactctc ccaaagtcct    660
agggctttca cacaaccagt gattaaataa cctttgagct gttctccttc ccacactta    720 tatgtgtgtt tgtggtttgt ctaatttgtg aggagcttct atgaaacctc tggttatttt    780
aattgttttc tgcaattcct gattgatatg tttatatata tttcttgtat ttgtgaattt    840
gtgtaggaat gctgttaat tggaatcaac aatggagaat ttgacggaaa tagaatcaac    900
gatggagagt ttaacggaaa tggagagtga gagagttgaa cagggtaccg ataaggaaat    960
tggaagtgga gagaaaaggc aggatgatgt aaaggaaacg gagaatgaga attctggaga    1020
gagagtagga gaggaagctc ctgtcaggga acatgaagat tctccatgtc tcattgttat    1080
tgaagaaggt acttccctag cttcccttga ggaggtgacc aatgctgatg atctgccgaa    1140
gattgatgat gagaagaatt cccaatttga aacaagcccg catccaagtc cttctccttc    1200
agtagcttta gacactgaag aagggttaat caacccctact gcagaagaca ctgtagaaga    1260
gaacatagtg tctagcgaag taagttcgga tatcttgaaa gatgacggag atgccgtcga    1320
ggttgacaga gatactgcag aagtccagga agaaacggcc aacatacctg aatccaaact    1380
ctcggaggac acaggatcac ctcatcatca tgctgatatt ctgatggtgc aggaaaaagc    1440
tgcagaagaa catgacatga tagcctctgg agaccatgaa gaatttccag tcaatcctga    1500
taacaaacac tctgaagaaa atcagtcacc acatcatcat gctaataatg tgatggagca    1560
ggaccaagct gcagaagaac gtgagatcat atccccagga gaacataagg aaattccagc    1620
caatcctgat actaaagttg ttgaggagaa caatgacagg atagatgagg gtgaggctaa    1680
caatttgaat ttggctggcg atggaagtgg agcagtcgat catgattact tgaccaaaac    1740
ggagctggac aaagtgctag aggtgcctgg ttctgagacc atatcaaaac tggaggatag    1800
gccatctgag catctctcag aaacctcaat gaacgtggaa aaagaactag aaatgcctgc    1860
cgttgaaatt ttgccagaca atgacaaaaa ctctgatgtg ttggcagttg gagttttctgg    1920 agacagtgac aatgtggtat ctgtcttgcc cgcttcccaa acttcctctg atcgtgatga    1980
aggaatgatt acagttgatg ctgaacctac ggaagacatg aaacttgatg ttccagattc    2040
taaattggtt actgatacta ctgttgactc tactaataac aaggatgccc atgttgaggc    2100
taatactgaa aggcaagata attcagtgc acttgtgcta aatgatgcaa ataatgaaag    2160
tgcaccagtg aaacgtgtac ctggtcctta tgttgcatct tccaatataa agtctgaagc    2220
gcggggtagt ggagatttga acaatggagt acataaaata gttcggaccc cacctgtctt    2280
tgatgggacc atgcgcgcaa agcgctcttt cctcttggat gatgcgtctg atggtaatga    2340
atctggaacg gaagaggatc aatctgcttt tatgaaagaa ttggatagtt ttttagaga    2400 gcgaaacatg gatttcaaac ctccaaaatt ttacggggag ggactgaact gcctcaagta    2460
agcttgatac ccatcattat ttggtcactt tactgtgtta cattttaaaa ttttcagcag    2520
gagctgatat ctaatcaatt tctttggcac aaggttgtgg agagctgtaa ctagattggg    2580
cggatatgac aaggtacggg tcactgtgaa tacgcctgtt gaatgtcaca gcatcttttt    2640
```

-continued

```
tgacaagcaa atgtgacttc ggcttttcat ctttttgttcc atcctggctt acttgcatgc    2700
gtactgttgt tcatgatcta gcagtggtgc ttttggtgat tttctatgat tattatatgc    2760
ttttttatact ggataggtta ctggaagcaa attatggcgg caagtgggag agtctttcag   2820
gcccccaaag taagaagaat gcttttctta ttagtggttt gtcttagaaa ttttgggaaa    2880
tcatgtggat atttttaaga attaccctct aattggtcaa ttgtttgttc aggacatgta    2940
caacagtatc atggactttc cgaggtttct acgaaaaggt gagactatat tcaccacctt    3000
ttcctctctc tgcttttggt tcgtctatgt gacttttgta tacactggca tgggactggg    3060
actctatgta tcaacccttc tgagaaataa ttgaaatgat tgaacagtga acaactgtga    3120
atcatcttga gatatgtttt ccttaagata cagtaacatc ttgtaacatt atagtttctt    3180
catttttcag gctcttcttg aatatgagcg cataaagtt agtgaaggtg aacttcagat     3240
acccccttccg ttggaactag aaccgatgaa tattgataat caggtaaaat tgagaaaacc   3300
atatcatgtg tctgtagttt ttgtttgatc ttcttcttct gattaatgtc agtgttttaa    3360
cttaacccac tgccttgttt ctacactagg cgtctggatc agggagagca aggagagatg    3420
cagcatcacg tgctatgcaa ggttggcatt cacagcgtct taatggtaac ggtgaagtta    3480
gtgaccctgc aatcaaggtc cggtagaatc ttttttatatg tttcatttta cattcacact   3540
agatctctcg tttttttttt gtcaaacatt taatctatat ctcatagtct gaacgaacat    3600
actgttttgt aattaatagg ataagaactt agttcttcat caaaagcgcg aaaaacagat    3660
tggaaccacc cctggtatga gttctgtttg atgaagaagt gttgttctca ttttttatttt   3720
gaaactttga catgggttat cacttacatc tcacaatgtc atcaggtttg ctcaaacgta    3780
agagggctgc tgaacatggt gcaaaaaatg ccatccatgt atctaaatct atgtacgatt    3840
tttggctttg tggtctggtt ttcaatgcgt gataattcac atttgaattc tgattccagt    3900
tgttgttttt cctaggttgg atgtgactgt tgttgatgtt ggaccaccag ctgactgggt    3960
gaagattaac gtacagagaa cggtaaaatc aattgccact ttcttaaaaa cctgagcaat    4020
cactttctgg ttttacatat attaataaac tcttccacta tctgcagcaa gattgctttg    4080
aggtgtatgc attagtccca ggattagtcc gtgaagaggt aagctctcaa atctcgttgt    4140
gtttacatat ggatcctaag attgagttta gcactcagtt tttgtcttgg caacaataat    4200
acaggtccga gtccaatcag atccggctgg gcggttagta ataagtggcg aacccgagaa    4260
ccctatgaat ccttggggag ctactccttt caaaaaggta aatgctggtt acatgatttt    4320
tcagcttaca cgtagaatgt tgaatgacat tttcaaacct ccattgaaac tgcaggtggt    4380
aagtttacca acgagaatcg atccgcatca cacatcggct gtggtaaccc taaacgggca    4440
gttatttgtt cgtgtgcctc tggagcaatt ggagtagaaa catttacagt ttaacaaagc    4500
ctttgaagat ctgaaagaga aagattgtt agaagtagtt gttgagagta ttttgtttgt     4560
atattatgag agattaagca caacatgaga agagccttta ggaatccttta attaggccat   4620
ctagttttta ttgtctctcc tctctttgat tagattcttc ttctaagtgt catcactatt    4680
gatttgttgt agcaccaaac ttctttaaac cttttctatta agaacacaca aatctacaac   4740
cttttttattt ttttt                                                    4755
```

<210> SEQ ID NO 11
<211> LENGTH: 810
<212> TYPE: DNA
<213> ORGANISM: Arabidopsis thaliana

<400> SEQUENCE: 11

```
atgaaatcgt tttgcaagtt ggagtatgat caagtgtttg gcaaagaaaa taattcattc    60
tcatttctaa accactcatc actttactct catcaaagcg agttagcaaa tcctttcttc   120
gagttggaag acgagatgct tccttctgct acctctagta attgttttac ttctgcctca   180
agctttctgg ctttacctga tcttgaaccc atctccattg tgtctcatga agcagatata   240
cttagtgtgt atggttctgc ttcatggacc gcagaagaga cgatgttcgt ttctgatttt   300
gcgaaaaaga gtgaaaccac aactaccaag aagaggagat gcagaagaa atgttttct    360 agttgttctg tttcaaagac attgtcgaag gaaaccatct cattgtactt ttacatgccg   420
ataactcaag cggctagaga gcttaacatt ggtttaactc ttttgaagaa agatgccgc    480 gaattgggta ttaaacgttg gcctcatcgt aagctcatga gcctacaaaa actcatcagc   540
aatgtcaagg agctagagaa gatggaaggg gaagaaaatg aagataagct aagaaacgct   600
ttggaaaagc tcgagaagga agaaaaacg attgagaagt taccagattt gaagtttgag    660
gataagacaa agagattgag acaagcttgt ttcaaggcta accataagag gaagagaaga    720
agtggcatgt ccacgcccat cacatcatca tcttcttctg cttctgcttc ttcttcttct   780
tactcttctg tttcgggttt tgagagataa                                     810

<210> SEQ ID NO 12
<211> LENGTH: 269
<212> TYPE: PRT
<213> ORGANISM: Arabidopsis thaliana

<400> SEQUENCE: 12

Met Lys Ser Phe Cys Lys Leu Glu Tyr Asp Gln Val Phe Gly Lys Glu
1               5                   10                  15

Asn Asn Ser Phe Ser Phe Leu Asn His Ser Ser Leu Tyr Ser His Gln
            20                  25                  30

Ser Glu Leu Ala Asn Pro Phe Phe Glu Leu Glu Asp Glu Met Leu Pro
        35                  40                  45

Ser Ala Thr Ser Ser Asn Cys Phe Thr Ser Ala Ser Ser Phe Leu Ala
    50                  55                  60

Leu Pro Asp Leu Glu Pro Ile Ser Ile Val Ser His Glu Ala Asp Ile
65                  70                  75                  80

Leu Ser Val Tyr Gly Ser Ala Ser Trp Thr Ala Glu Glu Thr Met Phe
                85                  90                  95

Val Ser Asp Phe Ala Lys Lys Ser Glu Thr Thr Thr Lys Lys Arg
            100                 105                 110

Arg Cys Arg Glu Glu Cys Phe Ser Cys Ser Val Ser Lys Thr Leu
        115                 120                 125

Ser Lys Glu Thr Ile Ser Leu Tyr Phe Tyr Met Pro Ile Thr Gln Ala
    130                 135                 140

Ala Arg Glu Leu Asn Ile Gly Leu Thr Leu Leu Lys Lys Arg Cys Arg
145                 150                 155                 160

Glu Leu Gly Ile Lys Arg Trp Pro His Arg Lys Leu Met Ser Leu Gln
                165                 170                 175

Lys Leu Ile Ser Asn Val Lys Glu Leu Glu Lys Met Glu Gly Glu Glu
            180                 185                 190

Asn Glu Asp Lys Leu Arg Asn Ala Leu Glu Lys Leu Glu Lys Glu Lys
        195                 200                 205

Lys Thr Ile Glu Lys Leu Pro Asp Leu Lys Phe Glu Asp Lys Thr Lys
    210                 215                 220
```

Arg Leu Arg Gln Ala Cys Phe Lys Ala Asn His Lys Arg Lys Arg Arg
225                 230                 235                 240

Ser Gly Met Ser Thr Pro Ile Thr Ser Ser Ser Ser Ala Ser Ala
            245                 250                 255

Ser Ser Ser Ser Tyr Ser Ser Val Ser Gly Phe Glu Arg
            260                 265

<210> SEQ ID NO 13
<211> LENGTH: 897
<212> TYPE: DNA
<213> ORGANISM: Arabidopsis thaliana

<400> SEQUENCE: 13

| | | | | | |
|---|---|---|---|---|---|
| atggctgatc | acacaaccaa | agaacagaag | tcattctcat | tcctagctca | ttctccatcc | 60 |
| tttgatcaca | gctccttaag | ttatcccttta | ttcgactggg | aagaagatct | tcttgctctc | 120 |
| caagaaaact | ctggctctca | agcatttcct | tttactacaa | cttctctgcc | tttacctgat | 180 |
| cttgaaccct | gtctgaaga | tgtactcaat | tcatacagct | ctgcgtcatg | gaacgaaaca | 240 |
| gagcaaaaca | gaggagatgg | cgcttcatcg | gagaagaaga | gggaaaatgg | aacagtgaaa | 300 |
| gagacaacta | agaagaggaa | aatcaatgag | agacacagag | aacatagcgt | gagaatcatc | 360 |
| agcgatatta | ctacctacac | aactagttca | gctccaacga | cattgtcaaa | ggaaactgtc | 420 |
| tctcgctact | tctacatgcc | cataactcag | gctgcaatag | cacttaacgt | tggtttaact | 480 |
| ctactaaaaa | ggagatgtcg | cgaattgggt | attcgccgat | ggcctcatcg | taaacttatg | 540 |
| agcttaaaca | ctttgatcag | taacgtcaag | gagctgcaga | gatggaagg | cgaagagaat | 600 |
| gcagaaaaac | tgcaggacgc | gttggagatg | cttgagaagg | agaagaggac | aattgaggat | 660 |
| ttgccggatt | tggagtttaa | ggacaagaca | aagaggctaa | gacaagcttg | tttcaaggct | 720 |
| aaccacaaga | ggaagaagaa | gagaagtctc | aagtccgatc | agtctcaagt | accctcgtgt | 780 |
| tcaagcagcg | gatcagttcc | tagtgatgag | tcggttgatg | aagcaggaat | ggagagtgat | 840 |
| gaagaaatga | agtatctctt | gtgtggttttc | tcaagtgaat | ttactagtgg | tttgtga | 897 |

<210> SEQ ID NO 14
<211> LENGTH: 298
<212> TYPE: PRT
<213> ORGANISM: Arabidopsis thaliana

<400> SEQUENCE: 14

Met Ala Asp His Thr Thr Lys Glu Gln Lys Ser Phe Ser Phe Leu Ala
1               5                   10                  15

His Ser Pro Ser Phe Asp His Ser Ser Leu Ser Tyr Pro Leu Phe Asp
            20                  25                  30

Trp Glu Glu Asp Leu Leu Ala Leu Gln Glu Asn Ser Gly Ser Gln Ala
        35                  40                  45

Phe Pro Phe Thr Thr Thr Ser Leu Pro Leu Pro Asp Leu Glu Pro Leu
    50                  55                  60

Ser Glu Asp Val Leu Asn Ser Tyr Ser Ala Ser Trp Asn Glu Thr
65                  70                  75                  80

Glu Gln Asn Arg Gly Asp Gly Ala Ser Ser Glu Lys Lys Arg Glu Asn
                85                  90                  95

Gly Thr Val Lys Glu Thr Thr Lys Lys Arg Lys Ile Asn Glu Arg His
            100                 105                 110

Arg Glu His Ser Val Arg Ile Ile Ser Asp Ile Thr Thr Tyr Thr Thr
        115                 120                 125

```
Ser Ser Ala Pro Thr Thr Leu Ser Lys Glu Thr Val Ser Arg Tyr Phe
    130                 135                 140

Tyr Met Pro Ile Thr Gln Ala Ala Ile Ala Leu Asn Val Gly Leu Thr
145                 150                 155                 160

Leu Leu Lys Arg Arg Cys Arg Glu Leu Gly Ile Arg Arg Trp Pro His
                165                 170                 175

Arg Lys Leu Met Ser Leu Asn Thr Leu Ile Ser Asn Val Lys Glu Leu
            180                 185                 190

Gln Lys Met Glu Gly Glu Asn Ala Glu Lys Leu Gln Asp Ala Leu
        195                 200                 205

Glu Met Leu Glu Lys Glu Lys Arg Thr Ile Glu Asp Leu Pro Asp Leu
210                 215                 220

Glu Phe Lys Asp Lys Thr Lys Arg Leu Arg Gln Ala Cys Phe Lys Ala
225                 230                 235                 240

Asn His Lys Arg Lys Lys Arg Ser Leu Lys Ser Asp Gln Ser Gln
                245                 250                 255

Val Pro Ser Cys Ser Ser Gly Ser Val Pro Ser Glu Ser Val
        260                 265                 270

Asp Glu Ala Gly Met Glu Ser Asp Glu Met Lys Tyr Leu Leu Cys
        275                 280                 285

Gly Phe Ser Ser Glu Phe Thr Ser Gly Leu
        290                 295

<210> SEQ ID NO 15
<211> LENGTH: 834
<212> TYPE: DNA
<213> ORGANISM: Arabidopsis thaliana

<400> SEQUENCE: 15
atggctgatc aaagacctct aatgacctgg ttagaggcca caactatga atcattcctt    60 caagaagaca tattctcgtt tctcgatcaa tcacttttcg tcgatcctca cagctctttc   120
attgacccct taaggatttt caaacccaa aattggtttt ctctccaaga cagcattgtt   180
aatcatatat ctactacctt tgcggctgat catacgtttc tggcttcact tgatcttgaa   240
gctatctcta gtactttctc tctagatata tcgagtggat ggtggaacga gaataatggt   300
aactacaata accaggtcga accaaaacctt gatgaaattt caagaactaa taccatggga   360
gatccaaata tggagcaaat attgcatgaa atgttaaca caatgaaaga gaaaacaagc   420
cagaagagga taattatgaa gaggcgatat agagaagatg gagtcatcaa taatatgtca   480
agggaaatga tgaagcagta cttctacatg ccgataacta aagcagccaa ggagcttaac   540
attggtgtaa ccctcttgaa gaaagatgt cgtgagttag gtattcctcg ttggcctcac   600
cgtaagctca cgagcctaaa cgctctaatt gctaatctca aggacttgtt agggaacacg   660
aaggggagaa cgcccaagag taagctgagg aacgctttgg agcttttgga gatggagaag   720
aagatgattg aggaagttcc cgatttgaa tttggggata agactaagag gttaagacag   780
gcttgcttca aggctaaata caaacggaga aggctcttct catcttcttc atga          834

<210> SEQ ID NO 16
<211> LENGTH: 277
<212> TYPE: PRT
<213> ORGANISM: Arabidopsis thaliana

<400> SEQUENCE: 16

Met Ala Asp Gln Arg Pro Leu Met Thr Trp Leu Glu Ala Asn Asn Tyr
1               5                   10                  15
```

```
Glu Ser Phe Leu Gln Glu Asp Ile Phe Ser Phe Leu Asp Gln Ser Leu
         20                  25                  30

Phe Val Asp Pro His Ser Ser Phe Ile Asp Pro Phe Lys Asp Phe Gln
     35                  40                  45

Thr Gln Asn Trp Phe Ser Leu Gln Asp Ser Ile Val Asn His Ile Ser
 50                  55                  60

Thr Thr Phe Ala Ala Asp His Thr Phe Leu Ala Ser Leu Asp Leu Glu
 65                  70                  75                  80

Ala Ile Ser Ser Thr Phe Ser Leu Asp Ile Ser Ser Gly Trp Trp Asn
                 85                  90                  95

Glu Asn Asn Gly Asn Tyr Asn Asn Gln Val Glu Pro Asn Leu Asp Glu
             100                 105                 110

Ile Ser Arg Thr Asn Thr Met Gly Asp Pro Asn Met Glu Gln Ile Leu
         115                 120                 125

His Glu Asp Val Asn Thr Met Lys Glu Lys Thr Ser Gln Lys Arg Ile
 130                 135                 140

Ile Met Lys Arg Arg Tyr Arg Glu Asp Gly Val Ile Asn Asn Met Ser
145                 150                 155                 160

Arg Glu Met Met Lys Gln Tyr Phe Tyr Met Pro Ile Thr Lys Ala Ala
                 165                 170                 175

Lys Glu Leu Asn Ile Gly Val Thr Leu Leu Lys Lys Arg Cys Arg Glu
             180                 185                 190

Leu Gly Ile Pro Arg Trp Pro His Arg Lys Leu Thr Ser Leu Asn Ala
         195                 200                 205

Leu Ile Ala Asn Leu Lys Asp Leu Leu Gly Asn Thr Lys Gly Arg Thr
 210                 215                 220

Pro Lys Ser Lys Leu Arg Asn Ala Leu Glu Leu Leu Glu Met Glu Lys
225                 230                 235                 240

Lys Met Ile Glu Glu Val Pro Asp Leu Glu Phe Gly Asp Lys Thr Lys
                 245                 250                 255

Arg Leu Arg Gln Ala Cys Phe Lys Ala Lys Tyr Lys Arg Arg Arg Leu
             260                 265                 270

Phe Ser Ser Ser Ser
         275

<210> SEQ ID NO 17
<211> LENGTH: 771
<212> TYPE: DNA
<213> ORGANISM: Arabidopsis thaliana

<400> SEQUENCE: 17
atgagttcgt caaaacattc ctctgttttt aactattctg ctctgtttct atcactgttt      60
cttcaacaaa tggatcagaa ctctcttcat catctcgatt ctccaaaaat cgaaaacgag     120
tatgaaccag attcgttata cgacatgtta gataagttgc ctccgcttga ttctctccta     180
gatatggaag atttgaaacc aaatgcaggg ttgcactttc agttccatta caatagcttt     240
gaagatttct tcgaaaacat tgaagtggat aacacaattc catctgatat tcacttgttg     300
acacaagagc cctacttctc aagtgactcc tcttcctctt caccattggc tatccaaaac     360
gacggtctca tttccaacgt gaaagttgaa aaggtaacag ttaagaagaa gaggaacctt     420
aagaaaaaga ggcaagacaa attggagatg tctgagatca acaattttt cgataggccg     480 atcatgaaag cggctaaaga actgaacgtg ggactcactg tgttgaagaa gcgatgcagg     540
gaattaggaa tttaccggtg gcctcaccgg aagctcaaga gtctaaactc tcttataaag     600
```
aatctcaaga atgttggaat ggaagaggaa gtgaagaact tggaggaaca taggtttctt    660
attgaacaag aacctgatgc agaactcagt gatggaacca agaagctaag gcaagcttgt    720
ttcaaagcca attataagag aagaaaatca cttggtgatg attattattg a             771

<210> SEQ ID NO 18
<211> LENGTH: 256
<212> TYPE: PRT
<213> ORGANISM: Arabidopsis thaliana

<400> SEQUENCE: 18

Met Ser Ser Ser Lys His Ser Ser Val Phe Asn Tyr Ser Ala Leu Phe
1               5                   10                  15

Leu Ser Leu Phe Leu Gln Gln Met Asp Gln Asn Ser Leu His His Leu
            20                  25                  30

Asp Ser Pro Lys Ile Glu Asn Glu Tyr Glu Pro Asp Ser Leu Tyr Asp
        35                  40                  45

Met Leu Asp Lys Leu Pro Pro Leu Asp Ser Leu Leu Asp Met Glu Asp
    50                  55                  60

Leu Lys Pro Asn Ala Gly Leu His Phe Gln Phe His Tyr Asn Ser Phe
65                  70                  75                  80

Glu Asp Phe Phe Glu Asn Ile Glu Val Asp Asn Thr Ile Pro Ser Asp
                85                  90                  95

Ile His Leu Leu Thr Gln Glu Pro Tyr Phe Ser Ser Asp Ser Ser Ser
            100                 105                 110

Ser Ser Pro Leu Ala Ile Gln Asn Asp Gly Leu Ile Ser Asn Val Lys
        115                 120                 125

Val Glu Lys Val Thr Val Lys Lys Arg Asn Leu Lys Lys Lys Arg
    130                 135                 140

Gln Asp Lys Leu Glu Met Ser Glu Ile Lys Gln Phe Phe Asp Arg Pro
145                 150                 155                 160

Ile Met Lys Ala Ala Lys Glu Leu Asn Val Gly Leu Thr Val Leu Lys
                165                 170                 175

Lys Arg Cys Arg Glu Leu Gly Ile Tyr Arg Trp Pro His Arg Lys Leu
            180                 185                 190

Lys Ser Leu Asn Ser Leu Ile Lys Asn Leu Lys Asn Val Gly Met Glu
        195                 200                 205

Glu Glu Val Lys Asn Leu Glu Glu His Arg Phe Leu Ile Glu Gln Glu
    210                 215                 220

Pro Asp Ala Glu Leu Ser Asp Gly Thr Lys Lys Leu Arg Gln Ala Cys
225                 230                 235                 240

Phe Lys Ala Asn Tyr Lys Arg Arg Lys Ser Leu Gly Asp Asp Tyr Tyr
                245                 250                 255

<210> SEQ ID NO 19
<211> LENGTH: 360
<212> TYPE: DNA
<213> ORGANISM: Artificial sequence
<220> FEATURE:
<223> OTHER INFORMATION: EASE promoter

<400> SEQUENCE: 19
ccacgatgca aatatatcga taacgttatt aaaaaaagta accgcatgat atattctctt    60
tcgtatgata ttaaggccca cgatgcaaat atatcgataa cgttattaaa aaaagtaacc   120
gcatgatata ttctctttcg tatgatatta aggcccacga tgcaaatata tcgataacgt   180

```
tattaaaaaa agtaaccgca tgatatattc tctttcgtat gatattaagg cccacgatgc      240
aaatatatcg ataacgttat taaaaaaagt aaccgcatga tatattctct ttcgtatgat      300
attaaggcga tatccaagac ccttcctcta tataaggaag ttcatttcat ttggagagga      360

<210> SEQ ID NO 20
<211> LENGTH: 520
<212> TYPE: DNA
<213> ORGANISM: Arabidopsis thaliana

<400> SEQUENCE: 20
gaatttaact gatttggtca tctttaagat cataagtatt aataaggaat ccaaaagtta       60
tttaaggttt tgttagaaaa gcaagatagg catcatgagt tagtatctat atataatata      120 gaacttttg  atcttttaa  tcaaactata ttatacatat gtcttagttc ctaataaaat      180
gtgggcttca atagaatttt tgaaatataa agttttaaac ctgtaattgt ttgcacttat      240
tagatgtata ttactattta taccaatata taacagattt taataactaa acaattataa      300 tttttttaaca aaaagcaaac gtaataggtt actgaatttt actttataac aaaataaaac      360
gtttaaatga aaattaactc tttatataac atatttatct acagagccta taaatatgac      420
taaatattgc tttaatactc cagagcaaaa caaaagaaaa acaattcaca ataatattta      480
atatattttc tttgtgatat tggttaattt ctaccaagaa                            520

<210> SEQ ID NO 21
<211> LENGTH: 1419
<212> TYPE: DNA
<213> ORGANISM: Arabidopsis thaliana

<400> SEQUENCE: 21
tggcagggat acccagaaac cacatttgct tacatgtctt ctctataaca gagtgtgtaa       60
agttttgtgt gttgaaaggt ttttaatttt aagcaaaagt ggattatgac gacaacagac      120
aagcttttaa ttttatttta ccgtaatagt tatatcttgt tgtaagaaac catttttcagc     180 cttttgttgg aaaatcctgc ttaaatggtt tttgagtctt acataatagc ttcttcatct      240
tttgtcttct taaagagaat tatatttgta atttcatgtc tgttgtgttt ctttgacttt      300
actgaataga gaatttgtgt gtttatggtg aaaatatagc cgatctgctt gacagatgaa      360
cggagtttat tttgtctggt gacatgactc tgttctctta tatcaggatt tttgagaaac      420
cctttggtat ctttattgtt tggtctgaag gtatgtatat acttttttgtc tttgattaac      480 ctagtaatat gattactaac tcctgtaagt tcctcttttca gatcactaga acaaagcaag      540
aagttgtaat atctattgta tagtataaag atgctcgaaa aatttcagat tctggttagc      600
tctagttgta cagaagaaca aaaaagtctc taaagactca aatgtttcag aacgacctac      660
gcctatgagt gtctaaaccg gttaaatccg aaccgaaacg aatggaaaca gtcttgagaa      720
acaaaagagt aaaaaactga tcatagaatc acctagtttt actaaaaagt ggtatttaat      780
aaaattgctc tctaaacaac tttattaata acctacaaca agatttaatt tctcatttct      840
taagaggcca ttaactacaa gaatcacctg aaaagtatta actactcgca gccattatct      900
ccaattaatt gaaaccgttt ttttttttggt gggaaatgta ttattaattt cttaaccgtt      960
actcgcagct ccaactataa gtttataact attttttcgtt aacaattaaa atattaattg     1020
gcaccatacg ttcaagttta actgattaca aatactaagg agtatataat acttaggaaa     1080
aactgtaatt atatgaaatc aactagctac ttcacaaaag agcaaattaa ctacgattgg     1140
cttataaatt atatccatag atcagagaga tgctaagaga gacgtctatc cattacctaa     1200
```

```
tccttaaaaa aaacgtccct cttattagca ttagttacca ttaatcattt atatctctct    1260
cgtaactcca aagtttttac agggcaatca attagccgtc atacccactt tcccgtacat    1320
tttataactt cacttctata tctaccacta catgcatgta tatatatata cacaccgttc    1380
tctctctccc gttgattagt gatcacaaac ccattaata                           1419

<210> SEQ ID NO 22
<211> LENGTH: 579
<212> TYPE: DNA
<213> ORGANISM: Arabidopsis thaliana

<400> SEQUENCE: 22
aaatctttgg cttttttggat cgttcttttg tggaaatgga atataaaact tttttgttac      60
ttcattaata acttatgatt aatttatgaga aatggaaatt aaagatatat ggccatgatc    120
tacaataatg ttttaaccat acgtttcatt ttgttatctt aatcattcag ttagtggtta    180
ttaaacaata cataatcatg atcattgtga tgtgtatgta tgcgtatata taagaacatg    240
tacattgagt agtactacac tatttactcg aaatgattgc atgtcatata tgcatggaga    300
gacgaaaaga ggagtctaat ccaaatctaa acgcccctat aaattaccca ctaattaaca    360
ttaatcatat cttctcgtaa ctccaaattt aacacgacaa tcaattagcc gtcaatactc    420 aatacccccac ttctcctaat agattcatca tcacttccat tctttattct ctctccatat   480
cttactacca ctagtctctt ctctgaatgt agtatataaa tcttttctcg catcatcgag    540
tttcacaaca caacttctat ctctctcact ttctttaca                           579

<210> SEQ ID NO 23
<211> LENGTH: 525
<212> TYPE: DNA
<213> ORGANISM: Artificial sequence
<220> FEATURE:
<223> OTHER INFORMATION: intein

<400> SEQUENCE: 23
atggcacagg ttatcaacac gtttgacggg gttgcggatt atcttcagac atatcataag     60
ctacctgata attacattac aaaatcagaa gcacaagccc tcggctgggt ggcatcaaaa    120
gggaaccttg cagacgtcgc tccggggaaa agcatcggcg agacatcatt ctcaaacagg    180
gaaggcaaac tcccgtaagt ttctgcttct acctttgata tatatataat aattatcatt    240
aattagtagt aatataatat ttcaaatatt tttttcaaaa taaaagaatg tagtatatag    300
caattgcttt tctgtagttt ataagtgtgt atattttaat ttataacttt tctaatatat    360
gaccaaaaca tggtgatgtg caggggcaaa agcggacgaa catggcgtga agcggatatt    420
aactatacat caggcttcag aaattcagac cggattcttt actcaagcga ctggctgatt    480
tacaaaacaa cggaccatta tcagaccttt acaaaaatca gataa                    525

<210> SEQ ID NO 24
<211> LENGTH: 846
<212> TYPE: DNA
<213> ORGANISM: Escherichia coli

<400> SEQUENCE: 24
atggggacaa tgaagaaaaa tcgcgctttt ttgaagtggg caggggcaa gtatcccctg      60 cttgatgata ttaaacggca tttgcccaag ggcgaatgtc tggttgagcc ttttgtaggt    120
gccgggtcgg tgtttctcaa caccgacttt tctcgttata tccttgccga tatcaatagc    180
```

```
gacctgatca gtctctataa cattgtgaag atgcgtactg atgagtacgt acaggccgca    240
cgcgagctgt tgttcccga aacaaattgc gccgaggttt actatcagtt ccgcgaagag    300
ttcaacaaaa gccaggatcc gttccgtcgg cggtactgt tttatattt gaaccgctac     360 ggttacaacg gcctgtgtcg ttacaatctg cgcggtgagt taacgtgcc gttcggccgc    420 tacaaaaaac cctatttccc ggaagcagag ttgtatcact tcgctgaaaa agcgcagaat   480
gcctttttct attgtgagtc ttacgccgat agcatggcgc gcgcagatga tgcatccgtc    540
gtctattgcg atccgcctta tgcaccgctg tctgcgaccg ccaactttac ggcgtatcac    600
acaaacagtt ttacgcttga caacaagcg catctggcgg agatcgccga aggtctggtt     660
gagcgccata ttccagtgct gatctccaat cacgatacga tgttaacgcg tgagtggtat    720
cagcgcgcaa aattgcatgt cgtcaaagtt cgacgcagta taagcagcaa cggcggcaca    780
cgtaaaaagg tggacgaact gctggctttg tacaaaccag gagtcgtttc acccgcgaaa    840
aaataa                                                              846

<210> SEQ ID NO 25
<211> LENGTH: 375
<212> TYPE: DNA
<213> ORGANISM: Escherichia coli

<400> SEQUENCE: 25
atggggacaa tgaagaaaaa tcgcgctttt ttgaagtggg caggggcaa gtatcccctg     60 cttgatgata ttaaacggca tttgcccaag ggcgaatgtc tggttgagcc ttttgtaggt    120
gccgggtcgg tgtttctcaa caccgacttt tctcgttata ccttgccga tatcaatagc     180 gacctgatca gtctctataa cattgtgaag atgcgtactg atgagtacgt acaggccgca    240
cgcgagctgt tgttcccga aacaaattgc gccgaggttt actatcagtt ccgcgaagag    300
ttcaacaaaa gccaggatcc gttccgtcgg cggtactgt tttatattt gaaccgctac     360 ggttacaacg gcctg                                                    375

<210> SEQ ID NO 26
<211> LENGTH: 372
<212> TYPE: DNA
<213> ORGANISM: Artificial Sequence
<220> FEATURE:
<223> OTHER INFORMATION: intein

<400> SEQUENCE: 26
tgcctttctt tcggaactga gatccttacc gttgagtacg gaccacttcc tattggtaag    60
atcgtttctg aggaaattaa ctgctcagtg tactctgttg atccagaagg aagagtttac    120
actcaggcta tcgcacaatg gcacgatagg ggtgaacaag aggttctcga gtacgagctt    180
gaagatggat ccgttattcg tgctacctct gaccatagat tcttgactac agattatcag    240
cttctcgcta tcgaggaaat ctttgctagg caacttgatc tccttacttt ggagaacatc    300
aagcagacag aagaggctct tgacaaccac agacttccat tcccttttgct cgatgctgga   360 accatcaagt ga                                                        372

<210> SEQ ID NO 27
<211> LENGTH: 111
<212> TYPE: DNA
<213> ORGANISM: Artificial sequence
<220> FEATURE:
<223> OTHER INFORMATION: intein

<400> SEQUENCE: 27
```

```
atggttaagg tgattggaag acgttctctt ggtgttcaaa ggatcttcga tatcggattg      60
ccacaagacc acaactttct tctcgctaat ggtgccatcg ctgccaattg t             111
```

<210> SEQ ID NO 28
<211> LENGTH: 468
<212> TYPE: DNA
<213> ORGANISM: Escherichia coli

<400> SEQUENCE: 28

```
cgttacaatc tgcgcggtga gtttaacgtg ccgttcggcc gctacaaaaa accctatttc      60
ccggaagcag agttgtatca cttcgctgaa aaagcgcaga atgccttttt ctattgtgag     120
tcttacgccg atagcatggc gcgcgcagat gatgcatccg tcgtctattg cgatccgcct     180
tatgcaccgc tgtctgcgac cgccaacttt acggcgtatc acacaaacag ttttacgctt     240
gaacaacaag cgcatctggc ggagatcgcc gaaggtctgg ttgagcgcca tattccagtg     300
ctgatctcca atcacgatac gatgttaacg cgtgagtggt atcagcgcgc aaaattgcat     360
gtcgtcaaag ttcgacgcag tataagcagc aacggcggca cacgtaaaaa ggtggacgaa     420
ctgctggctt tgtacaaacc aggagtcgtt tcacccgcga aaaataa                  468
```

<210> SEQ ID NO 29
<211> LENGTH: 597
<212> TYPE: DNA
<213> ORGANISM: Corynebacterium diphtheriae

<400> SEQUENCE: 29

```
atggatcctg atgatgttgt tgattcttct aaatcttttg tgatggaaaa ctttttcttcg      60 taccacggga ctaaacctgg ttatgtagat tccattcaaa aaggtataca aaagccaaaa     120
tctggtacac aaggaaatta tgacgatgat tggaaagggt tttatagtac cgacaataaa     180
tacgacgctg cgggatactc tgtagataat gaaaacccgc tctctggaaa agctggaggc     240
gtggtcaaag tgacgtatcc aggactgacg aaggttctcg cactaaaagt ggataatgcc     300
gaaactatta agaaagagtt aggtttaagt ctcactgaac cgttgatgga gcaagtcgga     360
acggaagagt ttatcaaaag gttcggtgat ggtgcttcgc gtgtagtgct cagccttccc     420
ttcgctgagg ggagttctag cgttgaatat attaataact gggaacaggc gaaagcgtta     480
agcgtagaac ttgagattaa ttttgaaacc cgtggaaaac gtggccaaga tgcgatgtat     540
gagtatatgg ctcaagcctg tgcaggaaat cgtgtcaggc gatctgcgat gagctaa      597
```

<210> SEQ ID NO 30
<211> LENGTH: 846
<212> TYPE: DNA
<213> ORGANISM: Zea mays

<400> SEQUENCE: 30

```
tgctagtgaa cctcaaggat tgggggtgat aaatgcgtgc ttaattttg aggatctagt      60 aatcaagagt gagaggaggc aaaacatcga ttcttcatag tgcttaaata gaaaagagtg     120
ataatactac tcctttgttc gtcgagtact aaaagactac tacatccatt ttacaattat     180
tttttagata catcaaactt attattataa atctagacgt agttaagtgc aatgcaaaca     240
acttatattt tagtaataca taccattaat aaataatact agtagatagt atatatatct     300
aataagatga tattaaagga tgataataat aacaattaat aaatactact agtacacaaa     360
agataagttt agcaacaatt aagtttagta gtgcatgaag ttgttttacg atattgataa     420
```

```
tatttatcac gcaaattttg tatattatag tgatgttttt tgttccatat ctatgtttta      480
tacaaatttt ttactgccgc aatgcactgc acatatctag ttttagtact atatacaatt      540
aataaataat agataatact agcacatagt atatatctaa tgaaacgata ttaaaaggat      600
ggtaataata gcaattaata aatactagta gtatacaaaa gataagttta gcaacaatca      660
aactaaaaga tagccagtag aattttattt attttatatt actgaaaaca tcctcaagtg      720
ttcaccctgc agcccatcgc ctattctatt taagaaatgc ccgccctccc atactgctat      780
cactcaagcc tattctccat tgtggaacca acaaatctcc aagctctccc aatttagaaa      840
cgagcc                                                                 846
```

<210> SEQ ID NO 31
<211> LENGTH: 1113
<212> TYPE: DNA
<213> ORGANISM: Arabidopsis thaliana

<400> SEQUENCE: 31

```
atggtggacc aaggattttt cacactaaaa aaggaaaaaa agaaaaatat attaataaaa       60 ctttttatg ttaaaatctt gggcttctgc ttttgcgact cttggtcttc ttcggacatg       120
gcacattcct taacctcact cgccgttttc cagagcgtca tccgcaaaga gatggtgagg      180
agtttgcatg tctatgaatc ggtggagatt gagagagagt tctggttcaa gagcaaaagc      240
tgttatgtag agaagaaagc gaagcctctg tttcgttcgg aagatttccg cgaccggag       300 atctcggaag ggtcggtttt tggcacgtgg cgttgtatct ttgtgttccg gtttaatcac      360
tcgcttcctc ggtttcctac tcttctctgt cttccagaa tcccaaact ggaggacatc       420 cctaattag ccaacgagct caagtttatc tccgagttaa aaccatcaaa gatttatgaa      480
gaagaacaat gcagtagcag tacagaggga tattataact ctgatctgcc taaaccacga      540
aagctcgttc tgaaacaaga tcttaactgc cttcctgatt cagaaaccga atccgaggaa      600
tctgtaaacg aaaaaaccga acattcggaa tttgaaaacg ataaaactga acagtcggaa      660
tcagatgcta agactgagat tttgaagaag aagaagagga caccatcgag acatgttgct      720
gaactatcct tagaagagct ttcaaaatac tttgacctca ctatcgtgga agcttctcgg      780
aatctcaagg tcggtctcac tgttttgaaa agaaatgca gagagtttgg gattccacgg       840
tggcctcata ggaagatcaa atctctcgac tgtctcatcc acgatcttca gagggaagca      900
gagaagcagc aggaaaagaa tgaagcagca gcaatggcgg tagctaagaa acaggagaaa      960
ctggagacag agaagagaaa tatagtgaag agaccattca tggagatagg gatagaaacc     1020
aaaaaattca gacaagaaaa cttcaagaaa agacacaggg cttctagagc caagaagaat     1080
caagaatctc ttgtcacttc ctcttccact taa                                 1113
```

<210> SEQ ID NO 32
<211> LENGTH: 370
<212> TYPE: PRT
<213> ORGANISM: Arabidopsis thaliana

<400> SEQUENCE: 32

```
Met Val Asp Gln Gly Phe Phe Thr Leu Lys Lys Glu Lys Lys Asn
1               5                   10                  15

Ile Leu Ile Lys Leu Phe Tyr Val Lys Ile Leu Gly Phe Cys Phe Cys
                20                  25                  30

Asp Ser Trp Ser Ser Ser Asp Met Ala His Ser Leu Thr Ser Leu Ala
            35                  40                  45
```

```
Val Phe Gln Ser Val Ile Arg Lys Glu Met Val Arg Ser Leu His Val
 50                  55                  60

Tyr Glu Ser Val Glu Ile Glu Arg Glu Phe Trp Phe Lys Ser Lys Ser
 65                  70                  75                  80

Cys Tyr Val Glu Lys Lys Ala Lys Pro Leu Phe Arg Ser Glu Asp Phe
                 85                  90                  95

Arg Arg Pro Glu Ile Ser Glu Gly Ser Val Phe Gly Thr Trp Arg Cys
            100                 105                 110

Ile Phe Val Phe Arg Phe Asn His Ser Leu Pro Arg Phe Pro Thr Leu
        115                 120                 125

Leu Cys Leu Ser Arg Asn Pro Lys Leu Glu Asp Ile Pro Asn Leu Ala
130                 135                 140

Asn Glu Leu Lys Phe Ile Ser Glu Leu Lys Pro Ser Lys Ile Tyr Glu
145                 150                 155                 160

Glu Glu Gln Cys Ser Ser Ser Thr Glu Gly Tyr Tyr Asn Ser Asp Leu
                165                 170                 175

Pro Lys Pro Arg Lys Leu Val Leu Lys Gln Asp Leu Asn Cys Leu Pro
            180                 185                 190

Asp Ser Glu Thr Glu Ser Glu Glu Ser Val Asn Glu Lys Thr Glu His
        195                 200                 205

Ser Glu Phe Glu Asn Asp Lys Thr Glu Gln Ser Glu Ser Asp Ala Lys
210                 215                 220

Thr Glu Ile Leu Lys Lys Lys Arg Thr Pro Ser Arg His Val Ala
225                 230                 235                 240

Glu Leu Ser Leu Glu Glu Leu Ser Lys Tyr Phe Asp Leu Thr Ile Val
                245                 250                 255

Glu Ala Ser Arg Asn Leu Lys Val Gly Leu Thr Val Leu Lys Lys Lys
            260                 265                 270

Cys Arg Glu Phe Gly Ile Pro Arg Trp Pro His Arg Lys Ile Lys Ser
        275                 280                 285

Leu Asp Cys Leu Ile His Asp Leu Gln Arg Glu Ala Glu Lys Gln Gln
290                 295                 300

Glu Lys Asn Glu Ala Ala Ala Met Ala Val Ala Lys Lys Gln Glu Lys
305                 310                 315                 320

Leu Glu Thr Glu Lys Arg Asn Ile Val Lys Arg Pro Phe Met Glu Ile
                325                 330                 335

Gly Ile Glu Thr Lys Lys Phe Arg Gln Glu Asn Phe Lys Lys Arg His
            340                 345                 350

Arg Ala Ser Arg Ala Lys Lys Asn Gln Glu Ser Leu Val Thr Ser Ser
        355                 360                 365

Ser Thr
    370

<210> SEQ ID NO 33
<211> LENGTH: 2037
<212> TYPE: DNA
<213> ORGANISM: Arabidopsis thaliana

<400> SEQUENCE: 33
atacaaaaat attttatagt agtgaactac gatatatatc attgtggact gacttgtggt      60
gtgtgctgtc tcagcgatta gcaacctcac aaataaagtt aatactaata agtaccctac     120
tgtttaacga cctcacaaat caatactaat aacttctaaa tttgaaattt gttctctacg     180
tttcacacta catttatgga taatcgggtg tatctatagt atatgcatgc gttcgtatga     240
```

```
gttttaatac cagcgttgac tgtcggcaag taggaaataa tccaattaat aatacgtttg    300
acaaaagatt aaactgtagt actatatata atggaatatt taatccagat atcaaccgtt    360
gaaagttatc taatttaatt tgataacgat ttccaggact gtccccaaat ctatctgaaa    420
gttattaatc actcctttct aaacaataat tgaactttt cttaaaaaaa cttctacgac     480
aacacatttc ctttgcataa cgtagaagtc aatcaaagtt tttaaatact tctatcaaat    540
ttttaagtaa aatagtattg acacgaaatg caaaagacga agtatactga atataaaata    600
tcacggctac aatgcaacat ttaagaatta gatgattgga aatcgataca gaaaaataat    660
ctaagagaat taggccgtca cttgtgttgt gtgggagcaa acaaggacc aaaaatatcg     720 ggacaaatag gttggtccaa cctataggta gaggtagccc acttggcata gctcataata    780
ccattaccag ctcatatgtt ttttcaagga ttggagaaaa ttaaagaaag atgtaatcga    840
ttagagtaac agtggagtgc tgaatttaag ttagttaaga aaataattgg tgttacttct    900
tataaacttt taactcaaaa ccaattcgta atgaatagat agatccatgt ctattatatc    960
ttatatacta ttcaaacctc ttcttatata tttttccaat gtggattatt cgcccataga   1020
taaaagataa aacttaacaa ttggtaagac aatatgacat aaagtcctta gttctactta   1080
caaagaattt tgtcaattac cttccaaaat ttagatcttc taaaccctaa gttattgggt   1140
ttcaccaata taatgggtca tttcatctat tcacccgacc gttagattta ccaatttctc   1200
atcatatctc gattttcaac atttaagaaa gtaatcaagt ttagccgaaa tgcaagatga   1260
tacagaaaca atagcgttta acggtgttag atgataaact catcaactcc attaagaaaa   1320
ccaatcctgt aagaggtaaa gaaggggaga ccataattaa tgtctaatac tttcgtaatg   1380
accactatta atgattagta ctatgatcta tgaagttgaa gctctcttt tttttttttt    1440 tttttccctt cacgtccata gttagttaca gcattgatga aattttgct gagaatagac     1500 gaccctttat cctccaccct acgctttaag tggttgggag ttagaccctg ccagatagat   1560
tccaatccta agataagtct gtttaacaaa cctatcatat gtgaaagtga aaccattat    1620 gttgaagaat tatctaaggc gtagagataa tttctgcagc aaaaacattt ttttaaacat   1680
tgcgttatac attttaggat agtttatata atcagccaaa gtgtatattt ctgtaaaaca   1740
cattactatc ttgacatttt tgtgataagc tatataatca gtaacctgct acgtatagct   1800
taaccccact attataatta tgattcctca ttcagtaaaa ctatatagct gaattaataa   1860
agtttattag ggtctaatga agttggtgtg atcatttaat aatattgtta tttcataact   1920
cggaattgaa ttatttatta cccttgccat cttaaatcta catttgcaac tcacccaaaa   1980
gctttatcct ttgtgttttt tccactgtat actgaaaaca aatctgaggt gacgaag      2037

<210> SEQ ID NO 34
<211> LENGTH: 1358
<212> TYPE: DNA
<213> ORGANISM: Zea mays

<400> SEQUENCE: 34
acacaggacc aagaacttga agatgcattt gaaggccttt atcttgttga ctcccaaggg     60
ccctagactt tgtaatcttg catttgtgct ctgctgatct ggtctgatac tgatgtaact    120
gatcaatgaa ctaattgtat tagaactgga ttgtactctt ttttcctttt atatggtttt    180
ctcataaggc gagttttttac ctagaaaggt ttttaataag acagccattg cacaaacagc   240
tataatattt tatttaaagt ctatgagact gactccgtgt gtgctactgc ctactggcta    300
ctactatctg tgaaattgtg acctgtgaac tttgaaatgt gaaatttgtg acttgagaac    360
```

```
tatgatttta tgacatatga agttgtgaac tgtgtatttg atacctgtgt gaatttatga      420
cctatttagg ccttgttcgt ttacaccaat ccagctctgg attgacatgg attggaatta      480
aatacatgtc acaatctatg tcccaaaata atccaagcct actcattttt ttatttggtt      540
aaacccatca tagattataa cccaaggatt taggaaattt ttaaactatg gaagacatga      600
attctattca tagcttatta ggtatggaat aaatccatga atatattgca caagtttata      660
ttagaattca tgaatcaaaa gaataactag ttttgagaga tacatggatt aaatggtaga      720
tttaatctca ctatgggatt gagtgtgata tatggatta ttcaatccaa atccggatta       780
aatccatggt ggatctatat atattggtgt gctcttagct cggttgtgta ggtgggccat      840
gtttgacgtg ccgagctggc acgatcggac cttttacccg tgccgtgctc gtgcaagggg      900
tgttgcccgt caggaggcac cgtgagttaa tcggactcaa ttggaccgga ctcctcggat      960
cgcgccgtgc cgccgtttgg atttctatac ctgcacctgt ggcctgtggg gagtggggac     1020
tgcgaatgac attcttgcat ccctcctcac caatcaaggc ggcaacatac cggccctttg     1080
gccttccatg aacatgaacg cggcggaacg ccacgccggc gtgcactact cacctgcatg     1140
aattcgccgc ccactcacag cgccaaccca acttgaatgc acgcactacc atcaattcgc     1200
cgccgcggcc atcccttctg ccagctgcta tttatacgcc tcgccccgct ccagtctcag     1260
cagaaccacc agtcctccac tccatcttct actccgacca caaccacagc gaccacgacc     1320
gtgcacgtac gtacatgagc acaccaggca acggcacc                             1358

<210> SEQ ID NO 35
<211> LENGTH: 30
<212> TYPE: DNA
<213> ORGANISM: Zea mays

<400> SEQUENCE: 35
acacaggacc aagaacttga agatgcattt                                          30

<210> SEQ ID NO 36
<211> LENGTH: 25
<212> TYPE: DNA
<213> ORGANISM: Zea mays

<400> SEQUENCE: 36
gtgcctagct tattcgacga cctcg                                               25

<210> SEQ ID NO 37
<211> LENGTH: 25
<212> TYPE: DNA
<213> ORGANISM: Zoanthus sp.

<400> SEQUENCE: 37
agtccaagca cggcctgacc aagga                                               25

<210> SEQ ID NO 38
<211> LENGTH: 25
<212> TYPE: DNA
<213> ORGANISM: Zoanthus sp.

<400> SEQUENCE: 38
tacacggtgt cgaactggca gcgca                                               25

<210> SEQ ID NO 39
<211> LENGTH: 26
<212> TYPE: DNA
```

<213> ORGANISM: Anemonia majano

<400> SEQUENCE: 39

```
atggccctgt ccaacaagtt catcgg                                          26
```

<210> SEQ ID NO 40
<211> LENGTH: 29
<212> TYPE: DNA
<213> ORGANISM: Anemonia majano

<400> SEQUENCE: 40

```
ggaggtgtgg aactggcatc tgtagttgc                                       29
```

<210> SEQ ID NO 41
<211> LENGTH: 1262
<212> TYPE: DNA
<213> ORGANISM: Arabidopsis thaliana

<400> SEQUENCE: 41

```
gtttaggggt aatttagttt ttaaaatatc atttatgtgt tcttggaagt aacatattaa     60
tatcttaaca tgaaaatctt tggtcttggg gttttggttt tgcaaactta attctctgat   120
gttgaaattt gaccatctct tataatattt agaagtttgt gcttttgat agtccggagg    180
agtatgaatg atcaatgaac cctttcaact gtgaaaattt cgagtagatt aatattaata   240
agagtaaaat tttcattaaa gaaaattttc actaaagaaa caaacaaaat atcaaattaa   300
ctaaattaat aaagccctct tttatcagaa aaggtggcct acttcaaatg ttagggtgtc   360
ttattggttt gtgatttaaa taagttttt gtaacttaaa gtgttatgta aaatctgttg    420
ttattcaatc atttttatac aaagattttg atgtagttta gtgttatttg tttaagattt   480
tgtaaaaagt aatttaaaat cttcataaat ctagaattat tggattcata cttttataaa   540
attaataaag ttttgtgttg ttaaattaaa acaaaaaatc tataattgtt aataaattaa   600
attattatgt tattagttta taactttcta cactttattc ataaaataaa gttataaaaa   660
atatcatcaa ataagagat tgtttggaaa acttacaaaa atattaaaaa aaccaatcaa    720
caaaattata aaaataagt ctctaataat tatttaaaat ctatttactt tctataattt    780
tataaacgtc atcaaaatta tcctcgtatt agttttatct ggtgactttg ggcattttcc   840
ctttctcata aaagggcgcg tgactcaaaa ttaatgtata gatgtcccat aatttcatta   900
agaatagatt gttatttaa agtaacgtat cttttattta tgtagacaat attgttttca    960
cgcatgtctt actaatgatg ataatatata attaataatg aagacattta ttaggtctta  1020
tcaattatca ggaaaaaaaa gaaagacatt tattaggtca atttgctgac gctataaaag  1080
aaagacctta tcatttgatt ccaacacaat tcatacaaac atcttccaag taagtgattt  1140
ggttttgatc aatctttaac aatttctcg tattacaaca ccatcaaact aacaagtaac   1200
aacaatcatt ttttctattt tatttgatga aagggaaat agtttggtga tttctcgtaa   1260
ag                                                                 1262
```

<210> SEQ ID NO 42
<211> LENGTH: 1834
<212> TYPE: DNA
<213> ORGANISM: Arabidopsis thaliana

<400> SEQUENCE: 42

```
gctttaaagt cgtttatttt tgtaacatta ctctctattt ttgaaaaatg cgaaataatt    60
tttcaaagta aaaaataata tgcaatttag gctttataca tatattataa acgttttttc  120
```

```
gttcacatac atttgattttt caaaaataga aggtaagtt gaacttttcg tctcgagttc      180
tttgaattga tatattactt atcaaatttt aaaaaatatg agaaaactta acaatagcaa      240
tattatgtat tattttttac tttataaaat tattctgcaa atattgtgaa ttattttta       300 cttcaaaaaa ttattttgta ttcttttaag atgaaggata aagttataaa aatagacgac      360
tacaagaatt ttttccaca aatctccttt ttattcagat ggtcaaacat ggtcaaattg       420
atacataatc cacagaagtt gtagagagat tatagatgat ggactctttg tatgtcattc      480
tgttttttca gacagctaaa cgttatttaa aaataaaaa tacaatgcat taaaaacaac       540
catcctcgac ttgtgctcac gcaacgctac cgtcttcatc atttttaacct ctctcgacca    600 ttttaacctc tctcgacct ttttgttttt catttttttt aattaattat tttcaaacta      660
accgaaccca atcaactaaa tttacccta tttaactcaa ttttgaccag aaaaccaaaa       720
agttcgatta atttcgataa caaaataaaa taataacatg gttcttaaac ccaacccaca     780
cgaagaatcg gactgccttt tgggggcact tggccattgt gtcaaccggg ttgaccaca      840 agtcaattaa aaaaaaatta tttaatatat ttaatattta gaaaagttat atagtttata     900
ttaaataaaa ataaaaatag taataccaag tttaacaaaa gtctaacaat aataaacaac     960
taaattttaa ttaaatttga tgaatactaa atcattgtaa tattcgatcg tcattttagt    1020
ctaacaataa taatcaatta aaattttatt tattattttt aagtccaact aaaatctaaa    1080
accataacag aaatactaga gatcattgat gacgaaaata aactaagaaa acatcacgaa    1140
tttaaaataa tgaattttgt ttttctctc tcacaattct attcattctt aaaagcggg     1200 attgtgaagt cttaccaaaa tctaaaacat taaatgatga aaaagttcta aaaataagtg    1260
aatatagttt gaaaccctag attctattcc aaaatcaaat gaaaatttta aaaccccatag   1320 ccggcctgtt ttaatcgctt caccagatcg caagttaatg aagggttttt ttgtggatt    1380 ttctggttt agattgtcga gtattagtc taaacccaaa taggaaaaat gtccgggtag     1440
cggattacca tgtcggaccg gacggtccgg atcaggcgtg aaaacaatgc atgtaatcgt    1500
attgtgtcta atatagtatt tttgatttgt aataatttga agaaaaaaga gagtgttgtt    1560
atctttaagt ttgcccaaaa tctacagtaa tgttcgatca tagtctttaa agagagtgtt   1620
gttatcttta aagttacaac tttgtaaaat tagcatagtc tttaatataa acgtatctta   1680
aacaaaatta ttaaatgttg aagttagtaa catataacta ttaattaatg aacaaatatc   1740
ttttagtgat taacctataa aatctcttgt tttcttgttt catgtcatca atcttacatt   1800
caatactaaa agtattctta catccataaa aaaa                                1834

<210> SEQ ID NO 43
<211> LENGTH: 1248
<212> TYPE: DNA
<213> ORGANISM: Arabidopsis thaliana

<400> SEQUENCE: 43
ttagtcagca aaatcaaaat ttaacattta aataaagtct ttatttaata ttttatagca     60
tttataattt gaaatatgt aatgcaatga taaaaaataa aaataaaatt ctattatata     120
ctgaaatgat atccaacttt ttatacattc caaaactata tttggatgtc tcttgatctc    180
aactctgctc gtaggctatc taacaagtca gcagcaatat aggtcttcag tgggccttat    240
tgggcctcat tatgataagt aaagttctcg tagtggccta caaaaattat attgagggga    300
ccagataata gcttcacgtt tagaagtttc ataagggaa aactcatatt tcattttgt     360
```

| | | |
|---|---|---|
| tattgttgac gtataaacaa tccagatcat gaaaaaaaaa aagcgtataa acaatcttaa | 420 | |
| aattctaacc acttccaaat tagttttct cgaaactatt tgtgcttttt tgtttgtttt | 480 | |
| gcttttgtgg attttgattg gagaagagaa gaagaaatat tatatgtttt gcgtttgcat | 540 | |
| ttaggttttt tgtttgggtt tagaaatatt gaaactgatg tcttaactct taaaatatat | 600 | |
| atttagcgct attgtctaac gttgatgtag tttggcattt acttttttta ggtatgttgt | 660 | |
| atgcattaga gttaattgtt tgcttttgca ttttcacatt taatttgaat gtgtttgcgt | 720 | |
| tcaagataat taacattatt tgtttgtgtg ttttctttga aattaagaag ataatttgag | 780 | |
| ctaccactga attttgaaat tagagaggca tcgagggaaa caaatcatat agtttggtga | 840 | |
| ctgatttcaa ggggaaataa ccaaagaagg tcattagaag aataaatatg gttagccagt | 900 | |
| attgattagg aagataatca acatgttgac cacaatgaaa gttagtcaat gaacggtttt | 960 | |
| caaataaaga ttacaaaata actagaccat aaaaggtgat attctataaa ttctaattgt | 1020 | |
| tcttttatg tgttgtaata ataattgttt tattttaata actatatgta aaaattattg | 1080 | |
| tttatttatt tcttatatat tatggatgtc acgtgtataa ttatgaaaat ccacgactta | 1140 | |
| gaatgttcat gcattgcaat tgtaagaaag cacttatgcc ttctatatat atattcgttg | 1200 | |
| aaatgaaaac gataagagca caaaaacaaa aacaaagtag aaaaggat | 1248 | |

<210> SEQ ID NO 44
<211> LENGTH: 3674
<212> TYPE: DNA
<213> ORGANISM: Sorghum bicolor

<400> SEQUENCE: 44

| | | |
|---|---|---|
| cggaccgaag ctttcatgaa tacggccttg ctcctagggt tgagcactat gctgcgcttg | 60 | |
| tcaatctcat agggcgacat ggccagcttg aggatgcact ggaggtgatc aagagcatgc | 120 | |
| caattgctcc agaccgagct gtgtggggcg cattccttgg agcctgcact gctaaaaaga | 180 | |
| atgaagtgct ggctgcagtg gctgccaatg cattatccaa gattgatcct gagagttcag | 240 | |
| ctccatatgt tttgatgcat aacttacatg cccatgaggg gaggtgggga agtgcatctg | 300 | |
| tggttagaga agacatggaa cggctaggga ttcacaagca tccagggtac agctggattg | 360 | |
| atctgcacga caaggtgcat gtcttcatct caggggatac ctcgcatccc cttacccagg | 420 | |
| agattttttc agtgctagaa tgtttttata ggtcatgtag agattggagc tagacggcca | 480 | |
| tgtgaaattg ttatatttgg agaagagaag aggttttgcg gtgtagaaac aagctctttc | 540 | |
| ttccgtttct tcttggccta tacatgtctc ttgtaatgtt tgtacctttc tttggtaatg | 600 | |
| aaaacacaat aattttatta ttacatttga taaaattgaa gatccatctg gttgggaagg | 660 | |
| ctaggggat ttgaaggact agttttccca acaataacc cggcgacagt aggggtcata | 720 | |
| cgatgtcaat tctaaccctc tggtgcctat ggatccaaag aaacggagtg gtttttagag | 780 | |
| ggcaggagag gtcaccatta gacgtcctga gggacaacaa agacacagca tgctgctggg | 840 | |
| ctttagctcg accccagacg gctgctccac ctgcaattgg ttccctaggt agtgagtaat | 900 | |
| ctcttttctg ttttcatgcc ctagggcagc ctagactgtt tcaggggag cgctcctcgt | 960 | |
| gcgtgtatgc tactattcag cttcctcctt actattaatc aaagccggag ttttccggat | 1020 | |
| ctttaaaaaa aagagagaga taaaattgaa gatctatgat ggcactgctg attgtgtgaa | 1080 | |
| aactaaagta ctctcataca gatttccata atagtgatgt ggctgtcaaa tatttgcctg | 1140 | |
| caacttgaag aatttaaaat ggttgaaatt acatggagat gagccaactc aactgctcaa | 1200 | |
| gtaatctctc accccctgcc acttgaatgg atacataatt gccttttgcc tatgcatgat | 1260 | |

```
aattattgct gtaatgatca gttcataaat ttatgactaa agtaaaaacc ttagccttaa    1320
cccaaatcta tgatattagc tcaggcaaag agtatatgct agaaatttct atcattttaa    1380
ttgagtagca ctaatccttt gaaatgtgta aagaaaagt  tctagtatga tattagctca    1440
ggcaacccat tgagtcacaa ctccgtgcta cttctacttc ccaatgaaaa aaatgccatg    1500
catagatggc aaagactagc agtgctccta gattccttcg tgcaagtaga aacaaaatct    1560
tgaactgaat ctagccggaa agactttgat tgaccactat gcatgctctc taatgcacga    1620
accccaatgg catgctcggc aattaccaag agctaattat atctgtaact cccgatccat    1680
tagccaccct ttgcattaat tcctcgcgtg gttttaatg  gccgtttcca ttaacccaat    1740
gatcccaggg tttaaaagag ccgcattttt ccttccatct tgatcttctc catatattgc    1800
tggcctcaac tccgttccag catctcctcc cggaacccgg accgaagctt tcatgaatac    1860
ggccttgctc ctagggttga gcactatgct gcgcttgtca atctcatagg gcgacatggc    1920
cagcttgagg atgcactgga ggtgatcaag agcatgccaa ttgctccaga ccgagctgtg    1980
tggggcgcat tccttggagc ctgcactgct aaaaagaatg aagtgctggc tgcagtggct    2040
gccaatgcat tatccaagat tgatcctgag agttcagctc catatgtttt gatgcataac    2100
ttacatgccc atgagggag  gtggggaagt gcatctgtgg ttagagaaga catggaacgg    2160
ctagggattc acaagcatcc agggtacagc tggattgatc tgcacgacaa ggtgcatgtc    2220
ttcatctcag gggatacctc gcatccctt  acccaggaga ttttttcagt gctagaatgt    2280
ttttataggt catgtagaga ttggagctag acggccatgt gaaattgtta tatttggaga    2340
agagaagagg ttttgcggtg tagaaacaag ctctttcttc cgtttcttct tggcctatac    2400
atgtctcttg taatgtttgt acctttcttt ggtaatgaaa acacaataat tttattatta    2460
catttgataa aattgaagat ccatctggtt gggaaggcta gggggatttg aaggactagt    2520
tttcccaaac aataacccgg cgacagtagg ggtcatacga tgtcaattct aaccctctgg    2580
tgcctatgga tccaaagaaa cggagtggtt tttagagggc aggagaggtc accattagac    2640
gtcctgaggg acaacaaaga cacagcatgc tgctgggctt tagctcgacc ccagacggct    2700
gctccacctg caattggttc cctaggtagt gagtaatctc ttttctgttt tcatgcccta    2760
gggcagccta gactgttttc aggggagcgc tcctcgtgcg tgtatgctac tattcagctt    2820
cctccttact attaatcaaa gccggagttt tccggatctt taaaaaaag  agagagataa    2880 aattgaagat ctatgatggc actgctgatt gtgtgaaaac taaagtactc tcatacagat    2940
ttccataata gtgatgtggc tgtcaaatat ttgcctgcaa cttgaagaat ttaaaatggt    3000
tgaaattaca tggagatgag ccaactcaac tgctcaagta atctctcacc ccctgccact    3060
tgaatggata cataattgcc ttttgcctat gcatgataat tattgctgta atgatcagtt    3120
cataaattta tgactaaagt aaaaaccttc gccttaaccc aaatctatga tattagctca    3180
ggcaaagagt atatgctaga aatttctatc attttaattg agtagcacta atcctttgaa    3240
atgtgtaaaa gaaaagttct agtatgatat agctcaggc  aacccattga gtcacaactc    3300
cgtgctactt ctacttccca atgaaaaaaa tgccatgcat agatggcaaa gactagcagt    3360
gctcctagat tccttcgtgc aagtagaaac aaaatcttga actgaatcta gccggaaaga    3420
ctttgattga ccactatgca tgctctctaa tgcacgaacc ccaatggcat gctcggcaat    3480
taccaagagc taattatatc tgtaactccc gatccattag ccacccttg  cattaattcc    3540 tcgcgtggtt tttaatggcc gtttccatta acccaatgat cccagggttt aaagagccg    3600
```

-continued

```
cattttcct tccatcttga tcttctccat atattgctgg cctcaactcc gttccagcat    3660
ctcctcccgg aacc                                                     3674

<210> SEQ ID NO 45
<211> LENGTH: 1808
<212> TYPE: DNA
<213> ORGANISM: Oryza sativa

<400> SEQUENCE: 45
tttccatcct atcgagatgt actactccac ttctgttctg tgcaggttga atatatgtgg      60
cccaatcaca tcttgccact aaaaatctta catttatcca tatactccac gaacagtaga    120
ttttactcat ccctgattag acccaaaaca atcatgagca cggtagacaa cacaagctta    180
gggcgtcttg cacgattagg ttttgttcgg tttagagggg attgaagagg attagagggg    240
actgaggggt aataatttca caccataata ggtattgaat aaatcccctc taatcccttc    300
ctcatgagaa ttaaccgaac aagcccttac cccgctacac ccaaaatgt ttccgctggg     360 gtgcaatact gctatcgatg gcttcttacg taggaatttc atttttctaa tatttttca     420 ttaaaaattg tacaaatatg acaaatctct tttataaaac aaaggtttct atagaaatta    480
tgcgagcaca tatgttcaca tatacacata tttcatattt atgactaatt ttttttca     540 acgacaccga caaatccgtc aataggcttt attttctttt cacaaagccc gtaaacttcc    600
ataggagcct actacatcag tggcttcgtg ccgcactaac gaggcatcta tagtgattga    660
ctttatcaat gtaaaatatg acagccaaat attttgatgg gaggtgttca tggttatatg    720 tacgttata ctccgtatga gtgagtagca ctccctccgt tctgagatat ttactagtac     780
tacgaatctg gaaatactct ttattcagat tcattgtact ataaaagtat ctcatatatc    840
caaaaatttt tatattttga gaccgagtga atatatgttt gtggttttcc tacatgtgag    900
tagagtgcat cagtggatat tagagcctcc acgatatggg aatagtatca gccagtgtgt    960
tgatgacgtc aaagctcaaa gggtagatga aaagttcatg cttcaaaaat ggcatgtctt   1020
ggaaactggg atttttcctaa taatgagaaa tcctatgtgc agagaggaga caaaagcact   1080
gctcaacaca ctgcaggctg caaagatttg ctagtactac tactccagta cacaaacaca   1140
tcattggcca cttccctaat ctcatttaac gtttgcataa cgcactcatt ctgcggttac   1200
tgcattagct actcatgaat gtggctattt actagtagta caattctaag tgccattccc   1260
aggaggagtg agcagcttct ccacccttaa tcaggggcgg agctaattgg ttttggcgat   1320
caatctgcct cgtcgagtcg tcgttccgcc ctccacactt cccagttcgc gactgcgcca   1380
acgattgcgc gagcaccgct gccgcaactc aactcccgtg accgacggcg gcaatcggtg   1440
gccggcgagg cagcgatcag gatcagggta agtatatttc atctcctcct cctgtccttt   1500
ggccctccct tctctgatcc ctcccgtctt cattaagctc taatcctagg tactaaatta   1560
ctaatttgat tagtaagcgg ttaggccact agaacttgcg cccttgccga cggccaacac   1620
gacgctcgca ggccacaaga caaaagctga atgaagcacc ggcatcgcat gaactgatcg   1680
cattgtgttg gtaaattcta acttctatg tcgacatatt acatttatag tgttaaagaa    1740
aatttatgtt cagttggacc atcctagcct aaaatcgtag ctacgccact gcccttaagc   1800
ccttgccc                                                            1808

<210> SEQ ID NO 46
<211> LENGTH: 582
<212> TYPE: DNA
<213> ORGANISM: Arabidopsis thaliana
```

<400> SEQUENCE: 46

```
aaatctttgg cttttggat cgttcttttg tggaaatgga atataaaact ttttgttac      60
ttcattaata acttatgatt aattatgaga aatggaaatt aaagatatat ggccatgatc    120
tacaataatg ttttaaccat acgtttcatt ttgttatctt aatcattcag ttagtggtta    180
ttaaacaata cataatcatg atcattgtga tgtgtatgta tgcgtatata taagaacatg    240
tacattgagt agtactacac tatttactcg aaatgattgc atgtcatata tgcatggaga    300
gacgaaaaga ggagtctaat ccaaatctaa acgccctat aaattaccca ctaattaaca     360
ttaatcatat cttctcgtaa ctccaaattt aacacgacaa tcaattagcc gtcaatactc    420
aataccccac ttctcctaat agattcatca tcacttccat tctttattct ctctccatat    480
cttactacca ctagactcta tcagtgatag agtatataaa tcactctatc agtgatagag    540
tttcacaaca caactactct atcagtgata gagtttacaa tg                      582
```

<210> SEQ ID NO 47
<211> LENGTH: 582
<212> TYPE: DNA
<213> ORGANISM: Arabidopsis thaliana

<400> SEQUENCE: 47

```
aaatctttgg cttttggat cgttcttttg tggaaatgga atataaaact ttttgttac      60
ttcattaata acttatgatt aattatgaga aatggaaatt aaagatatat ggccatgatc    120
tacaataatg ttttaaccat acgtttcatt ttgttatctt aatcattcag ttagtggtta    180
ttaaacaata cataatcatg atcattgtga tgtgtatgta tgcgtatata taagaacatg    240
tacattgagt agtactacac tatttactcg aaatgattgc atgtcatata tgcatggaga    300
gacgaaaaga ggagtctaat ccaaatctaa acgccctat aaattaccca ctaattaaca     360
ttaatcatat cttctcgtaa ctccaaattt aacacgacaa tcaattagcc gtcaatactc    420
aataccccac ttctcctaat agattcatca tcacttccat tctttattct ctctccatat    480
cttactacca ctagactcta tcagtgatag agtatataaa ctctatcagt gatagagtag    540
tttcacaaca ctctatcagt gatagagtct ttctttacaa tg                      582
```

<210> SEQ ID NO 48
<211> LENGTH: 582
<212> TYPE: DNA
<213> ORGANISM: Arabidopsis thaliana

<400> SEQUENCE: 48

```
aaatctttgg cttttggat cgttcttttg tggaaatgga atataaaact ttttgttac      60
ttcattaata acttatgatt aattatgaga aatggaaatt aaagatatat ggccatgatc    120
tacaataatg ttttaaccat acgtttcatt ttgttatctt aatcattcag ttagtggtta    180
ttaaacaata cataatcatg atcattgtga tgtgtatgta tgcgtatata taagaacatg    240
tacattgagt agtactacac tatttactcg aaatgattgc atgtcatata tgcatggaga    300
gacgaaaaga ggagtctaat ccaaatctaa acgccctat aaattaccca ctaattaaca     360
ttaatcatat cttctcgtaa ctccaaattt aacacgacaa tcaattagcc gtcaatactc    420
aataccccac ttctcctaat agattcatca tcacttccat tctttactct atcagtgata    480
gagtctacca ctagtctctt ctctgaatgt agtatataaa tcactctatc agtgatagag    540
tttcacaaca caactactct atcagtgata gagtttacaa tg                      582
```

<210> SEQ ID NO 49
<211> LENGTH: 273
<212> TYPE: DNA
<213> ORGANISM: Bacillus amyloliquefaciens

<400> SEQUENCE: 49

| | | |
|---|---|---:|
| atgaaaaaag cagtcattaa cggggaacaa atcagaagta tcagcgacct ccaccagaca | | 60 |
| ttgaaaaagg agcttgccct tccggaatac tacggtgaaa acctggacgc tttatgggat | | 120 |
| tgtctgaccg gatgggtgga gtacccgctc gttttggaat ggaggcagtt tgaacaaagc | | 180 |
| aagcagctga ctgaaaatgg cgccgagagt gtgcttcagg ttttccgtga agcgaaagcg | | 240 |
| gaaggctgcg acatcaccat catactttct taa | | 273 |

<210> SEQ ID NO 50
<211> LENGTH: 1314
<212> TYPE: DNA
<213> ORGANISM: Arabidopsis thaliana

<400> SEQUENCE: 50

| | | |
|---|---|---:|
| ctgagaagga catggtcggt gatcatacac ggcgaggtgg aaatgttata tttactattg | | 60 |
| aaaactaaat tatttattat agagggagat attactcttt acgctttcat taagatttat | | 120 |
| ttttataagt tttaaagtat tttattgtta tatgaagata aaatatatta tttatttata | | 180 |
| ttttatttta taataagata ttatttttta ttttttttta ttattttatt tttattctct | | 240 |
| gtgctatata tactctgaaa gtctgaatat ataatccatt tggtgtgggg agtattagac | | 300 |
| tattaattat ggtcaattaa atgaagttca aaaatatgaa tggaagatat atgaataaat | | 360 |
| tgaattaata gatgtttata attattgaga ctgctttagc gtagaaaatg ctgcatacat | | 420 |
| tattgttggg aaaataaaaa tgagtattaa tatttaacat aaatattaaa tgtctttaat | | 480 |
| atgtgtgaga gaattattaa aaaaaatcaa catttacgaa agagatggac tataaacatt | | 540 |
| tcgttaatac attttgtttt tggtaaatt ggtttaatac aatatttttg aatcgtaaag | | 600 |
| tgttctggta atatgatatg acatctaaat gaaatgatta tgccagaaga tcattgtctt | | 660 |
| gaatattggc tgtattaacc tctaacgaaa ttgagttaat atatattttg aatttaccat | | 720 |
| ttgatattta gattgtataa tttgagttta ccagctatat atcgtgttga acttgcatgt | | 780 |
| aacacaccac ttttttccac cgattttttgt ttatggaaat ataagtcaat atttattcgt | | 840 |
| caaatacata tatactcacg caaatatacg tccttaaaga gaaagagat tttcatgatt | | 900 |
| attttttgaaa aaagagaaga ttttgaaaga tgacaacaag caacgatata tgaacgcgca | | 960 |
| tagcatgtga tgggatgggg cgggcctatg aaattttga acgtttacaa acttagggcc | | 1020 |
| tattattaga agatattact agcttttaat aaacgaatta tccctattaa ccaaaataat | | 1080 |
| caacactaat cattaatttc tacttactat ctctctcgta acttacagaa aacatataat | | 1140 |
| gattttgacg gctcatcatc tcggagaact aaataccac ttcccactta tcatgtactt | | 1200 |
| tctctatcta tgcatgtacg ttaagttgtt tatatatata tatacacacg attcattttc | | 1260 |
| cttgttttaa gactaacgaa cgttacaatc tatctatatc cactttcaat cgaa | | 1314 |

<210> SEQ ID NO 51
<211> LENGTH: 654
<212> TYPE: DNA
<213> ORGANISM: Arabidopsis thaliana

<400> SEQUENCE: 51

| | | |
|---|---|---:|
| aacaccaata tgaagagaaa aaagcttgat tctttctcat tactcttcaa gaactcaaaa | | 60 |

```
ttacattgtg ttttggtgtt tcttcttcga gctcaaatca tcttggggtt ttcacagatt    120
tattcaaaca atgtactccc aagattatta ttgggagtat tattatgtag tgcgaactcg    180
atttgagaag tgaaaaaaag atggttacat ttaaagcttt tgatttgact acgttttctt    240
tgtttcattt actaagtaaa ttatcactta gtggagactc tcattatctc ttaatcatct    300
tcaacatcaa atgtatctat catcgtaaca tataacacgt gcatcatcta atgcgataat    360
acacaaaaac tcaattcatt taatatcgat tgtgaatttt tagcaatatg atcttatcaa    420
ctttcatgca ttgactttga ctagaggaag tagaaaaaaa taatcgtcat catcattaaa    480
gaagcaacta acctcacaca aattcagccc ccgtgatcat atatacttaa ttaaagtcac    540
acggtaatta attaagatta acatttaatg atttctaata cgctttggga ctcgtaactc    600
ccattacatt gcaatcccta tgaacattca tctttgtttt tacagagact atat          654

<210> SEQ ID NO 52
<211> LENGTH: 2164
<212> TYPE: DNA
<213> ORGANISM: Arabidopsis thaliana

<400> SEQUENCE: 52
aatcctcttc tttagggttt ctttccgact ttgaatacac tctctgcttt ttttttctgct     60 ttctaaaaag tcttcaacac tttgctttct ctcatcttct tttttttttc cctctttttt    120
tttaaccttt ctttagacca cgtgagaaag ataacttcca ctttaaacac ttgtcctctt    180
ctgtcttatt gtcttgtctt gtcttttctt gataggcttc cattattgtg gctagggccc    240
aaaaaggcct taaagcccaa agcttcgtgg ttttcttct cttgtggttt aggctttaca    300
gtgatcagag aaacccaaaa cacgttggaa acgtctaagc agagaaaaac agagcttcca    360
acaaattcag cattgtaatt cttctagacg ttttatacaa attttacata tacactatgg    420
aactctcctt gcatttctac caaatctgaa ttgaaaaagg gatttgtaag atatgaaaat    480
gcgataacgt tgcctagatt aatcagtttt cgacattttt ttttcctgt tccgattcca    540 tgtaactttt tgagggccac aacttttctt aattaaaaaa ataagaaaaa taaaagctca    600
agtgacaatc agttttgaa aatgatacta actaagctct taacattttt acgcatgtat    660
ataaacatta atcttttatt tggtcttaaa tacaaagcat atatatgatg ctatcaatct    720
aaatggtcta tttgtacata attaaataaa acataaaatt aaagcctgcg catacaacat    780
gtctacaacc aaaaacttct ttcgtttata tcaaatcaa catcccaata cttcatcttc    840
tcttctcttc tatttggcac ttatagacgc gaaaggtttg aaccggcggg aaagtaagac    900
accataatcg gagctctcgg ggatttgctt tttggtttct ttgaggacag gactttcaag    960
tcactctcat cagttgagct aatctttgag tctgattttg gaacaaagca atcaaagacg   1020
gaggcaaaga gagaacacat gatcatagga gtttgaaaaa cgtgtttgga gtctatatac   1080
gatgaatgat atgattaaga tttgatctca ggtaattacg tgaacgatat gtatttataa   1140
gacaacccat ctttataaat tcttggacac gtttctagga aatgaccact aaatcttgct   1200
ggccaagctt tgccctattc ttaattgttt tctcttttga caacacttgg gcaccttttt   1260
tgactctttg ggcctaattg gaccaactat tgataccaaa catacgttaa catcacctcc   1320
atatcactca cccaatcaag ttttccaaaa tgttatgatt aaaattaggg tcttcatgtc   1380
actatccaac aaaagttttc caaaattcaa cattaaaatt aggggaaata tgtacgaaat   1440
agaacttata tatccatgtt aagaagaaaa aaaactatat atccaagcaa tacaaaatat   1500
```

```
ttaggttcta cactccattt tatacaaaat attaattgtt ttcgattaga gttttattag    1560
aaagttctca ctcagataaa atcaaaacta gtactctgta tttttatata gagaaaaatc    1620
cttgtaagtt aatgttacta atactaccca agtacccaga gtattttgac acattctatt    1680
gacttttgat tgaaacatgt ccggcttaat ttaacgcaat tattcagttt agattttgaa    1740
caccttaaat gaattggctt ttaacagatc ataatatcaa taccagtttt agtccttgag    1800
aactcagccc atgacttaaa atatgaaaac ttcagcccat gacttaataa atgaacaaag    1860
agaacccaaa aacagaaaat gaatcatgga catatttaca tatatcataa tctgaccaaa    1920
ttggaaatta tgctcaaatg cttaatattc ctctgattca tttaccaaat tcaacctctg    1980
tagaatcatt ctaaacaaaa ttcaattacc acttttcaga catgcgtcgc gcgtgtgagt    2040
gtttagctac atgggcttgg ttcggtgcaa cccgcttccc actgttaatt ttacataact    2100
accctcgcac gctccgcttg cctacacgtg cgttccggaa tattctgcct ttttggtaat    2160
ttcg                                                                 2164
```

<210> SEQ ID NO 53
<211> LENGTH: 978
<212> TYPE: DNA
<213> ORGANISM: Arabidopsis thaliana

<400> SEQUENCE: 53

```
gtacagggaa aaatgcggtg taaataccaa actttacgaa gcgtggcaaa aatgttataa      60
aaaaaaaatc tataaaactt tgttattgtg atgtgaagga atcgccctag tcaacaaatt     120
aaatcacaat caccccatga acacaactga tttaactata tcaacttttt cttgaaccaa     180
aggtaccaag tacaaactaa taacgatacg agttgtcagt tgtgtaccaa gtttttactg     240
gcaaataaat cgacttgcta ccaaagtacc aactaatacg agtgtctctg ttttgttaac     300
ttgacccaat cttctcttcct cgtctctttg caaaacgctt aagcccaaat ataactaata     360
tggcccaaaa tattcttgag agatccaaac ctataactcg aatacccggt aggacaaaac     420
gcttcatgtc atattctgac acttttaac acttcatgat cggtatttaa atagcatttt     480
catttcttgt ataacaactg agttcatata tacatcat tgatcatata ttgagtattg     540
atctaactaa ttcataatca actattcaac tgttttcatt aaaaaaaaca agtttcgtat     600
ataaaacttg gaatattgt ttttaattaa tttgaacgta cattgttatg ggttcttcta     660
atgttaagaa acaccaaag agagaaaaaa gggtggtcaa aaacaaatt tagaaatcaa     720 tgctataatt aagctatgat aaactaatca ttttttatc gaaacgtaat gaaactaatt     780
ttaaatttta acaatcaacg attttacttt tttgtctcag tctaaaaata acaatcgggt     840
ttctaatata aaacaaactc ggtgctccac gagaatagtt gtcctcttct caaacatatc     900
tcaacttatt gtttgaatat aaaagagat atcaaaaga agagaagacc aaaaacaaaa     960 caaaatctc taataacc                                                    978
```

<210> SEQ ID NO 54
<211> LENGTH: 524
<212> TYPE: DNA
<213> ORGANISM: Arabidopsis thaliana

<400> SEQUENCE: 54

```
gaaaattgtg caaagctttt catgtgcggc tcagattaat tagtcattta ctactaataa      60
aactttcact ttggggtcta gtagataatt ctccaccccc attgaatctt tttagtggag     120
gtctaaacat acataagatt ctatagattg acatttggga aaccatcctc atacaaaaaa     180
```

```
gacctaaacg gaatctatga agaattatta acagaaaaga aaaacagatg gcaatgagaa      240
aagatcgggt tcaaggaaaa cacagccgta caaaactcaa gaacaaaaac accaaaaata      300
aacaaaaaaa cttccaaaaa tagatataga atcacatggt tttgttgttt tgtctatttg      360
ttctctataa aaggagatat ttggttggat ctatcatagc gtctcctctc aaccaaagct      420
tacaatttgt tctcccttaa aaactaaatt ttacaaataa actctcaaat ccaagagagg      480
agaagaccga agtaaaaaca caagaaaaaa aaggattaag gcac                       524

<210> SEQ ID NO 55
<211> LENGTH: 995
<212> TYPE: DNA
<213> ORGANISM: Arabidopsis thaliana

<400> SEQUENCE: 55
atttagaagt gggaatgggt ctatgaaatg agattacgtc aatatgagtg aaattgataa       60
attatccaat cccataaacg agatggtgaa caaatataaa tttacattta ctgctagtaa      120
atacaactac aattactttt taccacgcaa aaggagagag gagagatttt ttttttttt      180 ttacttcgta aggataatat gtacttagaa aataatatac agtgacgaag gatgatgaat      240
gctttcatgg gaaacgagca attgaccagg ttgagagaga tatgggccga ttaaagctgt      300
cactgtctct gttatgacag aactaagttc acgtttacgt gatttaaatt tttattgata      360
gaggagatga ttgtgtttac aatcactgaa ttgttactga ttttactgtg aattgcatat      420
caattggtaa acctgtaaaa ttgtcttatc attttgtgga ttaccaatca tatttatgag      480
aaatctcaat tccatttaca taaatattta aaagacaatt acagaataat ttagctatga      540
cgctccgaca taatcaacaa acaaaacaat attttgcatc tgtatatata tatatacaaa      600
attttgttac acatacacat aattttgagg aagaaacaaa aattattatt tggttgcaat      660
tttagactgt tttataatta accgagtaat attgatcatt ctcaaccact taatcaattg      720 attcttttt tttttttttt tgcttgatat aaaaaaagtt acggtaaaat tggaaatcgt      780
tactacctaa gattggggtc aacaatccgt aaaagaagat ggaatcacac actgtaatac      840
caatactttt ctataaggaa tcaaatctat aaatagcata ctaactagca ctataaaaac      900
attatgaatc ctcctatgag caaatcactt ttaaatttgt taacactctt ttaaaagaac      960
aaaaaaagca aaaaaaaaat aaagatatta tcacc                                 995

<210> SEQ ID NO 56
<211> LENGTH: 1783
<212> TYPE: DNA
<213> ORGANISM: Arabidopsis thaliana

<400> SEQUENCE: 56
actcaaaagg catagctaca ttaattctca gaaaatcatc aaacaaatac tttatgttat       60
aatcactagc tagtaaatgt tttttttttt ttgtaaaata aaatcaagat tggtataggg      120
caaccacaga tctattgatc gacctatgct aggataactc tgtaaaaaca aatatagatt      180
gtaacaaaca ttcagaagtg aggcgagctc acattaataa aagtttttga taattttcgt      240
ctcaacacaa aagtaattaa gcagttataa tcttttacca tatttcataa ttatgatcgc      300
tacattaaaa aaaaaatcta cttcaatttc attttcatt tttatctttg caatgaccta      360
acacaaattc ttccatgaga tcaaccttt cataagaaag ggagattgaa tcaaagacca      420
ccataataaa ttaaaaatac tgtccaagaa aaaaatagtt ttgttgacgc caatgatcga      480
```

```
atatgttata ggattgtgct tttttctatt tttgcgggta attgtgaggt tacttcatga    540
aagaagatca acaatctttg cggccaattt ggtaagctac aaaactaagc ctatgtctga    600
gcagttcacg taagcttctc tagtggctct tcaatccaat tttcaaacta aacgtgtgat    660
ttccacactt aaatctcacg tatatttatt cggttcttat ggttccgaga caggttctgg    720
tctagtgtaa ctgagaaaag ctccttataa atttctgcat gtttctattt ttaaccgttt    780
gcatgcaatt catacaagtt tagtaagggt tttttttttgg ggtcaaagat gccagtttta   840
gtagttctta aaccgatttt gtaaaagcta tggacgattc gaatttatct cctcggaaga    900
ttgtatataa accataattt atacgaatga ttgattttttg gtagtttaat tggtctttgt   960
gagtgttctt agacttttct cttgatggtt gtttgatctt aaaacatttc ccatgtgaag   1020
tctaactctc ttatagtatt atacaatagc aaaaacatgt tagagatttt aagagaattg   1080
aatagtttaa ttattttagt caacttattt tagtttaaac cttttaacat ttccaccatc   1140
atacaaataa actatttaat taacactttg taaggtgtaa cactttttag catgtatgca   1200
ttatatatta ttttgtttaa ctcagtgaag tattcatctg aatacaagtt aactatgaat   1260
atatagtcct gtcttcttac atgaaagagt catattttaa taccacatag caacagcaat   1320
aatattgtta catgctataa tatcagagca tccacaaaga caattggtcc actagtcaga   1380
gatgtaccta gcttatgttg agcgacaaga aatcaaatat tttggtacgt acagtgatca   1440
acatgtgaat agtaagatat gcaacccgat atacagtcat ttacataact agattgatga   1500
tccataaaga ccgaaaaagt agtggtcata aacgaatgtt gcacaaattt tgtttaagag   1560
tcagttacat aataatttgc atctaaatat agattaaaga aaaatgcgga tcacagcaat   1620
agaaattgcc gtcaaaatag agagtgaaac aagagaacct cttttgctat tcaattgcaa   1680
ccttaaacca atccaccatt ttctcttatt cacataaaaa atagagttttt aaccatctat  1740
ataaacccca cctcacctag aaagtaaaat catcccaaaa gga                     1783
```